US008313901B2

(12) United States Patent
Breaker et al.

(10) Patent No.: US 8,313,901 B2
(45) Date of Patent: Nov. 20, 2012

(54) METHODS AND COMPOSITIONS RELATED TO THE MODULATION OF RIBOSWITCHES

(75) Inventors: Ronald R. Breaker, Guilford, CT (US); Kenneth F. Blount, New Haven, CT (US); Izabela J. Puskarz, West Hartford, CT (US); John K. Wickiser, Cornwall on Hudson, NY (US)

(73) Assignee: Yale University, New Haven, CT (US)

( * ) Notice: Subject to any disclaimer, the term of this patent is extended or adjusted under 35 U.S.C. 154(b) by 280 days.

(21) Appl. No.: 12/158,168

(22) PCT Filed: Dec. 21, 2006

(86) PCT No.: PCT/US2006/062494
§ 371 (c)(1),
(2), (4) Date: Mar. 16, 2009

(87) PCT Pub. No.: WO2007/100412
PCT Pub. Date: Sep. 7, 2009

(65) Prior Publication Data
US 2009/0305253 A1    Dec. 10, 2009

Related U.S. Application Data

(60) Provisional application No. 60/752,726, filed on Dec. 21, 2005.

(51) Int. Cl.
*C12Q 1/68* (2006.01)
*C07H 21/02* (2006.01)
*C07H 21/04* (2006.01)
*C12N 5/00* (2006.01)

(52) U.S. Cl. ...... 435/6.1; 536/23.1; 536/24.1; 536/24.5; 536/24.3

(58) Field of Classification Search .......... None
See application file for complete search history.

(56) References Cited

U.S. PATENT DOCUMENTS

| | | | |
|---|---|---|---|
| 3,687,808 A | 8/1972 | Merigan | |
| 4,469,863 A | 9/1984 | Tso | |
| 4,476,301 A | 10/1984 | Imbach | |
| 4,683,195 A | 7/1987 | Mullis | |
| 4,683,202 A | 7/1987 | Mullis | |
| 4,800,159 A | 1/1989 | Mullis | |
| 4,845,205 A | 7/1989 | HuynhDinh | |
| 4,868,116 A | 9/1989 | Morgan | |
| 4,883,750 A | 11/1989 | Whiteley | |
| 4,980,286 A | 12/1990 | Morgan | |
| 4,981,957 A | 1/1991 | Lebleu | |
| 4,987,071 A | 1/1991 | Cech | |
| 5,023,243 A | 6/1991 | Tullis | |
| 5,034,506 A | 7/1991 | Summerton | |
| 5,118,800 A | 6/1992 | Smith | |
| 5,130,302 A | 7/1992 | Spielvogel | |
| 5,134,066 A | 7/1992 | Rogers | |
| 5,166,315 A | 11/1992 | Summerton | |
| 5,175,273 A | 12/1992 | Bischofberger | |
| 5,177,196 A | 1/1993 | Meyer, Jr. | |
| 5,185,444 A | 2/1993 | Summerton | |
| 5,188,897 A | 2/1993 | Suhadolnik | |
| 5,214,134 A | 5/1993 | Weis | |
| 5,216,141 A | 6/1993 | Benner | |
| 5,235,033 A | 8/1993 | Summerton | |
| 5,264,423 A | 11/1993 | Cohen | |
| 5,264,562 A | 11/1993 | Matteucci | |
| 5,264,564 A | 11/1993 | Matteucci | |
| 5,276,019 A | 1/1994 | Cohen | |
| 5,278,302 A | 1/1994 | Caruthers | |
| 5,286,717 A | 2/1994 | Cohen | |
| 5,297,721 A | 3/1994 | Schneider | |
| 5,319,080 A | 6/1994 | Leumann | |
| 5,321,131 A | 6/1994 | Agrawal | |
| 5,334,711 A | 8/1994 | Sproat | |
| 5,354,855 A | 10/1994 | Cech | |
| 5,359,044 A | 10/1994 | Cook | |
| 5,367,066 A | 11/1994 | Urdea | |
| 5,393,878 A | 2/1995 | Leumann | |
| 5,399,676 A | 3/1995 | Froehler | |
| 5,405,938 A | 4/1995 | Summerton | |
| 5,405,939 A | 4/1995 | Suhadolnik | |
| 5,432,272 A | 7/1995 | Benner | |
| 5,434,257 A | 7/1995 | Matteucci | |
| 5,446,137 A | 8/1995 | Maag | |
| 5,453,496 A | 9/1995 | Caruthers | |
| 5,455,233 A | 10/1995 | Spielvogel | |
| 5,457,187 A | 10/1995 | Gmeiner | |
| 5,459,255 A | 10/1995 | Cook | |
| 5,466,677 A | 11/1995 | Baxter | |
| 5,466,786 A | 11/1995 | Buhr | |

(Continued)

FOREIGN PATENT DOCUMENTS

| | | |
|---|---|---|
| EP | 0070685 | 1/1983 |
| EP | 0320308 | 6/1989 |
| EP | 0329822 | 8/1989 |
| EP | 0360257 | 3/1990 |
| GB | 981458 | 1/1965 |
| JP | 2007259787 | 10/2007 |
| WO | 8706270 | 10/1987 |
| WO | 8801315 | 2/1988 |
| WO | 8902439 | 3/1989 |
| WO | 8906700 | 7/1989 |

(Continued)

OTHER PUBLICATIONS

Winkler, et al. (2004) Control of Gene Expression by a Natural Metabolite-Responsive Ribozyme, Nature, v.428:281-6.*
Guo, et al. (1995) Efficient Trans-Cleavage of a Stem-Loop RNA Substrate by a Ribozyme Derived From Neurospora vs RNA, The EMBO Journal, v.14(2):368-76.*
Guo et al, EMBO J., vol. 14, pp. 368-375 (1995).*
Winkler et al, Nature, vol. 428, pp. 281-286 (2004).*

(Continued)

*Primary Examiner* — Sean McGarry
(74) *Attorney, Agent, or Firm* — Pabst Patent Group LLP

(57) ABSTRACT

Disclosed herein are methods and compositions related to the detection of conformational changes and interactions with trigger molecules in riboswitches.

26 Claims, 9 Drawing Sheets

U.S. PATENT DOCUMENTS

| | | | |
|---|---|---|---|
| 5,470,967 A | 11/1995 | Huie |
| 5,476,925 A | 12/1995 | Letsinger |
| 5,484,908 A | 1/1996 | Froehler |
| 5,489,677 A | 2/1996 | Sanghvi |
| 5,502,177 A | 3/1996 | Matteucci |
| 5,514,785 A | 5/1996 | Van |
| 5,519,126 A | 5/1996 | Hecht |
| 5,519,134 A | 5/1996 | Acevedo |
| 5,525,711 A | 6/1996 | Hawkins |
| 5,536,821 A | 7/1996 | Agrawal |
| 5,539,082 A | 7/1996 | Nielsen |
| 5,541,306 A | 7/1996 | Agrawal |
| 5,541,307 A | 7/1996 | Cook |
| 5,550,111 A | 8/1996 | Suhadolnik |
| 5,552,540 A | 9/1996 | Haralambidis |
| 5,561,225 A | 10/1996 | Maddry |
| 5,563,037 A | 10/1996 | Sutherland |
| 5,563,253 A | 10/1996 | Agrawal |
| 5,567,811 A | 10/1996 | Misiura |
| 5,571,799 A | 11/1996 | Tkachuk |
| 5,576,427 A | 11/1996 | Cook |
| 5,587,361 A | 12/1996 | Cook |
| 5,587,469 A | 12/1996 | Cook |
| 5,591,722 A | 1/1997 | Montgomery |
| 5,594,121 A | 1/1997 | Froehler |
| 5,596,086 A | 1/1997 | Matteucci |
| 5,596,091 A | 1/1997 | Switzer |
| 5,597,909 A | 1/1997 | Urdea |
| 5,602,240 A | 2/1997 | De Mesmaeker |
| 5,608,046 A | 3/1997 | Cook |
| 5,610,289 A | 3/1997 | Cook |
| 5,610,300 A | 3/1997 | Altmann |
| 5,614,617 A | 3/1997 | Cook |
| 5,618,704 A | 4/1997 | Sanghvi |
| 5,623,070 A | 4/1997 | Cook |
| 5,624,803 A | 4/1997 | Noonberg |
| 5,625,050 A | 4/1997 | Beaton |
| 5,627,053 A | 5/1997 | Usman |
| 5,631,359 A | 5/1997 | Chowrira |
| 5,633,360 A | 5/1997 | Bischofberger |
| 5,639,873 A | 6/1997 | Barascut |
| 5,646,265 A | 7/1997 | McGee |
| 5,648,211 A | 7/1997 | Fraiser |
| 5,658,873 A | 8/1997 | Bertsch-Frank |
| 5,663,312 A | 9/1997 | Chaturvedula |
| 5,670,633 A | 9/1997 | Cook |
| 5,677,437 A | 10/1997 | Teng |
| 5,677,439 A | 10/1997 | Weis |
| 5,681,941 A | 10/1997 | Cook |
| 5,700,920 A | 12/1997 | Altmann |
| 5,712,124 A | 1/1998 | Walker |
| 5,714,331 A | 2/1998 | Buchardt |
| 5,719,262 A | 2/1998 | Buchardt |
| 5,744,311 A | 4/1998 | Fraiser |
| 5,807,718 A | 9/1998 | Joyce |
| 5,834,186 A | 11/1998 | George |
| 5,854,038 A | 12/1998 | Sullenger |
| 5,861,288 A | 1/1999 | Usman |
| 6,001,411 A | 12/1999 | Kester |
| 6,518,252 B2 | 2/2003 | Wooley |
| 6,831,171 B2 | 12/2004 | Breaker |
| 2003/0108949 A1 | 6/2003 | Bao |
| 2004/0072783 A1 | 4/2004 | Breaker |
| 2004/0219523 A1 | 11/2004 | Stanton |
| 2005/0053951 A1 | 3/2005 | Breaker |
| 2006/0088864 A1* | 4/2006 | Smolke et al. ............... 435/6 |
| 2007/0016983 A1 | 1/2007 | Muhlbauer |
| 2011/0035839 A1* | 2/2011 | Lutfiyya et al. ............ 800/279 |

FOREIGN PATENT DOCUMENTS

| | | |
|---|---|---|
| WO | 8907136 | 8/1989 |
| WO | 8909284 | 10/1989 |
| WO | 9002806 | 3/1990 |
| WO | 9007641 | 7/1990 |
| WO | 9103162 | 3/1991 |
| WO | 9207065 | 4/1992 |
| WO | 9315187 | 8/1993 |
| WO | 9323569 | 11/1993 |
| WO | 9402595 | 2/1994 |
| WO | 9413688 | 6/1994 |
| WO | 9506731 | 3/1995 |
| WO | 9511910 | 5/1995 |
| WO | 9610390 | 4/1996 |
| WO | 9610391 | 4/1996 |
| WO | 9610392 | 4/1996 |
| WO | 9610395 | 4/1996 |
| WO | 9619836 | 6/1996 |
| WO | 9717076 | 5/1997 |
| WO | 9717471 | 5/1997 |
| WO | 9726270 | 7/1997 |
| WO | 9827104 | 6/1998 |
| WO | 9843993 | 10/1998 |
| WO | 9916871 | 4/1999 |
| WO | 9954459 | 10/1999 |
| WO | 0020040 | 4/2000 |
| WO | 0026226 | 5/2000 |
| WO | 2004027035 | 4/2004 |
| WO | WO 2004/270305 * | 4/2004 |
| WO | wo2004027035 * | 4/2004 |
| WO | 2008033866 | 3/2008 |
| WO | 2008076156 | 6/2008 |

OTHER PUBLICATIONS

Tinsley et al., RNA vol. 13:468-477, 2007.*

Abrue-Goober and Merino, "Ribex: a web server for locating riboswitches and other conserved bacterial regulatory elements", Nucleic Acids Res., 33:W690-92 (2005).

Agrawal, et al., Antisense oligonucleotides: toward clinical trials, TIBTECH. 14: 376-380 (1996).

Ahn, et al., Vitamin B1 functions as n activator of plant disease resistance, Plant Physiol., 138:1505-15 (2005).

Akimoto, et al., "Queuine analogues, their synthesis and inhibition of growth of mouse L5178Y cells in citro", J. Med. Chem., 29:1749-53 (1986).

Akimoto, et al., "Synthesis of queuine, the base of naturally occurring hypermodified nucleoside (queuosine), and its analogues", J. Chem. Soc. Perkin Trans., 1:1637-44 (1988).

Altschul, et al., Gapped BLAST and PSI-BLAST, a new generation of protein database search programs, Nucleic Acids Res., 25:3389-3402 (1997).

Anagnostopoulos, et al., "Requirements for transformation in *Bacillus subtilis*", J. Bacteriol., 81:741-746 (1961).

Anderson, et al., "ModE-dependant molybdate regulation of the molybdenum cofactor operon moa in *Escherichia coli*", J. Bacteriol., 182:7035-43 (2000).

Antson, et al, "The structure of trp RNA-binding attenuation protein", Nature, 374:693 (1995).

Auger, et al., "The metIC operon involved in methionine biosynthesis in *Bacillus subtilis* is controlled by transcription antitermination", Microbiol., 148:507-518 (2002).

Axmann, et al., "Identification of cyanobacterial non-coding RNAs by comparative genome analysis", Genome Biology, 6:R73 (2005).

Babitzke and Gollnick, "Posttranscription Initiation control of tryptophan metabolism in *Bacillus subtilis* by th trp Rna-binding attenuation protein (TRAP), anti-TRAP, and RNA structure", J. Bacteriol., 183:5795-5802 (2001).

Bader, et al., "Structure of the molybdenum-cofactor biosynthesis protein MoaB of *Escherichia coli*", Acta Cryst., D60:1068-75 (2004).

Badet-Denisot, et al., "Mechanistic investigations on glucosamine-6-phosphate synthase", Bull. Soc. Chim. Fr., 130:249-255 (1993).

Baker and Boxer, "Regulation of the chIA locus of *Escherichia coli* K12: involvement of molybdenum cofactor", Mol Microbiol., 5:901-907 (1991).

Banerji, et al., "A lymphcyte specific cellular enhancer is located downstream of the joining region in immunoglobulin heavy chain genes", Cell, 33:729 (1983).

Barker, et al., "Superfamily classification in PIR-International protein sequence database", Methods Enzymol, 266:59-71 (1996).

Barrick, et al., "New RNA motifs suggest an expanded scope for riboswitches in bacterial genetic control", PNAS USA, 101:6421-26 (2004).

Barrick and Breaker, "The distributions, mechanisms, and structures of metabolite-binding riboswitches", Genome Biol., 8:R239 (2007).

Bartel and Szostak, "Isolation of new ribzymes from a large pool of random sequences", Science, 261:1411-1418 (1993).

Bassler and Losick, "Bacterially Speaking", Cell, 125:237-46 (2006).

Bateman, et al., "The Pfam Protein Families Database", Nucleic Acid Res., 30:276-280 (2002).

Batey, et al., "Structure of a natural guanine-responsive ribswitch complexed with the metabolite hypoxanthine", Nature, 432:411-415 (2004).

Batey, "Structures of regulatory elements in mRNAs", Current Opin. Struct. Biol., 16:299-306 (2006).

Baugh, et al., Molybdenum metalloenzymes, Comprehensice Biol. Catalysis, vol. 111:377-4010 (1998).

Baugh, et al., "2.8 A cyrstal sturcture of the malachite green aptamer", J. Mol. Biol. 301:117-128 (2000).

Bayer, et al."Programmable ligand-controlled riboregulators of eukaryotic gene expression", Nat. Biotechnol. 23:337-343 (2005).

Bayly, et al., "A well-behaved electrostatic potential based method using charge restraints for deriving atomic charges—the RESP model", J. Phys. Chem., 97:10269-80 (1993).

Beaucage and Leyer, "The functionalization of oligonucleotides via phosphramidte derivatives", Tetrahedron, 49:1925-1963 (1993).

Beaudry and Joyce, "Directed evolution of an RNA enzyme", Science, 257: 635-641 (1992).

Beaudry and Joyce, "Minimum secondary structure requirements fro catalytic activity of a self-splicing group I intron", Biochemistry, 29:6534-6539 (1990).

Been, et al., "Secondary structure of the self-cleaving RNA of hepatitis delta virus: Applications to catalytic RNa design", Biochemistry, 31:11843-11852 (1992).

Beigelman, et al., "Chemical modification of hammerhead ribozymes", J. Biol. Chem., 270:25702-08 (1995).

Beigelman, et al., "Synthesis of 1-Deoxy-D-Ribofuranose Phosphoramidite & the incorporation of abasic nucleotides in stem-loop II of a hammerhead ribozyme", Biorganiz & Medical Chem. Lttrs., 4:1715-20 (1994).

Bellon, et al., "Post-synthetically ligated ribozymes: an alternative approach to iterative solid phase synthesis", Bioconjugated Chem., 8:204-212 (1997).

Bellon, et al. "Amino linked ribozymes: post-synthetic conjugation of half-ribozyme", Nucleasides & Nucleotides, 6:951-954 (1997).

Benner, et al., "Modern mertabolism as a palimpsest of the RNA world", PNAS, 86: 7054-7058 (1989).

Benseler, et al., "Hammerhead-like molecules containig non-nucleoside linkers are active RRNA catalysts" . J. Am. Chem. Soc., 115: 8483-8484 (1993).

Berkner, et al, "Abundant expression of polyomavirus middle T antigen and dihydrofolate reductase in an adenovirus recombinant". J. Virology, 61:1213-220 (1987).

Bevers, et al., "Tungsten transport protein A (WtpA) in pyrococcus furiosus: the first member of a new class of tungstate and molybdate transporters", J. Bacterial., 188:6498-6505 (2006).

Beyhan and Yildiz, "Smooth to rugose phase variation in *Vibrio cholerae* can be mediated by a single nucleotide change that targets c-di-GMP signalling pathway", Mol. Microbiol., 63:995-1007 (2007).

Bienz and Kubli, "Wild-type tRNA TyrG reads the TMV RNA stop codon, but Q bas-modified tRNA TyrQ does not", Nature, 294:188-190 (1981).

Birikh,et al.,"The structure, function and application of the hammerhead ribozyme," Eur. J. Biochem., 245:1-16 1997.

Black, "Protein diversity from alternative splicing: a challenge for bioinformatics and post-genome biology", Cell, 103:367-70 (2000).

Blaise, et al., "A minimalist glutamyl-tRNA synthetase dedicated to aminoacyltion of the tRNA aspQUC anticodon", Nucleic Acids Res., 32:2768-75 (2004).

Blencrowe, "Alternative splicing, new insights for global analyses", Cell, 126:37-47 (2006).

Blount, et al., "Antibacterial lysine analogs that target lysine riboswitches", Nature Chem. Biol., 1:44-49 (2007).

Blount, et al., "Development and application of a high-throughput assay for Glms riboswitch activators". RNA Biology, 3(2):77-81 (2006).

Bock, et al., "Photoaptamer arrays applied to multiplexed proteomic analysis", Proteomics, 4:609-618 (2004).

Bocobza, et al., "Ribswitch-dependent gene regulation and its evolution in the plant kingdom", Genes Dev., 21:2874-79 (2007).

Bonhoeffer, et al. "RNA multi-structure landscapes: a study based on temperature dependent partition functions", Eur. Biophys. J., 22 13-24 (1993).

Borchardt,et al., "Potential inhibitor of S-adenosylmethionine-dependent methlytransferase 1. Modification of the amino acid portion of S-adenosylhomocysteine", J. Med. Chem., 17:862-868 (1974).

Borsuk, et al., "L-Arginine influences the structure and function of arginase mRNA in aspergillus nidulans", Biol. Chem., 388:135-144 (2007).

Bout, "Lung gene therapy: in vivo adenovirus-mediated gene transfer to rhesus monkey airway epithelium", Human Gene Therapy, 5:3-10 (1994).

Boy, et al., "Isolation and identification of mutants constitutive for aspartokinase III synthesis in *Escherichia coli* K 12". Biochimie, 61:1151-1160 (1979).

Braasch and Corey, "Novel antisense and peptide nucleic acid strategies for controlling gene expression". Biochem., 41(14):4503-4510 (2002).

Branch, "A good antisense molecule is hard to find", Trends Biochem. Sci., 23 (2): 45-50 (1998).

Breaker, "Are engineered proteins getting competition for RNA", Current Opinion in Biotechnology, 7:442-448 (1996).

Breaker, "Catalytic DNA: in training and seeking employment". Nature Biotech., 17: 422-423 (1999).

Breaker, "Engineered Allosteric Ribozymes as Biosensor Components", Curr Opin. Biotechnol., 13:31-39 (2002).

Breaker, "In vitro selection of catalytic polynucleotides", Chem. Rev, 97:371-390 (1997).

Breaker, "Natural and engineered nucleic acids as tools to explore biology", Nature Biotechnol., 432:838-845 (2004).

Breaker., "In vitro Selection of Self-cleaving Ribozymes and Deoxyribozymes". In: Intracellular Ribozyme Applications: Principles and Protocols. L. Couture, J. Rossie eds. Horizon Scientific Press, Norfolk, England (1999).

Breaker and Joyce, "A DNA enzyme that cleaves RNA". Chem. Bio., 1:223-229 (1994).

Breaker and Joyce, "Inventing and improving ribzyme function: rational design versus iterative selection methods", TIBTECH., 12:265-275 (1994).

Breaker et al., "A DNA enzyme with Mg2+ dependent RNa phophoresterase activity", Chem Biol., 2(10): 655-660 (1995).

Brennan, et al., "Two-deminsional parallel array technology as a new apporach to automated combinatorial solid phase organic sythesis", Biotech. Bioeng., 61:33-45 (1998).

Brown, et al, "Conformational studies of 5'=deoxyandenosyl-13-epicobalamin, a coenzymatically active structural analog of coenzyme B12", Polyhedron, 17:2213 (1998).

Brown and Burlington, "Penetration of host cell membranes by adenovirus 2", J. Virology, 12:386-396 (1973).

Brown and Zou, "Thermolysis of coenzymes B12 at physiological temperatures: activation parameters for cobalt-carbon bond homolysis and a quantitative analysis of the perturbation of the homolysis equilibrium by the ribonucleoside triphosphate reductase from *Lactobacillus leichmannii*", J. lnorg. Biochem., 77:185-195 (1999).

Brunger, et al., "Cyrstallography and NMR system: a new software suite for macromolecular structure determination". Acta Crystallogr., D 54:905-921 (1998).

Buc, et al., "Enzymatic and physiological properties of the tungsten-substituted molybdenum TMAO reductase from *Escherichia coli*", Mol. Microbiol., 32:159-68 (1999).

Bugg, et al., "From peptidoglycan to glycoproteins: common features of lipd-linked oligosaccharide biosynthesis", FEMS Microbiol. Lett., 119:255-262 (1994).

Bunka and Stockley, "Aptamers come of age-at last", Nat. Rev. aMicrobiol., 4:588-96 (2006).
Buratowski, "Connections between mRNA 3\ end processinf and transcription termination", Curr. Opin. Cell Biol., 17:257-61 (2005).
Burgin, et al., "Chemically modified hammerhead ribozymes with imporved catalytic rates". Biochemistry, 35:14090-14097 (1996).
Burke, et al. "Allosteric hammerhead ribozyme TRAPs", Biochemistry, 41:6588-6594 (2002).
Cadwell and Joyce, "Mutagenic PCR", PCR methods Appl., 3(6): S136-140 (1994).
Caillaud, "Adenoviral vector as a gene delivery system into cultured rat neuronal and glial cells", Eur. J. Neuroscience, 5:1287-1291 (1993).
Cameron, et al., "RNA secondary structure regulates the translation of sxy and competence development in Haemophilus influenzae", Nucleic Acids Res., 36:10-20 (2008).
Canny, et al., "Fast cleavage kinetics of a natural hammerhead ribozyme", J. Am. Chem. Soc., 126:10848-10849 (2004).
Caruthers, et al., "Chemical synthesis of deooxyoligonucleotides and deoxyoligonucleotide analogs", Methods Enzymol., 2111:3-19 (1992).
Castanotto, et al., "Intracellular expression and function of antisense catalytic RNAs", Methods Enzymol., 313:401-20 (2000).
Cate, et al., "RNA tertiary structure mediation by adenosine platforms", Science, 273: 1696-1699 (1996).
Cazzonelli and Velten, "Construction and testing of an intron-containing luciferase reporter gene from Renilla reniformis", Plant Mol. Biol. Rep., 21:271-80 (2003).
Cech, et al., "In vitro splicing of the ribosomal RNA precursor of Tetrahymena: involvement of a guanosine nucleotide in the excision of the intervening sequence", Cell, 3 (Pt2):487-96 (1981).
Cech, "Ribozyme engineering", Current Opinion in Structural Biology, 2:605-609 (1992).
Cech, "Ribozymes and their medical implications", JAMA, 260:3030-34 (1988).
Cech and Golden, "Building a catalytic active site using only RNA", In: The RNA World, Second Edition, 321-350 (1999).
Chan, et al., "Structural basis of activity and allosteric control of diguanylate cyclase", PNAS, 101:17084-9 (2004).
Chan, et al., "Structure of a hyperthermophilic tungstopterin enzyme, aldehyde ferredoxin oxidoreductase", Science, 267:1463-69 (1995).
Chardonnet and Dales, "Early events in the interaction of adenoviruses with HeLa cells. I. Penetration of type 5 and intracellular release of the DNA genome", Virology, 40 (3): 462-477 (1970).
Chartrand, et al., "An oligodeoxyribonucleotide that supoprts catalytic activity in the hammerhead ribozyme domain", Nucleic Acid Res., 23(20):4092-4096 (1995).
Cheah, et al., "Control of alternative RNA splicing and gene expression by eukaryotic riboswitches", Nature, 447(7143:497-500 (2007).
Chee, et al., "Accessing genetic information with high-density DNA arrays," Science, 274:610-614, 1996.
Chen, et al., "Multitarget-ribozyme directed to cleave at up to nine highly conserved HIV-1 env RNA regions inhibits HIV-1 replication-potential effectiveness against most presently sequenced HIV-1 isolates", Nucleic Acids Res., 20:4581-4589 (1992).
Chen, et al., "Structure-based discovery of ligands targeted to the RNA double Helix", Biochemistry, 36:11402-407 (1997).
Choi and Zalkin, "Stuructural characterization and corepressor binding of the *Escherichia coli* purine repressor", J. Bacteriol., 174:6207-6214 (1992).
Chowira, et al., "In vitro and in vivo comparison of hammerhead, hairpin and hepatitis delta virus self-processing ribozyme cassettes", J. Biol. Chem., 269:25856-25864 (1994).
Chowira and Burke, "Extensive phophorothioate sustitution yields highly active and nuclease-resitant hairpin ribozymes", Nucleic Acids Res., 20:2835-2840 (1994).
Christiansen, et al., "Xanthine metabolism in *Bacillus subtilis*: characterization of the xpt-pbuX operon and evidence for purin—and nitrogen—controlled expression of genes involved in the xanthine salvage and catabolism", J. Bacteriol, 179:2540-2550 (1997).
Christoffersaen and Marr, "Riobzymes as human therapeutic agents", J. Med. Chem, 38:2023-2037 (1995).

Clarke, et al, The structure of the ferric siderophore binding protein FhuD complexed with gallichrome, Nat. Struct. Biol., 7:287-91 (2000).
Claverie, Fewer genes, more encoding RNA, Science, 309:1529-30 (2005).
Cload and Schepartz, "Polyether tethered olignucleotide probes", J. Amer. Chem. Soc., 113: 6324-6326 (1991).
Clough and Bent, "Floral did, a simplified method for agrobacterium-mediated transformation of *Arabidopsis thaliana*", Plant J., 16:735-43 (1998).
Cochrane, et al., "Structural investigation of the GlmS ribozyme bound to its catalytic cofactor", Chem Biol., 14:97-105 (2007).
Collins, et al., "The cell cycle and cancer," Proc. Natl. Acad. Sci. USA, 94 (7)2776-2778 (1997).
Collins and Olive, "Reaction conditions and kinetics of self-cleavage of a ribozyme derived from Neurospora VS RNA", Biochem., 32(11):2795-2799 (1993).
Connelly and Manley, "A functional mRNA polyadenylation signal is required for transcription termination y RNA polymerase II", Genes Dev., 2:440-52 (1988).
Coppins, et al., "The intricate world of riboswitches", Curr. Opin. Microbiol., 10:176-181 (2007).
Corbino, et al. Evidence for a second class of S-adenosylmethiothine riboswitches and other regulatory RNA motifs in alpha-proteobacteria, Genome Biol., 6A:R70 (2005).
Cornell, et al., "A 2nd generation force0-field for the simulation of proteins, nucleic acids, and organic molecules", J. Am. Chem. Soc., 117:5179-5195 (1995).
Correll, et al., "The common and the disticntive features of the bulged-G motif based on a 1.04 ú resolution RNA structure", Nucleic Acids Res., 31:6806-6818 (2003).
Costa and Michel, "Frequent use of the same tertiary motif by srlf-folding RNAs", EMBRO J., 14:1276-85 (1995).
Costa and Michel, "Rules for RNA recognition of GNRA tetraloops deduced by in vitro selection: comparison with in vivo evolution", EMBRO J., 16:3289-3302 (1997).
Couture and Stinchcomb, "Anti-gene therapy: the use of ribozymes to prohibit gene function", Trends in Genetics, 12:510-515 (1996).
Coventry, et al., "MSARI: multiple sequence alignments for statistical detection of RNA secondary structure", Proceedings of the Nat. Aca. of Science, 101:12102-07 (2004).
Cromie, et al., "An RNA sensor for intracellular Mg(2+)", Cell, 125:71-84 (2006).
Cuenoud and Szostak, "A DNA metalloenzyme with DNA ligase activity", Nature, 375: 611-614 (1995).
Czechoeski, et al., "Genome-wide identification and testing of superior reference genes for transcript normalization in arabidopsis", Plant Physiol., 139:5-17 (2005).
Dai, et al., "Cleavage of an amide bond by a ribozyme", Science, 267(5195): 237-40 (1995).
Daiger, http://www.sph.uth.tmc.edu/retnet/help.htm.
Das, et al., "SAFA: Semi-automated footprinting and analysis software for high-thoughput quanitification of nucleic acid footprinting experiments", RNA-a publication of the RNA Soc., 11:344-54 (2005).
Dauter, et al., "Jolly SAD", Acta Crystallogr Biol Crystallogr, 58:494-506 (2002).
Davidson, et al., "Overproduction of polyomavirus middle T antigen in mammalian cells through the use of an adenovirus vector", J. Virology, 61:1226-1239 (1987).
Dayhoff, et al., "Protin superfamilies", Atlas of Protein Sequence and Structure, 5:2 (1976).
De La Pena, et al., "Peripheral regions of natural hammerhead ribozymes greatly increase their self-cleavage activity", EMBO J., 22:5561-5570 (2003).
Della Ragione, et al., "*Escherichia coil* S-adenosylhomocysteine/ 5\~methylthiaoadenosine nucleosidase, purification, substrate specificity and mechanism of action", Biochem. J., 232:335-41 (1985).
Desai et al., "Genetic screens and selections for small molecules based on a synthetic riboswitch that activates protein translation". J. Am. Chem. Soc., 126:13247-13254 (2004).

Dewey and Kidder, "Partial purification and properties of as nucleoside hydrolase from crithidia", Arch. Biochem. Biophys., 157:380-87 (1973).

Dillon and Rosen, "A rapid method for the construction of synthetic genes using the polymerase chain-reaction", Biotechniques, 9:298-300 (1990).

Dock-Bregeon and Moras, "Conformation changes and dynamics of tRNAs: evidence from hydolysis patterns", Cold Spring Harbor Symp. Quant. Biol., 52: 113-121 (1987).

Doherty, et al., "A universal mode of helix packing in RNA", Nature Struct. Biol., 8: 339-343 (2001).

Dong, "An efficient asymmetric synthesis of L-±,É-diaminoalkanoic acids", Tetrahedron Left., 33:7725-7726 (1992).

Douce, et al., "The glycine decarboxylase system: a fascinating complex", Trends Plant Sci, 6:167 (2001).

Doudna, "Preparation of homogeneous ribozyme RNA for crystallization", Methods Mol Biol., 74:365-70 (1997).

Drenser, et al.,"Ribozyme-targeted destruction of RNAs associated with ADRP," Inv. Ophth. Vis. Sci., 39:681-689 (1998).

Dropulic, et al., "Functional characterization of a U5 Ribozyme: intracellular suppression of human immunodeficiency virus type 1 expression", J. Virol., 66:1432-41 (1992).

Durand, et al., "Circular dichrosim studies of an oligdeoxyribonucleotide containing a hairpin loop made of a hexaethylene glycol chain: conformation and stability", Nucleic Acids Res., 18:6353-6359 (1990).

Durand, et al., "vacC, a virulence-associated chromosomal locus of shigella flexneri, is homologous to tgt, a gene encoding tRNA-guanime transglycosylase Tgt) of *Escherichia coil* K-12", J. Bacteriol, 176:4627-34 (1994).

Dye and Proudfoot, "Multiple transcript cleavage precedes polymerase release in termination by RNA polymerase II", Cell, 105:669-81 (2001).

Ebbole and Sachs, "A rapid and simple method for isolation of neurospora crassa homokaryons using microconidia", Fungal Genet. Newsl., 37:17-18 (1990).

Ebbole and Zalkin, "Cloning and characterization of a 12-gene cluster from *Bacillus subtilis* encoding nine enzymes for de novo purine nucleotide synthesis", J. Biol. Chem., 262: 8274-8287 (1987).

Eddy, Infernal User\s Guide, (2005).

Eddy, "Infernal, version 0.55", Dept of Genetics, Washington Univ School of Medicine St. Louis Mo. (2003).

Eddy and Durbin, "RNA sequence analysis using covariance models", Nucleic Acids Res., 22:2079-88 (1994).

Edelstein, "Cooperative interactions of hemoglobin", Annu Rev Biochem., 44:209 (1975).

Edwards and Ferrè-D Amarè, "Crystal structures of the thi-box riboswitch bound to thiamine pyrophosphate analogs reveal adaptive RNA-small molecule recognition", Structure, 14:1459-68 (2006).

Egli, et al., "Atomic-resolution structure of the cellulose synthase regulator cyclic diguanylic acid", PNAS, 87:3235 (1990).

Eisen, et al., "Cluster analysis and display of genome-wide expression patterns," Proc. Nat'l Acad. Sci. USA, 95:14863-14868 (1998).

Eldridge, et al., "Empirical scoring functions: I. The development of a fast empirical scoring function to estimate the binding affinity of ligands in receptor complexes", J. Comput-Aided Mol. Des., 11:425-445 (1997).

Elroy-Stein and Moss, "Cytoplasmic expression system based on constitutive sythesis of bacteriophage T7 RNA polymerase in mammalian cells", PNAS, 87:6743-6747 (1990).

Emilsson and Breaker, "Deoxyribozymes. New Activitiies an dNew Applications", Cell. Mol. Life Sci., 59:596-607 (2002).

Englisch, et al., "Chemically Modified Oligonucleotides as Probes and Inhibitors", Angewandte Chemie International Edition, 30:613-629 (1991).

Epshtein, et al., "The riboswitch-mediated control of sulfur metabolism in bacteria",. PNAS, 100:5052-5056 (2003).

Famulok, "Molecular biology. RNAs turn on in tandem", Science, 306:233-34 (2004).

Famulok, "Oligonucleotide aptamers that recognize small molecules". Current Opinion in Sturctural Biologoy, 9:324 (1999).

Fan, et al., "Molecular recognition in the FMN-RNA aptamer complex", J. Mol. Biol. 258:480-500 (1996).

Faou and Tropschug, "A novel binding protein for a member of CyP40-type Cyclophilins, n crassa CyPBP37 a growth and thiamine regulated protein homolog to yeast Thi-4p", J. Mol. Biol., 33:831-844 (2003).

Faou and Tropschug, "Neurospora crassa CyPBP37, a cytosolic stress protein that is able to replace yeast Thi-4p function in the synthesis of vitamin b1", J. Mol. Biol., 344:1147-57 (2004).

Fasken and Corbett, "Process or perish, quality control in mRNA biogenesis", Nat Struct Mol Biol., 12:482-488 (2005).

Fedor and Uhlenbeck, "Substrate sequence effects on 'hammerhead' RNA catalytic efficiency," Proc. Nat'l Acad. Sci. USA, 87:1668-1672 (1990).

Fedor and Uhlenbeck, "Kinetics of intermolecular cleavage by hammerhead ribozymes", Biochemisty, 31:12042-12054 (1992).

Feig and Brooks, "Recent advances in the development and application of implicit solvent models in biomolecule simulations.", Curr. Opin. Sturct. Biol., 14:217-224 (2004).

Ferentz and Verdine, "Disulfide cross-linked oligonucleotides", J. Am. Chem. Soc., 113:4000-4002 (1991).

Ferguson, et al., "A novel strategy for selection of allosteric ribozymes yields RiboReporter sensors for caffeine and aspartame", Nucleic Acids Res., 32:1756-1766 (2004).

Fiers, et al., "Complete nucleotide sequence of SV40 DNA", Nature, 273:113 (1978).

Finn, et al., "Pfam:clans, webtools and services", Nucleic Acids Res., 24:247-51 (2006).

Flamm, et al., "Design of multi-stable RNA molecules", RNA, 7:254-265 (2001).

Flamm, et al., "RNA folding kinetics at elementary step resolution", RNA, 6:325-338 (2000).

Forster and Symons, "Self cleavage of plus and minus RNAs of a virusoid and structural moldel for the active sites", Cell, 49:211-220 (1987).

Foulkes and Sassone-Corsi, "More is better: activators and repressors from the same gene", Cell, 68:411 (1992).

Freier, et al., "Improved free-energy parameters for predictions of RNA duplex stability", PNAS, 83:9373-9377 (1986).

Frey, et al., "Mutations in the *Escherichia coli* fnr and tgt genes: control molybdate reductase activity and the cytochrome d complex by fnr", J. Bacteriol., 171:1524-30 (1989).

Frey, et al., "New function of vitamin B12 cobamide-dependent reduction of epoxyqueuosine to queuosine in tRNAs of *Escherichia coli* and salmonella typhimurium", J. Bacteriol., 170:2078-82 (1988).

Froehlich, et al., "Rhythmic binding of a white collar-containing complex to the frequency promoter is inhibited by frequency", PNAS, 100:5914-19 (2003).

Fuchs, et al., The S(MK) box is a new SAM-binding RNA for translational regulation of SAM synthesis, Nat Struct. Mol. Biol., 13:226-233 (2006).

Galagan, et al., "Sequencing of aspergillus nidulans and comparative analysis with A fumigatus and A oryzae", Nature, 438:1105-15 (2005).

Galperin, et al., "Novel domains of the prokaryotic two-component signal transduction systems", FEMS Microbiol. Lett, 203:11 (2001).

Gao and Huang, "Cytoplasmic expression of a reporter gene by co-delivery of T7 RNA polymerase and T7 promoter sequence with cationic liposomes", Nucleic Acids Res., 21: 2867-2872 (1993).

Garcia Martin, et al., "Metagenomic analysis of two enhanced biological phosphorus removal (EBPR) sludge communities", Natl. Biotechnol., 24:1263-69 (2006).

Gaur and Varshney, "Genetic analysis identifies a function for the queC(ybaX) gene product at an initial step in the queuosine iosynthetic pathway in *Eschrichia coli*", J. Bacteriol., 187:6893-6901 (2005).

Gelford, et al., "A conserved RNA structure element involved in the regulation of bacterial riboflavin synthesis genes", Trends Gen., 15:439-442 (1999).

Gerstein, et al. "Volume changes in protein evolution", J. Mol. Biol., 236:1067-78 (1994).

Gewirtz, et al., "Facilitating oligonucleotide delivery: helping antisense deliver on its promise", PNAS, 93:3161-3163 (1996).

Geyer and Sen, "Evidence for the metal cofactor independence of an RNA phophodiester cleaving DNA enzyme", Chem. Biol., 4:579-593 (1997).

Gilbert, et al., "Thermodynamic and kinetic characterization of ligand binding to the purine riboswitch aptamer domain", J. Mol. Biol., 359:754-68 (2006).

Gill, et al., "Metagenomic analysis of the human distal gut microbiome", Science, 312:1355 (2006).

Gohlke, et al., "Knowledge based scoring function to predict protein-ligand interactions", J. Mol. Biol., 295:337-356 (2000).

Gohlke and Klebe, "Apporaches to the description and prediction of the biding affinity of small-molecule ligands to macromolecular receptors", Angew. Chem. Int. Ed., 41: 2644-4647 (2002).

Gold, et al, "From oligonucleotide shapes to genomic SELEX: novel biological regulatory loops", PNAS, 94:59-64 (1997).

Gold, et al., "Diversity of oligonucleotide functions", Annual Review of Biochemistry, 64:763-797 (1995).

Gold, et al., "SELEX and the evolution of genomes", Curr. Opin. Gen. Dev., 7:848-851 (1997).

Gomez-Foix, et al., "Adenovirus mediated transfer of the muscle glycogen phosphorylase gene into hepatocytes confers altered regulation of glycogen metabolism", J. Biol. Chem., 267:25129-25134 (1992).

Gooch, et al., "Fully codon-optimized luciferase uncovers novel temperature characteristics of the neurospora clock", Eularyotic Cell, 7(1):28-37 (2008).

Good, et al, "Expression of small, therapeutic RNAs in human nuclei", Gene Therapy, 4:45-54 (1997).

Gottesman, "Stealth regulation: biological circuits with small RNA switches", Genes Dev., 16:2829-2842 (2002).

Grate, et al., "Inducible regulation of the S. Cerevisiae cell cycle mediated by an RNA aptamer-ligand complex", Bioorg. Med. Chem., 9:2565-2570 (2001).

Graveley, "Alternative splicing: increasing diversity in the proteomic world", Trends Genet., 17:100 (2001).

Greenway, et al., "Human cytomegalovirus DNA: BamHI, EcoRI and Pstl restriction endonuclease cleavage maps", Gene, 18:355-360 (1982).

Griffiths-Jones, et al., "Rfam:annotating non-coding RNAs in complete genomes", Nucleic Acids Res., 33:121-24 (2005a).

Griffiths-Jones, "RALES-RNA alignment editor in ermacs", Bioinformatics, 21:257-59 (2005).

Gruden and Shanmugam, "Molybdate transport and regulation in bacteria", Arch. Microbiol., 168:345-54 (1997).

Grunden, et al., "An analysis of the binding of repressor proten ModE to modABCD (molybdate transport) operator/promoter DN of Escherichia coli", J. Biol. Chem., 274:24305-15 (1999).

Grundy, et al., tRNA-mediated transcription antitermination in vitro: codon-anticodon pairing independent of the ribosome. PNAS, 99, 11121 (2002).

Grundy, et al., "The L box reguion: Lysine sensing by leader RNAs of bacterial lysine biosynthesis genes", Nucleic Acids Res., 100:12057-12062 (2003).

Grundy and Henkin, "The S box regulon: a new global transcription termination control sytem for methionine and cysteine biosynthesis genes in Gram-positive bacteria", Molecular Microbiology, 30:737 (1998).

Grundy and Henkin, "The T box and S box transcription termination control systems", Frontiers Biosci., 8:020 (2003).

Guerout-Fleury, et al, "Plasmids for ectopic integration into Bacillus subtilis", Gene, 180:57-61 (1996).

Guerrier-Takada, et al. "The RNA Moiety of ribonuclease P is the catalytic subunit of the enzyme", Cell, 35:849 (1983).

Guo and Collins, "Efficient trans-cleavage of a stem-loop RNA substrate by a ribozyme derived from Neuorspora VS RNA", EMBO J., 14:368-376 (1995).

Guo et al., "Direct fluorescence analysis of genetic polymorphisms by hybridization with oligonucleotide arrays on glass supports", Nucleic Acids Res., 22: 5456-5465 (1994).

Gusarov and Nudler, "The mechanism of intrinsic transcription termination", Molecular Cell, 3:495-504 (1999).

Guzman, et al., "Efficient gene trasnfer into myocardium by direct injection of adenovirus vectors", Circulation Research, 73:1201-1207 (1993).

Guzman, et al., "Tight regulation modulation and high-expression by vectors containing the arabinose Pbad promoter", J. Bacteriol., 177:4121-30 (1995).

Gündüz and Katze, "Salvage of the nucleic acid base queuine from queuine-containing tRNA by animal cells", Biochem. Biophys. Res. Commun., 109:159-67 (1982).

Gunduz and Katze, "Queuine salvage in mammalian cells, evidence that queuine is generated from qwueuosine 5\-phosphate", J. Biol. Chem., 259:1110-13 (1984).

Haj-Ahmad, et al., "Development of a helper-independent human adenovirus vector and its use in the transfer of the herpes simplex virus thymidine kinase gene", J. Virology, 57: 267-274 (1986).

Hamaguchi, et al. "Aptamer beacons for the detection of proteins", Anal. Biochem., 294:126-131 (2001).

Hammann, et al., "Length variation of helix II in a hammerhead ribozyme and its influence on cleavage activity", Antisense and Nucleic Acid Drug Dev., 9:25-31 (1999).

Hampel, et al. "Hairpin catalytic RNA model: evidence for helices and sequence requirement for substrate", RNA Nucl. Acids Res., 18:299 (1990).

Hampel, et al. "RNA catalytic properties of the minimum (−)s TRSV sequence", Biochem., 28:4929 (1989).

Hannon, "RNA Interference", Nature, 418:244-251 (2002).

Harada and Nishimura, "Possible anticodon sequences of tRNA hls, tRNA asn and tRN asp from Escherichia coli B auniversal presence of nucleoside Q in the first position of the anticodons of these transfer ribonucleic acids", Biochemistry, 11:301-08 (1972).

Harvey, et al., "Inhibition of translation by RNA-small molecule interactions", RNA, 8:452-463 (2002).

He and Hannon, "microRNAs: small RNAs with a big role in gene regulation", Nature Reviews Genetics, 5:522-31 (2004).

Hendrix, et al., "RNA structural motifs :building blocks of a modular biomolecule", Q Rev. Biophys., 38:221-43 (2005).

Hendry, et al., "Using linkers to investigate the spatial separation of the conserved nucleotides A9 and G12 in the hammerhead ribozyme", Biochimica et Biophysica acta, 1219: 405-412 (1994).

Henegariu, et al., "Custom fluorescent nucleotide synthesis as an alternative method for nucleic acid labeling", Nature Biotechnology, 18:345-348 (2000).

Henkin, "Transcription termination control in bacteria", Current Opinion in Microbiology, 3:149 (2000).

Henkin, "tRNA directed transcription antitermination", Mol. Microbiol. 3:381-387 (1994).

Henkin and Yanofsky, "Regulation by transcription attenuation in bacteria: how RNA provides instructions for transcription termination/antitermination decisions", Bioessays, 24:700 (2002).

Hermann and Patel, "Adaptive recognition by nucleic acid aptamers", Science, 287:820-825 (2000).

Hermes, et al., "Influence of an altered methylation potential on mRNAS methylation and gene expression in HepG2 cells", Experimental Cell Res., 294:325-34 (2004).

Hertel, et al., "Numbering system for the hammerhead", Nucleic Acids. Res., 20: 3252 (1992).

Hesselberth, et al., "Simultaneous detection of diverse analytes with an aptazyme ligase array", Anal. Biochem., 312:106-112 (2003).

Hesselberth and Ellington, "A (ribo) switch in the paradigms of genetic regulation", Nature Struct. Biol., 9:891-893 (2002).

Heus and Pardi, "Structural features that give rise to the unusual stability of RNA hairpins containing GNRA loops", Science, 253:191-94 (1991).

Higgins, et al., "Peptide transport in bacteria", Methods Enzymol, 125:365-77 (1986).

Hirsch, et al., "Identification of positive and negative regulatory elements governing cell-type-specific expression of the neural-cell-adhesion-molecule gene," Mol. Cell. Biol., 10:1959 (1990).

Hofacker, et al. "Fast folding and comparison of RNA secondary structures", Monatsh. Chem., 125:167-188 (1994).

Hofacker, "Vienna RNA secondary structure server", Nucleic Acids Res., 31:3429-3431 (2003).

Hourman, et al., "Transcriptional antitermination in the bgl operon of *E. coli* is modulation by a specific RNA binding protein", Cell, 62:1153-63 (1990).

Hoy, et al., "Bromodeoxyuridine/DNA analysis of replication in CHO cells after exposure to UV light", Mutation Research, 290:217-230 (1993).

Hunziker, et al., Nucleic Acid analogues: synthesis and properties, in Modern synthetic methods, VCH, 331-417 (1995).

Hurt, et al., "Site-specific modification of shigella flexneir virF mRNA by tRNA-guanine transglycosylase in vitro", Nucleic Acids Res., 35:4905-13 (2007).

Hutton, et al., "Inhibitors of lysine biosynthesis as antibacterial agents", Mini. Rev. Med. Chem, 3:115-127 (2003).

Höfgen and Willmitzer, "Transgenic potato plants depleted for the major tuber protein patatin via expression o antisense RNA", Plant Sci., 87-45-54 (1992).

Iobbi-Nivol, et al., "The mob locus of *Escherichia coil* K 12 reuired for molybdenum cofactor biosynthesis is expressed at very low levels", Microbiology, 141:1663-71 (1995).

Isaacs, et al. "Engineered riboregulators enable post-transcriptional control of gene expression", Nat. Biotechnol., 22:841-847 (2004).

Ishiwata, et al., "Physical-chemistry characteristics and biodistribution of poly(ethylene glycol) coated liposmes using poly (oxyethylene) coholesteryl ether", Chem. Pharm. Bull., 43:1005-1011 (1995).

Iwata-Reuyl, "Biosynthesis of the 7-deazaguanosine hypermodified nucleosides of transfer RNA", Bioorg. Chem., 31:24-43 (2003).

Iyer, et al., "The prokaryotic antecedents of the ubiquitin-signaling system and the early evolution of ubiquitin-like-$^2$-grasp domains", Genome Biol., 7a;R60 (2006).

Izant and Weintraub, "Constitutive and conditional suppression of exogenous and endogenous genes by anti-sense RNA", Science, 229:345-352 (1985).

Jadhav and Yarus, "Coenzymes as coribozymes", Biochimie, 84:877-888 (2002).

Jaeger, et al., "Predicting optimal and suboptimal secondary structure for RNA", Methods Enzymol., 183:281-306 (1990).

Jaeger,et al., "Improved predictions of secondary structures for RNA", PNAS, 86: 7706-7710 (1989).

Jansen, et al., "Backbone and nucleobase contacts to glucosamine-6-phosphate in the glmS ribozyme", Nat. Struct. Mol. Biol., 13:517-523 (2006).

Jarmer, et al., "Transcriptome analysis documents induced competence of *Bacillus subtilis* during nitrogen limiting conditions", FEMS Microbiol. Lett., 206:197 (2002).

Jaschke, et al., "Automated incorporation of polyethylene gycol into synthetic oligonucleotides", Tetrahedron Letters, 34:301-304 (1993).

Jeffares, et al., "Relics from the RNA world", J. Mol. Evol., 46:18-36 (1998).

Jefferies and Symons, "A catalytic 13-mer ribozyme", Nucleic Acids Res., 17: 1371-1377 (1989).

Jenal, "Mechanisms of cyclic-di-GMP signaling in bacteria", Annu Rev. Genet, 40:385-407 (2006).

Jenison, et al., "High resolution molecular dicrimination by RNA", Science, 263: 1425-1429 (1994).

Jenne, et al., "A novel ribozyme with ester transferase activity", Chem Biol., 5 (1) 23-34 (1998).

Jiang and Wu, "Alternative splicing and programmed cell death", Prod. Soc. Exp. Biol. Med., 220:64 (1999).

Johansen, et al, "Definition of a second *Bacillus subtilis* pur regulon comprins the pur and xpt-pbuX operons plus pbuG, nupG (yxjA), and pbuE (ydhL)", J. Bacteria, 185:5200-5209 (2003).

Johnson, et al., "Identification of molybdopterin as the organic component of the tungsten cofactor in four enzymes from hyperthermophilic archaea", J. Bio. Chem., 268:4848-52 (1993).

Johnson, et al., "Molybdenum cofactor biosynthesis in *Escherichia coli*, requiremenr of the chlB gene product for the formation of molybdopterin guanine dinucleotide", J. Biol. Chem., 266:12140-45 (1991).

Jones, et al., "Improved methods for building protein models in electorn density maps and the location of errors in these models", Acta Crystallogr, A 47 (pt 2):110-9 (1991).

Jones, et al., "Moleuclar recongition of recpetor sites using a genetic algorithem with a description of desolvation", J. Mol. Biol., 245:43-53 (1995).

Jose, et al., "Cooperative binding of effectors by an allosteric ribozyme", Nucleic Acids Res., 29:1631-1637 (2001).

Joseph, et al., "Rapid orientated cloning in a shuttle vector allowing modulated gene expression in *Bacillus subtilis*", FEMS Microbiol. Lett., 205:91 (2001).

Joseph and Burke, "Optimization of an anti-HIV hairpin ribozyme by in vitro selection", J. Biol. Chem., 268:24515-24518 (1993).

Joyce, et al., "Amplification, mutation and selection of catalytic RNA", Gene, 82:83-87 (1989).

Joyce, et al., "Directed molecular evolution", Scientific American, 267:90-97 (1992).

Joyce, "RNA evolution and the origins of life", Nature, 338:217-244 (1989).

Joyce, "The antiquity of RNA-based evolution", Nature, 418:214-221 (2002).

Kanehisa, et al., "From genomics to chemical genomics: new developments in KEGG", Nucleic Acids Res., 34:D354-57 (2006).

Kasjani-Sabet, et al., "Reversal of the malignant phenotype by an anti-ras ribozyme", Antisense Research & Development, 2:3-15 (1992).

Kawasaki et al., "Thiamine regulatory mutants in *Escherichia coli*", J. Biochem. (Tokyo), 65:417-25 (1969).

Kerkhof, "A comparison of substrates for quantifying the signal from a nonradiolabeled DNA probe", Anal. Biochem., 205:359-364 (1992).

Kertesz, et al., "Both introns and long 3\-UTRs operate as cis-acting elements to trigger nonsense-mediated decay in plants", Nucleic Acids Res., 34:6147-57 (2006).

Khrapko, et al., "Hybridization of Dna with oligonucleotides immobilized in a gel: a convenient method for recording single base replacements", Mol Biol (Mosk) (USSR), 25:718-730 (1991).

Khvorova, et al., "Sequence elements outside the hammerhead ribozyme catalytic core enable intracellular activity", Nature Struct. Biol., 10:708-712 (2003).

Kief and Warner, "Coordinate control of syntheses of ribosomal ribonucleic acid and ribosomal proteins during nutritional shift-up in *Saccharomyces cerevisiae*," Mol. Cell Biol., 1:1007-1015, 1981.

Kieft and Batey, "Ageneral method for rapid and nondenatureing purification of RNAs", RNA, 10:988-995 (2004).

Kieser, et al., Practical streptomyces genetics, The John Innes Foundation, Norwich UK (2000).

Kiga, et al., "An RNA aptamer to the xanthine/guanine base with a distinctive mode of purine recognition", Nucleic Acids Res., 26: 1755-1760 (1998).

Kikuchi, "The glycine cleavage system: composition, reaction mechanism, and physiological significance", Mol Cell Biochem., 1:169 (1973).

Kil, et al., "Riboflavin operon of *Bacillus subtilis*: unusual symmetric arrangement of the regulatory region", Molecular & General Genetics, 233:483 (1992).

Kim, et al., "Accumulation of S-adenosyl-L-methionine enhances production of actinorhodin but inhibits sporulaton in streptomyces licidans TK23", J. Bacteriol., 185:592-600 (2003).

Kim, et al., "An artificial riboswitch for controlling pre-mRNA splicing", RNA, 11 (11):1667-77 (2005).

Kim, et al., "Two putative c-type multiheme cytochromes required for the expression of OmcB, an outer membrane protein essential for optimal Fe(III) reduction in geobacter sulfurreducens", J. Bacterial., 188:3138-42 (2006).

Kim and Cech, "Three-dimensional model of the active site of the self-splicing rRNA precursor of Tetrahymena", PNAS, 84:8788-92 (1987).

Kima and Nam, "Genomics of microRNA", Trends Genet., 22:165-73 (2006).

Kim, et al, "A colonization factor links vibrio cholerae environmental survival and human infection", Nature, 438:863-66 (2005).

Kirschenbaum, et al., "Highly efficient gene transfer into adult ventricular myocytes by recombinant adenovirus", J. Clin. Invest., 92:381-387 (1993).

Klein, et al., "Structural basis of blmS ribozyme activation by glucosamine-6-phosphate", Science, 313:1752-1756 (2006).
Klein and Eddy, "Research: finding homologs of single structured RNA sequences", BMC Bioinfotmatics, 4:44 (2003).
Klein and Ferre-D\Amare, "Structural basis of glmS ribozyme activation by glucosamine-6 phosphate", Science, 313:1752-56 (2006).
Kletzin and Adams, "Tungsten in biological systems", FEMS Microbiol. Rev., 18:5-63 (1996).
Kobayashi, et al., "Essential *Bacillus subtilis* genes", Proc. Natl. Acad. Sci. USA, 100: 4678-4683 (2003).
Kochhar and Paulus, "Lysine-induced premature transcription termination in the lysC operon of *Bacillus subtilis*", Microbiol., 142;1635-1639 (1996).
Koizumi, et al., "Allosteric selection of ribozymes that repond to the second messengers cGMP and cAMP", Nature Struct. Biol., 6:1062-1071 (1999).
Komatsu, et al., "Construction of new ribozymes requiring short regulator oligonucleotides as a cofactor", J. Mol. Biol., 299:1231-1243 (2000).
Krasilinkov, et al., Basis for structural diversity in homologous RNAs, Science, 306:104-07 (2004).
Kreneva, et al., "Inactivation of the ypaA gene in *Bacillus subtilis*; analysis of the resulting phenotypic expression", Gentika, 36: 972-74 (2000).
Kreneva, et al. "Study of the phenotypic occurrence of ura gene inactivation in *Bacillus subtilis*", Genetika, 36(8):116-68 (2000) (Abstract only).
Kubodera, et al, "Thiamine-regulated gene expression of *Aspergillus oryzae* thiA requires splicing of the intron containing a riboswitch-like domain in the 5'UTR", FEBS Lett, 555:516-520 (2003).
Kuchino, et al., "Biosynthesis of the modified nucleoside Q in transfer RNA", Nucleic Acids Res., 3:393-98 (1976).
Kumar and Ellington, "Artificial evolution and natural ribozymes", FASEB J, 9:1183-1195 (1995).
Kunkel, et al., Rapid and effcient site-specific mutagenesis without phenotypic selection. Methods Enzymol., 154: 367-82 (1987).
L'Huillier., et al., "Cytoplasmic delivery of ribozymes leads to efficient redution in alpha-latalbumin mRNA levels in C1271 mouse", EMBO J., 11:4411-4418 (1992).
Laimins, et al., Osmotic control of kdp operon expression in *Escherichia coli*, PNAS, 78: 464-8 (1981).
Lake, et al., "The crystal structure of the *Escherichia coli* MobA protein provides insight into molybdopterin guanine dinucleotide biosynthesis", J. Biol. Chem., 275:40211-17 (2000).
Landick, et al., "Quantitative analysis of transcriptional pausing by *Escherichia coli* RNA polymerase: his leader pause site as paradigm", Methods Enzymol., 274:334-353 (1996).
Langer, et al., "Enzymatic synthesis of biotin-labeled polynucleotides: novel nucleic acid affinity probes", PNAS, 78:6633 (1981).
Lasic and Needham, "The stealth liposome: a protypcial biomaterial", Chem. Rev., 95:2601-2627 (1995).
Lasic and Paphajopoulos, "Liposomes revisited", Science, 267:1275-76 (1995).
Lauhon and Szostak, "RNA aptamers that bind flavin and nicotinamide redox cofactors", Journal of the American Chemical Society, 117: 1246 (1995).
Lazazzera et al., "An exported peptide functions intracellularly to contribute to cell density signalling in *B. subtilis*", Cell, 89:917-925 (1997).
Le Gal La Salle, et al., "An adenovirus vector for gene transfer into neurons and glia in the brain", Science, 259:988-990 (1993).
Lea, et al, "Turning on\ riboswitches to their antibacterial potential", Nature, 3:16-17 (2007).
Leavitt and Freire, "Direct measurement of protein biding energitics by isothermal titration calorimetry", Curr Opin Struct Biol, 11:560-6 (2001).
Lee, et al., "A cyclic-di-GMP receptor required for bacterial exopolysaccharide production", Mol. Microbial., 65:1474-84 (2007).
Lee, et al., "RNA expression analysis using an antisense *Bacillus subtilis* genome array", J. of Bacteriology, 183:7371 (2001).

Lemay, et al., "Folding of the adenine riboswitch", Chem. Biol., 13:857-68 (2006).
Leontis and Westhof, "A common motif organizes the structure of multi-helix loops in 16S and 23S ribosomal RNAs", Mol. Biol. 283:571-583 (1998).
Leulliot and Varani, "Current topics in RNA-protein recognition: control of specificity and biological function through induced fit and conformational capture", Biochemistry, 40:7947-7956 (2001).
Lewin, et al., "Ribozyme gene therapy: applications for molecular medicine", Trends Mol. Med., 7 221-228 (2001).
Li and Breaker, "Deoxyribozymes: new players in the ancient game of biocatalysts", Curr. Opin. Struct. Biol., 9:315-323 (1999).
Li and Breaker, "Kinetics of RNA degradation by specific base catalysts of transesterification involivng the 2'-hydroxyl group", J. Am. chem. Soc., 121:5364-5372 (1999).
Li and Breaker, "In vitro Selection of Kinase and Ligase Deoxyribozymes", Methods, 23:179-190 (2001).
Li and Sen, "A catalytic DNA for porphyrin metallation", Nat. Struct. Biol., 3:743-747 (1996).
Liang and Pardee, "Differential display. A general protocol," Methods Mol. Biol., 10:261-67 (1998).
Liao and Hsen, "Analysis of the regulatory region of the lysC gene of *Escherichia coli*", FEMS Microbial Left., 168:31-36 (1998).
Lieber, et al., "A mutant T7 phage promoter is specifically transcribed by T7-RNA polymerase in mammalian cells", Eur J Biochem, 217:387-94 (1993).
Lieber, et al. "Stable high level gene expression in mammalian cells by T7 phage RNA polymerase", Methods Enzymol., 217: 47-66 (1993).
Lillo, et al., "Comparative genomics study of inverted repeats in bacteria". Bioinformatics, 18:971 (2002).
Lim, et al., "Characteristics of ligand recognition by a glmS self-cleaving ribozyme", Angew. Chem. Int., 45:6689-93 (2006a).
Lim, et al., "Cyclic-diGMP signal transduction systems in *Vibrio cholerae*: modulation of rugosity and biofilm formation", Mol. Microbiol., 60:331-48 (2006c).
Lim, et al., "Molecular-recognition characteristics of SAM-binding riboswitches", Angewandte Chem. Int. Ed., 45: 964-968 (2006b).
Limbach, et al., "Summary: the modified nucleosides of RNA", Nucleic Acids Res., 22(12):2183-2196 (1994).
Lisziewicz, et al., "Inhibition of human immunodeficiency virus type-1 replication by regulated expression of a polymeric tat activation response RNA decoy as a strategy for gene therapy in AIDS", PNAS, 90:8000-8004 (1993).
Lisziewicz, et al., "Long-term treatment of human immunodeficiency virus-infected cells with antisense oligonucleotide phosphorothioates PNAS, 90:3860-64 (1993).
Liu, et al., "The RNA molecule CsrB binds to the global regulatory protein CsrA and antagonizes its activity in *Escherichia coli*", J. Biol. Chem., 272:17502-510 (1997).
Liu et al., Cationic liposome mediated intravenous gene delivery. J. Biol. Chem. 270(42): 24864-24870 (1995).
Logan, et al., "A poly(A) addition site and a downstream termination region are required for efficient cessation of transcription by RNA polymerase II in the mouse beta maj-globin gene", PNAS, 84:8308-10 (1987).
Lohse, et al. "Ribozyme-catalysed amino-acid transfer reactions", Nature, 30:381(6581):442-4 (1996).
Long and Uhlenback, "Kinetic characterization of intramolecular and intermolecular hammerhead RNAs with stem II deletions", PNAS, 91:6977-6981 (1994).
Loros and Dunlap, "Neurospora crassa clock-controlled genes are regulated at the level of transcription", Mol. Cell Biol., 11:558-563 (1991).
Lu, et al., "Fine-structure mapping of cis-acting control sites in the lysC operon of *Bacillus subtilis*", FEMS Microbiol. Lett., 92:23-27 (1992).
Lu, et al., "Identification of aecA mutations in *Bacillus sbutilis* as nucleotide substitutions in the untranslated leader region of the aspartokinase II operon", J. Gen. Microbiol., 137:1135-1141 (1991).
Lundrigan, et al., "Transcribed sequences of the *Escherichia coil* btuB gene control its expressiona nd regulation by vitamin B12", PNAS, 88:1479-1483 (1991).

Lundrigan and Kadner, "Altered cobalamin metabolism in *Escherichia coli* btuR mutants affects btuB gene regulation", J. Bacteriol., 171:154-161 (1989).
Lusky, et al., "Bovine pailloma virus contains an activator of gene expression at the distal end of the early transcription unit", Mol. Cell Bio., 3:1108 (1983).
Ma, et al, "Design and synthesis of RNA miniduplexes via a sythetic linker approach", Biochemistry, 32:1751-1758 (1993).
Ma, et al., "Design and sythesis of RNA miniduplexes via a synthetic linker approach. 2. Generation of covalently closed, double stranded cyclic HIV-1 TAR RNA analogs with high tat-binding affinity", Nucleic Acids. Res., 21:2585-2589 (1993).
MacKerell, et al., "All-atom empirical potential for molecular modeling and dynamics studies of proteins", J. Phys. Chem. B., 102:3586-3616 (1998).
Mader, et al., "Transcriptome and proteome analysis of *Bacillus subtilis* gene expression modulated by amino acid availability", J. Bacteriol., 184:4288-4295 (2002).
Mager and Planta, "Coordinate expression of ribosomal protein genes in yeast as a function of cellular growth rate," Mol. Cell Biochem., 104:181-187 (1991).
Makdessi, et al., "Tungstate uptake by a highly specific ABC transporter in eubacterium acidaminophilum", J. Biol. Chem., 276:24557-64 (2001).
Makela, "Alternative forms of Max as enhancers or suppressors of Myc-ras cotransformation", Science, 256:373-77 (1992).
Mandal, et al., "Riboswitches control fundamental biochemical pathways in *Bacillus subtilis* and other bacteria", Cell, 113:577-86 (2003).
Mandal and Breaker, "Adenine riboswitches and gene activation by disruption of a transcription terminator", Nature Struct Mol Biol., 11:29-35 (2004).
Mandel, et al., "Gene regulation by riboswitches", Nature Rev Mol Cell Biol., 5:451-463, 2004.
Mandel, et al. "A Glycine-Dependent Riboswitch That Uses Cooperative Binding to Control Gene Expression", Science, 306:275-279 (2004).
Manoharan, "2'-carbohydrate modifications in antisense oligonucleotide therapy: importance of conformation, configuration, and conjunction", Beiochem Biophys. Acta, 1489(1): 117-130 (1999).
Mansilla, et al., "Transcriptional control of the sulfur-regulated cysH operon, containing genes involved in L-cysteine biosynthesis in *Bacillus subtilis*", J. Bacteriol, 182: 5885 (2000).
Marchler-Bauer, et al., "CDD: a consrrved domain database for protein classification", Nucleic Acids Res., 33:192-96 (2005).
Massie, et al, "Construction of a helper-free recombinant adenovirus that expresses polyomavirus large T antigen", Mol. Cell. Biol., 6:2872-2883 (1986).
Mathews, et al., "Expnaded sequence dependence of thermodynamic parameters imporves prediction of RNA secondary structure", J Mol. Biol., 288:911-940 (1999).
Matlin, et al., "Understanding alternative splicing: Towards a cellular code", Nature, 6:386-398 (2005).
Matthews and Nichols, "Lactose repressor protein: functional properties and structure", Prog. Nucleic Acids Res, Mol. Biol., 58:127-164 (1998).
Maundrell, "nmt1 of fission yeast, a highly expressed gene completely repressed by thiamine", J. Biol Chem., 265:10857-64 (1989).
Maupin-Furlow, et al., "Genetic analysis of the modABCD (molybdate transport) operon of *Escherichia coli*", J. Bacteriol., 177:4851-56 (1995).
Mayer, et al., "High-throughput-compatible assay for glmS riboswitch metabolite dependence", ChemBioChem, Bol., 7:602-604 (2006).
McCall, et al., "Minimal sequence requirements for ribozymes activity", PNAS, 89: 5710-5714 (1992).
McCarthy, et al., "Ligand requirements for glmS ribozyme self-cleavage", Chem. Biol., 12:1221-1226 (2005).
McCaskill, "The equilibrium partition function and base pair binding probabilities for RNA secondary structure", Biopolymers, 29:1109-1119 (1990).

McCauley, et al. "Aptamer-based biosensor arrays for detection and quantification of biological macromolecules", Anal. Biochem. 319:244-250 (2003).
McColl, et al., "Characterization and expression of the neurospora crassa nmt-1 gene", Curr. Genet., 44:216-223 (2003).
McConnell, et al, "Guanosine binding to the Tetrahymena ribozyme: thermodynamic coupling with oligonucleotide binding", PNAS, 90:8362-8366 (1993).
McCurdy, et al., "Deoxyoligonucleotides with inverted polarity: synthesis and use in triple-helix formation", Nucleosde & Nucleotides, 10:287-290 (1991).
McCutcheon and Eddy, "Computational identification of non-coding RNAs in *Saccharomyces cerevisiae* by comparative genomics", Nucleic Acids Res., 31:4119-28 (2003).
McDaniel, et al., "Transcription termination control of the S box system: direct measurement of S-adenosylmethionine by the leader RNA", PNAS, 100:3083-3088 (2003).
McGarry and Linquist, "Inhibition of heat shock protein synthesis by heat-inducible antisense RNA", PNAS, 83:399-403 (1986).
Mehta, et al., "Outer membrane c-type cytochromes required for Fe(III) and Mn (VI) oxide reduction in geobacter sulfurreducens", Appl. Eviron Microbiol., 71:8634-41 (2005).
Meibom, et al., "Chitin induces natural competence in vibro cholerae", Science, 310:1824-27 (2005).
Meibom, et al., "The vibrio cholerae chitin utilization program", PNAS, 101:2524-29 2004).
Meier, et al "Queuosine modification of the wobble base in tRNA HIS influences in viro decoding properties", EMBRO J., 4:823-27 (1985).
Meng, et al., "Ribozyme probe based on molecular beacon for real time monitoring of enzymatic cleavage process", Chinese Science Bull., 48 (23):2581-84 (2003).
Mesmaeker et at., "Novel backbone replacements for oligonucleotides", Am. Chem. Soc., 24-39 (1994).
Methe, et al., "Genome of geobacter sulfurreducens: metal reduction in subsurface environments", Science, 302:1967-69 (2003).
Michel and Westhof, "Modeling of the three-dimensional architecture of group I catalytic introns based on comparative sequence analysis", J. Mol. Biol., 216:585-610 (1990).
Michels and Pyle, "Converstaion of group II intron into a new multiple turnover ribozyme that selectively cleaves oligonucleotides: elucidation of reaction mechanism and structure/function relationships", Biochemistry, 34:3965-3977 (1995).
Migawa, et al., "A two step synthesis of the nucleoside Q precursor 2-amino-5-cyanopyrrolo[2,3-d]pyrimidine-4-one (preQ0)", Synth. Commun., 26:3317-22 (1996).
Milewski, et al., "Glucosamine-6-phosphate synthase—the multifacets enzyme", Biochim. Biophys. Acta 1597:173-192 (2002).
Miller, et al., Nucleoside hydrolases from trypanosome cruzi, J. Biol. Chem., 259:5073-77 (1984).
Miller, "In: A Short Course in Baceterial Genetics" (Cold Spring Harbor Laboratory Press, Cold Spring Harbor, NY) p. 72 (1992).
Milligan and Uhlenbeck, "Synthesis of small RNAs using T7 RNA polymerase", Methods Enzymol., 180:51-62 (1989).
Miranda-Rios, et al., "A conserved RNA structiure (thi box) is involved in regulation of thiamin biosynthetic gene expression in bacteria", PNAS, 98:9736-9741 (2001).
Miranda-Rios, et al., "the THI-box riboswitch or How RNA binds thiamin pyrophosphate", Structure Current Biology, 15(3):259-65 (2007).
Mironov, et al., "Functional organization of the riboflavin biosynthesis operon from *Bacillus subtilis* SHgw", Molecular & General Genetics, 242:201 (1994).
Mironov, et al., "Sensing small molecules by nascent RNA: a mechanism to control transcription in bacteria", Cell, 111:747-56 (2002).
Molinaro and Tinoco, "Use of ultra stable UNCG tetraloop hirpins to fold RNA structures: thermodynamic & spectroscopic applications", Nucleic Acids Res., 23:3056-63 (1995).
Montange and Batey, "Structure of the S-adenosylmethionine riboswitch regulatory mRNA element", Nature, 441:1172-75 (2006).
Moore and Sharp, "Site specific modification of Pre-mRNA: the 2'-hydroxyly groups at the splice sites", Science, 256:992-996 (1992).

Morris, et al., "Automated docking using a Lamarckian genetic algorithem and an empirical binding free energy function", J. Compute. Chem., 19:1639-1662 (1998).

Morris, et al., "Distributed automated docking of flexible ligands to proteins: Parallel applications of Autodock 2.4", J. of Computer Aided Molecular Design, 10:293-304 (1996).

Morsy, et al., "Efficient adenoviral0mediated ornithine transcarbamylase expression in deficient mouse and human hepatocytes", J. Clin. Invest., 92:1580-1586 (1993).

Moszer, et al, "SubtiList: a relational database for the *Bacillus subtilis* genome", Nucleic Acids.Res., 30:62 (2002).

Moullier, et al., "Correction of lysosomal storeage in the liver and spleen of MPS VII mice by implantation of genetically modified skin fibroblasts", Nat. Gene. 4:154-159(1993).

Muesing, et al., "Regulation of mRNA accumulation by a human immunodeficiency virus trans-activator protein," Cell, 48:691, 1987.

Muhlrad and Parker, "Aberrant mRNAs with extended 3\ UTRs are substages for rapid degradation by mRNA surveillance", RNA, 5:1299-1307 (1999).

Mulligan, "The basic science of gene therapy", Science, 260:926-932 (1993).

Mulligan and Berg, "Expression of a bacterial gene in mammalian cells", Science, 209: 1422 (1980).

Mumberg, et al., "Alternative splicing of fosB transcripts results in differentially expressed mRNAs encoding functionally antagonistic proteins", Genes Dev., 5:1212-23 (1991).

Murashige and Skoog, "A revised medium for rapid growth and bioassays with tobacco tissue cultures", Physiol. Plant, 15:473-497 (1962).

Murphy, et al., "Prediction of gene function in methylthioadenosine recycling from regulatory signals", Journal of Bacteriology, 184:2314 (2002).

Murphy-McDaniel, et al., "Transcription termination control of the S box system: direct measurement of S-adenosylmethionine by the leader RNA", PNAS, 100(6):3083-88 (2003).

Murzin, et al., "SCOP: a structural classification of proteins database for the investigation of sequences and structures", J. Mol. Biol., 247:536-40 (1995).

Nahvi, et al., "Coenzyme B12 riboswitches are widespread genetic control elements in prokaryotes", Nucleic Acids Res, 32:143-150 (2004).

Nahvi, et al., "Genetic control by a metabolite binding mRNA", Chem Biol., 9:1043-49 (2002).

Nakamura, et al., High-affinity taurine uptake and its regulation by protein kinase C in human glioma cells., Adv. Exp. Med. Bio, 403:377-84 (1996).

Nathans and Smith, "Restriction endonucleases in the analysis and restructuring of DNA molecules", Ann. Rev. Biochem., 44:273-293 (1975).

Needleman and Wunsch, "A general method applicable to the search for similarities in the amino acid sequence of two proteins", J. Mol. Biol., 48:443 (1970).

Neph and Tompa, "MicroFootAPrinter: a tool for phylogenetic footprinting in prokaryotic genomes", Nucleic Acids Res., 34 (2006).

Newman, et al., "DST sequences highly conserved among plant SAUR genes, target reporter transcripts for rapid decay in tobacco", Plant Cell, 5:701-14 (1993).

Nichols and Rajagopalan, "*Escherichia coli* MoeA and MogA, function in metal incorporation step of molybdenum cofactor biosynthesis", J. Biol. Chem., 277:24995-2500 (2002).

Nielsen, et al., "Sequence-selective recognition of DNA by strand displacement with a thymine-substituted polyamide", Science, 254:1497-1500 (1991).

Nissen, et al., "RNA tertiary interactions in the large ribosomal subunit: the A minor motif", PNAS, 98:4899-4903 (2001).

Noeske, et al., "An intermolecular base triple as the basis of ligand specificity and affinity in the guanine and adenine—sensing ribosweitch RNAs", PNAS, 102:1372-77 (2005).

Noguchi, et al., "Isolation and characterization of an *Eschrichia coli* mutant lacking tRNA-guanine transglycosylase, function and biosynthesis of queuosine in tRNA", J. Biol. Chem.., 257:6544-50 (1982).

Noonberg, et al., "In vivo generation of high abundant sequence-specific oligonucleotides for antisnes and triplex gene regulation", Nucleic Acids Res., 22 (14) 2830-2836 (1994).

Nou and Kadner, "Adenosylcobalamin inhibits ribosome binding to btuB RNA", PNAS, 97:7190-7195 (2000).

Nudler, et al., "The riboswitch control of bacterail metabolism", Trends in Biochem Sci., 29(1):11-17 (2004).

Nudler and Gottesman, "Transcription termination and anti-termination in *E.coli*", Genes to Cells, 7, 755 (2002).

Nygard, et al, "Total homocysteine and cardiovascular disease", J. Intern. Med., 245:425-54 (1999).

Ohkawa, et al., "Activities of HIV-RNA targeted ribozymes transcribed form a shot gun type ribozyme trimming plasmid", Nucleic Acids Symp. Ser., 27:15-16 (1992).

Ojwang,et al., "Inhibition of human immunodeficiency virus type-1 expression by hairpin ribozyme", PNAS, 89:10802-10806 (1992).

Okada, et al., "Novel mechanism of post-transcriptional modification of tRNA", J. Biol. Chem., 254:3067-73 (1979).

Okada, et al., "Structure determination of a nucleoside Q precursor isolated from *e coli* tRNA: 7-(aminomethyl)7-deasaguanine", Nucleic Acids Res., 5:2289-96 (1978).

Oku, et al., "Real time analysis of liposomal trafficking in tumor-bearing mice by use of positron emission tomography", Biochimica et Biophysica Acta., 1236: 86-90 (1995).

Old, et al., "Cloning and characterization of the genes for the two homocysteine transmethylases of *Escherichia coli*", Mol. Gen. Genet., 211:78-87 (1988).

Ono, et al., "DNA triplex formation of oligonucleotide analogues consisting of linker groups and octamer segments that have opposite sugar-phosphate backbone polarities", Biochemistry, 30:9914-9921 (1992).

Orbach, et al., "Cloning and characterization of the gene for brta-tubulin from a benomyl-resistant mutant of neurospora crasse and is use as a dominant selectable marker", Mol. Cell Biol., 6:2452-61 (1986).

Orengo and Thornton, "Protein families and their evolution-a structural prespective", Annu. Rev. Biochem., 74:867-900 (2005).

Orgel, et al., "Selection in vitro", Proc. R. Soc. London B., 205:435-442 (1979).

Osborne, et al., "Characterization of a native hammerhead ribozyme derived from schistosomes", RNA, 11:187-196 (2005).

Osborne, et al., "Transcription control region within the protein-coding portion of adenovirus E1A genes", Mol. Cell Bio., 4:1293 (1984).

Osborne and Ellington, "Nucleic acid selection and the challenge of combinatorial chemistry", Chem. Rev., 97:349-370 (1997).

Osman, et al., "A cis-acting element in the 3\-untransloated region of human TNF-alpha mRNA renders splicing dependent on the activation of protein kinase PRK", Genes and Devel., 13(24):3280-93 (1999).

Pan, et al., "Properites of an in vitro selected Pb2+ cleavage motif.", Biochemistry, 33:9561-9564 (1994).

Patte, et al., "The leader sequence of the *Escherichia coli* lysC gene is involved in the regulation of LysC synthesis", FEMS Microbiol. Lett., 169:165-170 (1998).

Patte, "Biosynthesis of lysine and threonine. In: *Escherichia coli* and *Salmonella*", Cellular and Molecular Biology, eds, 1:528-541 (1996).

Pearson and Lipman, "Improved tools for biological sequence comparison", PNAS, 85:2444 (1988),Pearson and Lipman, "Improved tools for biological sequence comparison", PNAS, 85:2444 (1988).

Pease, et al., "Light-generated oligonucleotide arrays for rapid DNA sequence anlysis", PNAS, 91(11):5022-5026 (1994).

Pedersen, et al., "Identification and classification of conserved RNA secondary structures in the human genome", PloS computational Biology, 2(4):e33 (2006).

Penchovsky, et al., "DNA library design for molecular computation", J. Comput. Biol., 10:215-229 (2003).

Perreault, et al., "Mixed deoxyribo- and ribo-oligonucleotides with catalytic activity", Nature, 344:565-567 (1990).

Perrotta and Been, "Cleavage of oligoribonucleotides by a ribozyme derived from the hepatitis delta virus RNA sequence", Biochem., 31(1):16 (1992).

Pflugrath, "The finer things in X-ray diffraction data collection", Acta Crystallogr., D55:1718-1725 (1999).
Phadtare and Inouye, "Sequence-selective interactions eith RNA by CspB, CspC and CspE members of the CspA family of *Escherichia coli*", Mol. Microbiol., 33:1004-14 (1999).
Pieken, et al., "Kinetic characterization of ribonuclease resistant 2' modified hammerhead ribozymes", Science, 253:314-317 (1991).
Pierce, et al., "Isothermal titration calorimetry of protein-protein interactions", Methods, 19:213-221 (1999).
Pitterle, et al., In vitro synthesis of molybdopterin from precursor Z using purified converting factor, role of protein-bound sulfur in formation of the dithiolene, J. Biol. Chem., 268:13506-09 (1993).
Porta, et al.,"An allosteric hammerhead ribozyme", Biotechnol., 13:161-164 (1995).
Proudfoot, et al., "Integrating mRNA processing with transcription", Cell, 108:501-12 (2002).
Proudfoot, "How RNAS polymerase II terminates transcription in higher eukaryotes", Trends Biochem. Sci, 14:105-10 (1989).
Proudfoot, "New perspectives on connecting messenger RNA 3\ end formation to transcription", Curr Opin Cell Biol., 15:272-78 (2004).
Pruitt, et al., "NCBI reference sequence (RefSeq) a curated nonredundant sequence of genomes, transcripts and protens", Nucleic Acids Res., 33:501-04 (2005).
Ragot, et al., "Replication-defective recombinant adenovirus expressing the Epstein-Barr virus (EBV) envelope glycoprotein gp340/220 induces protective immunity against EBV-induced lymphomas in the cottontop tamarin", J. Gen. Virology, 74:501-507 (1993).
Ram, et al., "In situr retroviral-mediated gene transfer for the treatment of brain tumors in rats", Cancer Res., 53:83-88 (1993).
Ravanum and Andersson, "An adenosyl-cobalamin (coenzyme-B12) repressed translational enhancer in the cob mRNA af *Salmonella typhimurium*", Mol. Microbiol., 39: 1585-1594 (2001).
Reader, et al., "Identification of four genes necessary for biosynthesis of the modified nucleoside queuosine", J. Biol. Chem.., 279:6280-85 (2004).
Recht and Williamson, "Central domain assempby: thermodynamics and kinetics of S6 and 818 binding to an S15-RNA complex", J. Mol. Biol, 313:35-48 (2001).
Reguera, et al., "Extracellular electron transfer via microbial nanowires", Natue, 435:1098-1101 (2005).
Regulski, et al., "A widespread riboswitch candidate that controls bacterial genes involved in molybdenum cofactor and tungsten cofactor metabolism", Mol. Microbiol., 68:918-32 (2008).
Reinhold-Hurek and Shub, "Self-splicing introns in tRNA genes of widely divergent bacteria", Nature, 357:173-176 (1992).
Rentmeister, et al., "Conformational changes in the expression domain of the *Escherichia coli* thiM riboswitch", Nucleic Acids Res., 35(11):13-22 (2007).
Reuter, et al., "Structure and organization of *Escherichia coli* genes involved in biosynthesis of the deazaguamine derivative queunine a nutrient factor for eukaryotes", J. Bacteriol., 173:2256-64 (1991).
Rey, et al., "The MchR repressor modulated by the effector substance S-adenosylhomocysteine controls directly the transcription of a regulon involved in sulphur metabolism of corynebacterium glutamicum ATCC 13032", Mol. Microbiol., 56:871-887 (2005).
Rice, et al., "Single wavelength anomalous diffraction phasing revisited", Acta Crystallogr D Biol. Crystallogr, 56 (Pt 11):1413-20 (2000).
Rich, et al., "Development and anlysis of recombinant adenovirus for gene therapy of cystic fibrosis", Human Gene Therapy, 4:461-476 (1993).
Richardson, "Phi-dependent termination and ATPases in transcript termination", Biochemica et Biophysica Acta, 1577:251 (2002).
Richardson and Schepartz, "Tethered olinucleotide probes. A strategy for the recognition of structured RNA", J. Am. Chem. Soc., 113: 5109-5111 (1991).
Robertson, et al., "Design and optimization of effector-activated ribozyme ligases", Nucleic Acids Res., 28(8):1751-9 (2000).
Robertson, et al. "In vitro selection of nucleoprotein enzymes", Nat. Biotechnol., 19(7):650-5 (2001).
Robertson, et al. "In vitro selection of ribozymes dependent on peptides for activity", RNA, 10:114-127 (2004).

Rodionov, et al., Comparative genomics of the methionine metabolism in Gram-positive bacteria: a variety of regulatory systems, Nucleic Acids Res., 32:3340-53 (2004).
Rodionov, et al., "Comparative genomics of the vitamin B12 metabolism and regulation in prokaryotes", J. Biol. Chem.., 278:41148-59 (2003a).
Rodionov, et al., "Comparative genomics of thiamin biosynthesis in procaryotes. New genes and regulatory mechanisms", J. Biological chemistry, 277:48949-59 (2002).
Rodionov, et al., "Regulation of lysine biosynthesis and transport genes in bacteria: yet another RNA riboswitch?", Nucleic Acids Res., 31:6748-6757 (2003).
Roessler, et al, "Adenoviral-mediated gene transfer to rabbit synovium in vivo", J. Clin. Invest., 92:1085-1092 (1993).
Romling, et al., C-di-GMP: the dawning of a novel bacterial signalling system Mol. Microbiol., 57:629-39 (2005).
Rosentel, et al., "Molybdate and regulation of mod (molybdate transport), fdhF and hyc (formate hydrogenlyase) operons in *Escherichia coli*", J. Bacteriol., 177:4857-64 (1995).
Ross, et al., "An unusual guanyl oligonucleotide regulates cellulose synthesis in Acetobacter xylinum", FEBS Lett., 186:191-96 (1985).
Ross, et al., "Regulation of cellulose synthesis in Acetobacter xylinum by cyclic diguanylic acid", Nature, 325:279-81 (1987).
Rossi, et al., "Molecular Biology: ribozymes in the nucleolus", Science, 285:1685 (1999).
Rossi, et al., "Ribozymes as anti-HIV-1 therapeutic agents: principles, applications and problems", AIDS Res. Hum. Retrovir., 8(2):183 (1992).
Roth, et al., "Finding DNA regulatory motifs within unaligned noncoding sequences clustered by whole-genome mRNA quantitation," Nat. Biotechnol., 16:939-945, 1998.
Roth, et al., "A riboswitch selective for thr queuosine precursor preQ(1) contains an unusually small aptamer domain", Nature Structural and Mol. Bio.,14 (4):308-17 (2007).
Roth, et al., "Characteristics of the glmS ribozyme suggest only structural roles for divalent metal ions", RNA, 12:607-619 (2006).
Roth and Breaker, "An amino acid as a cofactor for a catalytic polynucleotide", PNAS, 95:6027-6031 (1998).
Roth and Breaker, "Selection in vitro of allosteric ribozymes", In: Mehthods in Molecular Biology Series—Catalytic Nucleic Acid Protocols (Sioud, M, ed.) Humana, Totowa, NJ (2003).
Roychowdhury-Saha, et al., "Flavin recognition by an RNA aptamer targeted toward FAD", Biochemistry, 41:2492 (2002).
Ruffner, et al., "Sequence requirements of the hammerhead RNA self-cleavage reaction", Biochemistry, 29:10695-10 702 (1990).
Rusch, et al., "The Sorcerer II Global Ocean Sampling expedition: northwest Atlantic through eastern tropical Pacific", PloS Biol., 5:e77 (2007).
Russell, et al., "Exploring the folding landscape of a structured RNA", Proc. Natl. Acad. Sci. USA, 99:155-160 (2002).
Ryan, et al., "Cyclic di-GMP signaling in bacteria: recent advances and new puzzles", J. Bacteriol., 188:8327-34 (2006).
Ryjenkov, et al., "The PilZ domain is a receptor for the second messenger c-di-GMP: the PilZ domain protein YcgR controls motility in enterobacteria", J. Biol. Chem., 281:30310-14 (2006).
Salazar, et al., "A truncated aminoacyl-tRNA synthetase modifies RNA", PNAS, 101:7536-41 (2004).
Sambrook, et al., Molcular Cloning: A Laboratory Manual, 2nd Ed., Cold Spring Harbor Laboratory, Cold Spring Harbor, NY (1989).
Sanghvi, Antisense Research and Applications Ch15:289-302, ed, CRC Press (1993).
Sanishvili, et al., "The crystal structure of *Escherichia coli* MoaB suggests a probable role in molybdenum cofactor synthesis", J. Biol. Chem., 279:42139-46 (2004).
Sano,et al., "Detection of heavy methylation in human repetitive DNA subsets by a monoclonal antibody against 5-methylcytosine", Biochim. Biophys. Acta, 951:157-165 (1988).
Santamaria-Araujo, et al., The tetrahydropyranopterin structure of the sulfur-free and metal-free molybdenum cofactor precursor, J. Biol. Chem., 279:15994-15999 (2004).
Sarver, et al., "Ribozymes as potential anti-HIV-1 therpeutic agents", Science, 247: 1222-1225 (1990).

Saville and Collins, "A site-specific self-cleavage reaction performed by a novel RNA in Neurospora mitochondria", Cell, 61(4):685-696 (1990).
Saville and Collins, "RNA-mediated ligation of self-cleavage products of a Neurospora mitochondrial plasmid transcript", Proc. Natl. Acad. Sci. USA, 88 (19):8826-8830 (1991).
Scanlon, et al., "Riobzyme-mediated cleavage of c-fos mRNA reduces gene expression of DNA synthesis enzymes and metal-lothonien", PNAS, 88:10591-10595 (1991).
Scaringe, et al., "Chemical synthesis of biologically active oligoribonucleotides using beta-cyantethyl protected ribonucleoside phosphramidites", Nuceic Acids Res. 18:5433-5441 (1990).
Schaffer, et al., "Improving the accuracy of PSI-BLAST protein database searches with composition-based statistics and other refinements". Nucleic Acids Res., 29:2994-3005 (2001).
Schauder, et al., "The LuxS family of bacterial autoinducers: biosynthesis of a novel quorum-sensing signal molecule", Mol. Microbiol., 41:463-476 (2001).
Schray, et al., "Anomerization rates and enzyme specificity for biologically important sugars and sugar phosphates", Chem. Res., 11:136-141 (1978).
Schubert, et al., "Ribozyme- and deoxyribozymes-strategies for medical applications", Curr. Drug Targets, 5:667-681 (2004).
Schwarz, "Molybdenum cofactor biosynthesis and deficiency", Cell Mol. Life Sci., 62:2792-2810 (2005).
Schweitzer and Kingsmore, "Combining nucleic acid amplification and detection", Curr. Opin. Biotech., 12:21-27 (2001).
Schyns, et al. "Isolation and characterization of new thiamine-deregulated mutants of *bacillus subtilis*", J. Bacteriol., 187:8127-36 (2005).
Scott and Amy, "Molybdenum accumulation in chlD mutants of *Escherichia coli*", J. Bacteriol., 171:1284-1237 (1989).
Seela and Kaiser, "Oligodeoxyribonucleotides containing 1, 3 propanedial as necleoside substitute", Nucleic Acids Res., 15:3113-3129 (1987).
Seetharaman, et al., "Immobilized riboswitches for the analysis of complex chemical and biological mixtures", Nature Biotechnol., 19:336-341 (2001).
Seliverstov, et al., "Comparative analysis of RNA regulatory elements of aminoi acid metabolism genes in actinobacteria", BMC Microbiol., 5:54 (2005).
Sengle, et al. "Novel RNA catalysts for the Michael reaction", Chem Biol., 8 (5):459-73 (2001).
Serganov, et al., "Structural basis for discriminative regulation of gene expression by adenine- and guanine-sensing mRNAs", Chem. Biol., 11:1729-1741 (2004).
Serganov, et al., "Structural basis for gene regulation by a thiamine pyrophosphate-sensing riboswitch", Nature, 441:1167-1171 (2006).
Seth, et al., "Evidence that the penton base of adenovirus is involved in potentiation of toxicity of Pseudomonas exotoxin conjugated to epidermal growth factor", Mol. Cell. Biol., 4: 1528-1533 (1984).
Seth, et al., "Role of a low-pH environmnet in adenovirus enhancement of the toxicity of a Pseudomonas exotoxin-epidermal growth factor conjugate", J. Virol., 51:650-655 (1984).
Shabarova, et al., "Chemical ligation of DNA: the first non-enzymatic assembly of a biologically active gene", Nucleic Acids Res., 19:4247-4251 (1991).
Shanmugam., et al., "Proposed nomenclature for the genes involved in molybdenum metabolism in *Escherichia coli* and *salmonella typhimurium*", Mol. Microbiol., 6:3452-54 (1992).
Sheppard, et al., "Purification and properties of NADH-depndent 5, 10-methylenetetrahydrofolate reductase (MetF) from *Escherichia coli*", J. Bacteriol, 181:718-25 (1999).
Shimizu, et al., "Occurrence of S-adenosylihomocysteine hydrolase in prokaryote cells-characterization of the enzyme from alcaligenes faecalis and role of the enzyme in the activated methyl cycle", Eur. J. Biochem., 141:385-92 (1984).
Shiota, et al., "Inhibition of lysine utilization in bacteria by S-(beta-aminoethly) cysteine and its reversal by lysine peptides", Arch. Biochem. Biophys., 77:372-7 (1958).
Shu and Guo, "A viral Rna that binds ATP and contains a motif similar to an ATP binding aptamer from SELEX", J. Biol. Chem., 278:7119-7125 (2003).

Silverman, "Molecular switches and sensors made from RNA", RNA, 9:377-383 (2003).
Simm, et al., "GGDEF and EAL domains inversely regulate cyclic di-GMP levels and transition from sessility to motility", Mol. Microbiol., 53:1123-34 (2004).
Simmons, et al., "A Complete protocol for in situ hybridization of massager RNA in brain andother tissues with radiolabeled single-stranded RNA probes", J. Histotech., 12:169-181 (1989).
Simons, at al., "Improved single and multicopy lac-based cloning vectors for porteina nd operon fusions", Gene, 53:85-96 (1987).
Slany, et al., "A new function of S-adenosylmethionine, the ribosyl moiety of AdoMet is the precursor of cyclopentenediol moiety of the tRNSA wobble base queuine", Biochemistry, 32:7811-17 (1993).
Slany, et al., "Transfer and isomerization of thr ribose moiety of AdoMet during the biosynthesis of queuosine tRNAs, a new unique reaction catalyzed by the QueA protein from *Escherichia coli*", Biochimie, 76:389-93 (1994).
Smith and Waterman, "Comparison of Biosequences", Adv. Appl. Math., 2:482 (1981).
Sosnick and Pan, "RNA folding: Models and perspectives", Curr. Opin. Struct. Biol., 13:309-316 (2003).
Soukup, et al., "Core requirements for glmS ribozyme self-cleavage reveal a putative pseudoknot structure", Nucleic Acids Res, 34: 968-975 (2006).
Soukup, et al., "Generating new ligand-binding RNAs by affinity maturation and disintegration fo allosteric ribozymes", RNA, 7:524-536 (2001).
Soukup and Breaker, "Allosteric Nucleic Acid Catalysts", Curr. Opin. Struct. Biol., 10: 318-325 (2000).
Soukup and Breaker, "Engineering precision RNA molcular switches", PNAS, 96: 3584-3589 (1999).
Soukup and Breaker, Nucleic Acid Molecular Switches. Trends Biotechnol., 17: 469-476 (1999).
Soukup and Breaker, "Relationship between internucleotie linkage geometry and the stability of P,-NA", RNA, 5:1308-1325 (1999b).
Soukup and Soukup, "Riboswitches exert genetic control through metabolite-induced conformational change", Curr. Opin. Struct. Biol., 14:344-49 (2004).
Southern and Berg, "Transformation of mammalian cells to antibiotic resistance with a bacterial gene under control of the SV40 early region promoter", J. Molec. Appl. Genet., 1: 327 (1982).
Spino and Guest, "FNR and its role in oxygen-related gene expression in *echerichia coli*", FEMS Microbiol Rev., 6:399-428 (1990).
Srinivasan, et al., "ADP-specific sensors enable universal assay of protein kinase activity", Chem. Biol., 11:499-508 (2004).
Steffes, et al., "The lysP gene encodes the lysine-specific permease", J. Bacteriol., 174: 3242-3249 (1992).
Stimpson, et al., "Real-time detection of DNA hybridization and melting on oligonucleotide arrays by using optical wave guides", PNAS, 92:6379-6383 (1995).
Stoddard and Batey, "Mix and match riboswitches", ACS Chem. Biol., 1:751-54 (2006).
Stojanovic, et al., "A deoxyribozyme-based molecular automaton", Nat. Biotechnol. 21:1069-1074 (2003).
Stojanovic, et al., "Computational methods for the analysis of differential conservation in groups of similar DNA sequences", Genome Inform., 15:21-30 (2004).
Stojanovic, et al., "Deoxyribozyme-based half-adder", J. Am. Chem. Soc., 125: 6673-6676 (2003).
Stojanovic, et al., Deoxyribozyme-based logic gates J. Am. Chem. Soc. 124:3555-3561 (2002).
Stormo and Ji, "mRNAs act as direct sensors of small moleculres to control their expression", PNAS, 98: 9465-9467 (2001).
Storz, et al., "An abundance of RNA regulators", Annu. Rev. Biochem., 74:199-217 (2005).
Street and Msyo, "Pairwise calculation of protein solvent-accessible surface areas", Folding & Design, 3:253-258 (1998).
Stulke, "Control of transcription termination in bacteria by RNA-binding proteins that modulate RNA structures", Archives of Microbiology, 177:433 (2002).
Sudarsan, et al., "An mRNA structure in bacteria that controls gene expression by binding lysine", Genes Dev., 17:2688-97 (2003a).

Sudarsan, et al., "Metabolite binding RNA domains are present in the genes of eukaryotes", RNA, 9:644-647 (2003b).
Sudarsan, et al., "Tandem riboswitch architectures exhibit complex gene control functions", Science, 314:300-4 (2006).
Sudarsan, et al., "Thiamine pyrophosphate riboswitches are targets for the antimicrobial compound pyrithiamine", Chem. Biol., 12:1325-1335 (2005).
Suess, et al., "A theophylline responsive riboswitch based on helix slipping controls gene expression in vivo", Nucleic Acids Res., 32:1610-1614 (2004).
Sugden, et al., A vector that replicates as a plasmid and can be efficiently selected in B-lymphoblasts transformed by Epstein Barr virus. Mol. Cell Biol., 5: 410-413 (1985).
Sugiyama. et al., Catalytic activities of hammerhead ribozymes with a triterpenoid linker instead of stem/loop II. FEBS Letters 392: 215-219 (1996).
Sullenger and Cech, Tethering ribozymes to a retroviral packaging signal for destruction of viral RNA. Science 262: 1566-1569 (1993).
Svensson and Persson, Role of vesicles during adenovirus 2 internalization into HeLa cells. J. Virology, 55: 442-449 (1985).
Switzer, at al., "Regulation of the *Bacillus subtilis* pyrimidine biosynthetic operon by transcriptional attenuation: control of gene expression by an mRNA-binding protein", Prog Nucleic Acids Res. Mol. Biol., 62:329-367 (1999).
Szostak, "In vitro genetics", TIBS, 17:89-93 (1992).
Szostak and Ellington, In vitro selection of functional RNA sequences, RNA World ED, Cold Spring Harbor Laboratory Press, 511-533 (1993).
Tabor and Tabor, "Methionine adenosyltransferase (S-adenosylmethionine synthetase) and S-adenosylmethionine decarboxylase, advances enzymol related areas", Mol. Biol., 56:251-82 (1984).
Taira, et al., Construction of a novel RNA transcript trimming plasmid which can be used both in vitro in place of run-off and (G) free transcriptions and in vivo as multi sequences transcription vectors, Nucleic Acid Res., 19:5125-5130 (1991).
Tamayo, et al., "Interpreting patterns of gene expression with self-organizing maps: methods and application to hematopoietic differentiation," Proc. Nat'l Acad. Sci. USA, 96:2907-2912 (1999).
Tamayo, et al., "Roles of cyclic diguanylate in pathogenesis", Ann. Review of Microbiology, 61:131-48 (2007).
Tamm, et al., "Anti sense therapy in ocology: new hope for an old idea", The Lancet, 358:489-497 (2001).
Tang, et al., "Rational design of allosteric ribozymes", Chem. Biol., 4:453-459 (1997).
Tang and Breaker, "Examniation of the catalytic fitness of the hammerhead ribozyme by in vitro selection", RNA, 3:914-925 (1997).
Tang and Guest, Direct evidence for mRNA binding and post-transcriptional regulation by *Escherichia coli* aconitases, Microbiology, 145:3069-79 (1999).
Tarasow, et al. "RNA-catalysed carbon-barbon bond formation", Nature, 389 (6646) 54-7 (1997).
Tatusov, et al, "The COG database, an updated version includes eukaryotes", BMC Bioinformatics, 4:41 (2003).
Tatusov, et al., "The COG database: new developments in phylogenetic classification of porteins from complete genomes", Nucleic Acids Res., 29:22-28 (2001).
Teixeira, et al., "Autocatalytic RNA cleavage in the human beta-globin pre-mRNA promotes transcription termination", Nature, 432:526-530 (2004).
Teplyakov, et al., "Involvement of the C terminus in intramolecular nitrogen channeling in glucosamine 6-phosphate synthase: evidence from a 1.6 A crystal structure of the isomerase domain", Structure, 6:1047-1055 (1998).
Tereshko, et al., "X-ray crystallographic observation of "in-lin" and "adjacent" conformations in a bulged self-cleaving RNA/DNA hybrid", RNA, 7:405 (2001).
Thompson, et al., "Improved accumulation and activity of ribozymes expressed froma tRNA based RNA polymerase III promoter", Nucleic Acids Res., 23:2259-2269 (1995).
Thompson, et al., "Synthesis of two stable nitrogen analogues of S-adenosyl-L-methionine", J. Org. Chem., 64:7467-73 (1999).
Thompson, et al. "Group I aptazymes as genetic regulatory switches", BCM Biotechnol., 2:21 (2002).
Thomson, et al., "In vitro selection of hammerhead ribozymes containing a bulged nucleotide in stem II", Nucleic Acids Res., 24:4401-4406 (1996).
Thore, et al., "Structure of the eukaryotic thiamine pyrophosphate riboswitch with its regulatory ligand", Science, 312:1208-11 (2006).
Tischler and Camilli, "Cyclic diguanylate regulates *Vibrio cholerae* virulence gene expression", Infect. Immun., 73:5873-82 (2005).
Toennies, et al., "Methionine studies.VI. Dl-methionine sulfone", J. Biol. Chem., 140:131-134 (1941).
Torarinsson, et al., "Thousands of corresponding human and mouse genomic regions unalignable in primary sequence contain common RNA structure", Genome Res., 16:885-89 (2006).
Toraya, In: Chemistry and Bichemistry of B12. Banerjee, R. Ed. (Wiley, NY)pp. 783-809 (1999).
Torres-Larios, et al., "Structural basis of translational control by *Escherichia coli*threonyl tRNA synthetase", Nat. Struct. Biol., 9:343-47 (2002).
Torres-Larios, et al., "Structure of ribonuclease P-a universal ribozyme", Curr. Opin. Struct. Biol., 16:327-35 (2006).
Tringe, et al., "Comparative metagenomics of microbial communities", Science, 308:554-57 (2005).
Tucker, et al., "Riboswitches as versatile gene control elements", Curr.Opin. Struc. Bio., 15:342-348 (2005).
Turnbaugh, et al, "An obesity-associated gut microbiome with increased capacity for energy harvest", Nature, 444:1027-31 (2006).
Turner, et al., Improved parameters for prediction of RNA structure, Cold Spring Harbor Symposia on Quantitative Biology, III:123-133 (1987).
Turner.et al., "Free energy increments for dydrogen bods in nucleic acid base pairs", J. Am. Chem. Soc., 109:3783-3785 (1987).
Tyagi and Karmer, "Molecular beacons: probes that fluoresce upon hybridization", Nature Biotechnology, 14:303 (1996).
Tyson, et al., "Community structure and metabolism through reconstruction of microbial genomes from the environment", Nature, 428:37-43 (2004).
Ueland, "Pharmacological and biochemical aspects of S-adenosylhomocysteine and S-adenosylhimocysteine hydrolase", Pharm. Rev., 34:223-285 (1982).
Ulrich, et al., "One-component systems dominate signal transduction in prokaryotes", Trends Microbiol., 13:52-56 (2005).
Urbonavicius, et al., "Improvement of reading frame maintenance is a common function for several rRNA modification", EMBO J., 20:4863-73 (2001).
Usher, "On the mechanism of ribonuclease action", PNAS, 62:661-667 (1969).
Usher and McHale, "Hydorlytic stability of helical RNA: a selective advantage for the natureal 3', 5'-bond", PNAS, 73:1149-1153 (1976).
Usman, et al., "Automated chemical synthesis of long oligoribonucleotides using 2'O-silylated ribonucleoside 3'O-phophoraladites ona controlled pore glass support: synthesis of a 43-necleotide sequence similar to the 3'half molecule of an *Escherichia coli* formylmethionine tRNA", J. Am. Chem. Soc., 109:7845-7854 (1987).
Usman, et al., "Chemical modification of hammerhead ribozymes: activity and nuclease resistance", Nucleic Acids Symposium Seires, 31:163-164 (1994).
Usman and Cedergren, "Exploiting the chemical synthesis of RNA", TIBS, 17: 334-339 (1992).
Usman and McSwiggen, "Catalytic RNA (ribozymes) as drugs", Annual rports in medicinal Chem., 30:285-294 (1995).
Vader, et al., "In vivo expression of the nucleolar group I intron-encoded al-dirl homing endonuclease involves the removal of a spliceosomal intron", EMBO J., 18:1003-13 (1999).
Vaish, et al, "In vitro selection of a purine nucleotide specific hammerhead-like ribozyme", PNAS, 95:2158-2162 (1998).
van Aalten, et al., "PRODRG, a program for generating molecular topolgies and unique molecular descriptors from coordinates of small molecules", J. Comput. Aided Mol. Design, 10:255-262 (1996).
Van Lanen, et al., "From cyclohydrolase to oxidoreductase, discovery of nitrile reductase activity in a common fold", PNAS, 102:4264-69 (2005).

Vander Horn, et al., "Structural genes for thiamine biosynthetic enzymes (thiCEFGH) in *Echerichia coli* K-12", J. Bacteriolgoy, 175:982-992 (1993).

Vann, "Electroporation-based transformation of freshly harvested conidia of neurospora crassa", Fungal Genet. Newl., 42A:53 (1995).

Varga, et al., "Infectious entry pathway of adenovirus type 2", J Virology, 65:6061-6070 (1991).

Vecerek, et al., "Translational autocontrol of the *Escherichia coli* hfq RNA chaperone gene", RNA, 11:976-84 (2005).

Venter, et al., "Enviromental gerome shotgun sequencing of the Sargasso Sea", Science, 304:66-74 (2004).

Ventura, et al., "Activation of HIV-specific ribozyme activity by self-cleavage", Nucleic Acids Res., 21:3249-3255 (1993).

Verma, "Retroviral vectors for gene transfer",Am. Soc. Microbio. :229-232, (1985).

Vicens and Cech, "Atomic level architecture of group I introns revealed", Trends Biochem. Sci., 31:41-51 (2006).

Vilela and McCarthy, "Regulation of fungal gene expression via short open reading frames in the mRNA 5\ untranslated region", Mol. Microbiol., 49:859-867 (2003).

Vitreschak, et al., "Regulation of riboflavin biosynthesis and transport genes in bacteria by transcriptional and translational attenuation", Nucleic Acids Res., 30:3141-51 (2002).

Vitreschak, et al., "Regulation of the vitamin B12 metabolism and transport in bacteria by a conserved RNA structural element", RNA, 9:1084-97 (2003).

Vitreschak,et al., "Riboswitches: the oldest mechanism for the regulation of gene expression?", Trends in Genetics, 20(1):44-50 (2004).

Vold, et al., "Regulation of dihydrodipicolinate synthase and aspartate kinase in *Bacillus subtilis*", J. Bacteriol., 121:970-974 (1975).

Wachter, et al., "Riboswitch control of gene expression in plants by splicing and alternative 3\ end processing of mRNAs", Plant Cell, 19:3437-50 (2007).

Wan and Xu, "Intrinsic terminator prediction and its application in synechococcus sp. WH8102", J. Comp. Sci. & Tech., 20:465-82 (2004).

Wang, et al., "A general approach for the use of oligonucleotides effectors to regulate the catalysis of RNA-cleaving ribozymes and DNAzymes", Nucleic Acids Res, 30:1735-1742 (2002).

Wang, et al., "Dual function of rice OsDR8 gene in disease resistance and thiamine accumulation", Plant Mol. Biol., 60:437-449 (2006).

Wang, et al., "Riboswitches that sense S-adenosylhomocysteine and activate genes involved in coenzyme recycling", Mol. Cell., (2008).

Wansink, et al., "Fluorescent labeling of nascent RNA reveals transcription by RNA polymerase II in domains scattered throughout the nucleus", J. Cell Biology, 122:283-293 (1993).

Washietl, et al., "Mapping of conserved RNA secondary structures predicts thousands of functional noncoding RNAs in the human genome", Nature Biotech., 23:1383-90 (2005).

Wassmann, et al., "Structure of BeF3—modified response regulator PleD: implications for diguanylate cyclase activation, catalysis, and feedback inhibition", Structure, 15:915-27 (2007).

Waters, et al., "Quorum sensing controls biofilm formation in *Vibrio cholerae* through modulation of cyclic di-GMP levels and repression of vpsT", J. Bacteriol., 190:2527-36 (2008).

Webb, et al., "Thiamine pyrophosphate (TPP) negatively regulates transcription of some thi genes of *Salmonella typhimurium*", J. Bacteriol., 178:2533-2538 (1996).

Webb and Downs, "Characterization of thiL, encoding thiaminmonophosphate kinase, in *Salmonella typhimurium*", J. Biol. Chem., 272:15702-15707 (1997).

Weerasinghe, et al., "Resistance to human immunodeficiency virus using type 1 (HIV-1) infection human CD4+ lymphocyte dreived cell lines conferred by using retroviral vectors expressing an HIV-1 RNA specific ribozyme", J. Virol., 65:5531-5534 (1994).

Wei, et al., "Conserved sturctureal and regulatory regions in the *Salmonella typhimurium* btuB gene for the outer membrane vitamin B12 transport protein", Res. Microbiol. 143:459 (1992).

Weigand, et al., "Tetracycline aptamer-controlled regulation of pre-mRNA splicing in yeast", Nucleic Acids Res., 35(12):4179-85 (2007).

Weinberg, et al., "Identification of 22 candidate structured RNAs in bacteria using the CMfinder comparative geomics pipeline", Nucleic Acids Res., 35:4809-19 (2007).

Weinberg and Ruzzo, "Exploiting conserved structure for faster annotation of non-coding RNAs without loss of accuracy", Bioinformatics, 20 (Suppl 1):1334-41 (2004).

Weinberg and Ruzzo, "Faster genome annotation of non-coding RNA families without loss of accuracy", Proceedings of the eighth annual international conference on Computational Molecular Biology, 243-251 (2004).

Weinberg and Ruzzo, "Sequence-based heuristics for faster annotation of non-coding RNA families", Bioinformatics, 22:35-39 (2006).

Weissbluth, In Molecular Biology Biochemistry and Biophysics, A. Kleinzeller, Ed., v 15:27-41 (1974).

Welz and Breaker, "Ligand binding and gene control characteristics of tandem riboswitches in *Bacillus anthracis*", RNA, 13(4):573-82 (2007).

Weng, et al., "Identification of the *Bacillus subtilis* pur operon repressor", PNAS, 92: 7455-7459 (1995).

Werner and Uhlenbeck, "The effect of base mismatches in the substrate recognition helices of hammerhead ribozymes on binding and catalysts", Nucleic Acids Res. 23:2092-2096 (1995).

Werstuck and Green, "Controlling gene expression in living cells through small molecule-RNA interactions", Science, 282:296-298 (1998).

West, "4-Hydroxypyrrolo[2,3-d]pyrimidine, mannich reaction", J. Org. Chem., 26:4959-61 (1961).

Westergaardand Mitchell "ANeurospora V A synthetic medium favoring sexual reproduction", Amer. J. Bot., 34:573-77 (1947).

Westheimer, "Pseudo-rotation in the hydorlysis of phosphate esters", Acc. Chem. Res., 1:70-78 (1968).

White III, "Coenzymes as fossils of an earlier metabolic state", J. Mol. Evol., 7:101-104 (1976).

White III, "In: The Pyridine Nucleotide Coenzymes", Acad. Press, NY pp. 1-17 (1982).

Wickham, et al., "Integrins alpha v beta 3 and alpha v beta 5 promote adenovirus internalization but not virus attachment", Cell, 73:309-319 (1993).

Wickiser, et al., "The Kinetics of Ligand Binding by an Adenine-Sensing Riboswitch", Biochemistry, 44:13404-13414 (2005).

Wickiser, et al., "The Speed of RNA Transcription and Metabolite Binding Kinetics Operate an FMN Riboswitch", Molecular cell, 18:49-60 (2005a).

Wiegand, et al., "Selection of RNA amide synthases", Chem Biol., 4(9): 675-83 (1997).

Wilkinson, et al., "A pseudoknot in the 3' non-core region of the glmS ribozyme enhances self-cleavage activity", RNA, 11:1788-1794 (2005).

Williamson, "Induced fit in RNA-protein recognition", Nat. Sturct. Biol., 7:834-837 (2000).

Wilson and von Hippel, "Transcription termination at intrinsic terminators: the role of the RNA hairpin", PNAS, 92:8793-8797 (1995).

Wimberly, et al., "The conformation of loop E of eukaryotic 5S ribosomal RNA", Biochemistry, 32:1078-1087 (1993).

Wincott, et al., "A practical method for the production of RNA and ribozymes", Methods in Mol. Biology, 74:59-69 (1997).

Wincott, et al., "Synthesis, dprotection, analysis and purification of RNA and ribozymes", Nucleic Acids Res 23(14):2677-2684 (1995).

Winkler, "Riboswitches and the role of noncoding RNAs in bacterial metabolic control", Curr. Opin Chem. Biol., 9:594-602 (2005).

Winkler and Breaker, "Genetic control by metabolite-binding riboswitches", Chem BioChem, 4(10):1024-32 (2003).

Winkler and Breaker, "Regulation of Bacterial gene expression by riboswitches", Ann Rev. Microbiol ., 59:487-517 (2005).

Winkler et al., "A mRNA sturcture that controls gene expression by binding FMN", PNAS, 99(25):15908-15913 (2002).

Winkler et al., "An mRNA structure that controls gene expression by binding S-adenosylmethionine", Nat Struct Biol, 10:701 (2003).

Winkler et al., "Control of gene expression by a natural metabolite-responsive ribozyme", Nature, 428(6980):281-6 (2004).

Winkler et al., "Thiamine derivatives bind messenger RNAs directly to regulate bacterial gene expression", Nature, 419:952-956 (2002).

Wolfe and Visick, "Get the message out: cyclic-Di-GMP regulates multiple levels of flagellum-based motility", J. Bacteriol., 190:463-75 (2008).

Wolff, et al., "Direct gene transfer into mouse muscle in vivo", Science, 247:1465-1468 (1990).

Wolff, et al., "Human dystrophin expression in mdx mice after intramuscular injection of DNA constructs", Nature, 352:815-818 (1991).

Wolfson, et al., "Holding back the tide of antiobiotic resistance". Chem. Biol., 13:1-3 (2006).

Woodson, "Folding mechanisms of group I ribozymes: Role of stability and contract order", Biochem. Soc. Trans., 30:1166-1169 (2002).

Woolf, et al., "Specificity of antisense oligonucleotides in vivo". PNAS, 89:7305-9 (1992).

Woolley, et al., "Selective reversible inhibition of microbial growth with pyrithiamine", J. Exp. Med., 78:489-497 (1943).

Woyke, et al., "Symbiosis insights through metagenomic analysis of a microbial consortium", Nature, 443:950-55 (2006).

Wuebbens and Rajagopalan, "Investigation of the early steps of molybdopterin biosynthesis in *Escherichia coli* through the use of in vivo labeling studies", J. Biol. Chem., 270:1082-87 (1995).

Yamamoto and Ishihama, "Transcriptional response of *Escherichia coli* to external copper", Mol. Microbiol., 56:215-227 (2005).

Yao, et al., "A computational pipeline for high throughput discovery of cis-regulatory noncoding RNA in prokaryotes", PLoS Comput. Biol., 3:e126 (2007).

Yao et al., "CMfinder-a covariance model based RNA motif finding algorithm", Bioinformatics, 22:445-52 (2006).

Yarnell and Roberts, "Mechanism of intrinsic transcription termination and antitermination", Science, 284:611-15 (1999).

Yen, et al., "An alternative spliced form of FosB is a negative regulator of transcriptional activation and transformation by Fos proteins", PNAS, 88:5077-81 (1991).

Yen, et al., "Exogenous control of mammalian gene expression through modulation of A self-cleavage", Nature, 431:471-476 (2004).

Yu et al., "A hairpin ribozyme inhibits expression of diverse strains of human immunodeficiency virus type 1", PNAS, 90:6340-6344 (1993).

Yu et al., "Cyanine dye dUTP analogs for enzymatic labeling of DNA probes", Nucleic Acids Res., 22:3226-3232 (1994).

Zabner, et al., "Adenovirus-mediated gene transfer transiently corrects the chloride transport defect in nasal epithelia of patients with cystic fibrosis", Cell, 75:207-216 (1993).

Zabner, et al., "Safety and efficacy of repetitive adenovirus-mediated transfer of CFTR cDNA to airway epithelia of primates and cotton rats", Nature Genetics, 6:75-83 (1994).

Zaug, et al., "The tetrahymena ribozyme acts like an RNA restirction endonuclease", Nature, 324:429-433 (1986).

Zengel and Lindahl, "Diverse mechanisms for regulating ribosomal protein synthesis in *Escherichia coli*", Prog. Nucleic Acid Res. Mol Biol., 47:331-370 (1994).

Zhang, et al., "Comparison of the three aspartokinase isozymes in *Bacillus subtilis* Marburg and 168", J. Bacteriol., 172:701-708 (1990).

Zhang, et al., Peptidyl-transferase ribozyme: trans reactions, structural characterization and ribosomal RNA-like features Chem Biol., 5(10):539-53 (1998).

Zhang, et al., "Polymorphism of the signaling molecule c-di-GMP", J Am. Chem. Soc., 128:7015-24 (2006).

Zhang, Generation and identification of recombinant adenovirus by liposome-mediated transfection and PCR analysis, BioTechniques, 15:868-872 (1993).

Zhou, et al., "Synthesis of functional mRNA in mammalian cells by bacteriophage T3 RNA polymerase", Mol Cell Biol., 10:4529-4537 (1990).

Zimmermann, et al., "Interlocking sturctural motifs mediate molecualr discrimination by a theophylline-binding RNA", Nature Struct. Biol., 4:644-649 (1997).

Zolotukhin, et al., "A 'humanized' green fluorescent protein cDNA adapted for high-level expression in mammalian cells," J. Virol., 70:4646-4654 (1996).

Zuker, et al., "Algorithms and thermodynamics for RNA secondary structure prediction: a practical guide", RNA Biochemistry and Biotechnology (eds. 11-43 NATO ASI Series, Kluwer Academic Pulbishers, (1999).

Zuker, "Mfold web server for nucleic acid folding and hybridization prediction", aNucleic Acids Res., 31:3406-15 (2003).

Zuker, "On finding all suboptimal foldings of an RNA molecule", Science, 244:48-52 (1989).

* cited by examiner

A

B

METHODS AND COMPOSITIONS RELATED TO THE MODULATION OF RIBOSWITCHES

CROSS-REFERENCE TO RELATED APPLICATIONS

This application claims benefit of U.S. Provisional Application No. 60/752,726, filed Dec. 21, 2005. U.S. Provisional Application No. 60/752,726, filed Dec. 21, 2005, is hereby incorporated herein by reference in its entirety.

REFERENCE TO SEQUENCE LISTING

The Sequence Listing submitted Jun. 24, 2010 as a text file named "24519_10_8402_2010_06_24_AMD_AFD_Sequence_Listing.txt," created on Jun. 24, 2010, and having a size of 5,141 bytes is hereby incorporated by reference pursuant to 37 C.F.R. §1.52(e)(5).

STATEMENT REGARDING FEDERALLY SPONSORED RESEARCH

This invention was made with government support under Grants NIH GM068819 awarded by the National Institutes of Health, and DARPA Grant No. W911NF-04-1-0416 awarded by the Army Research Office. The government has certain rights in the invention.

FIELD OF THE INVENTION

The disclosed invention is generally in the field of riboswitches and specifically in the area of modulation of riboswitch activation.

BACKGROUND OF THE INVENTION

Precision genetic control is an essential feature of living systems, as cells must respond to a multitude of biochemical signals and environmental cues by varying genetic expression patterns. Most known mechanisms of genetic control involve the use of protein factors that sense chemical or physical stimuli and then modulate gene expression by selectively interacting with the relevant DNA or messenger RNA sequence. Proteins can adopt complex shapes and carry out a variety of functions that permit living systems to sense accurately their chemical and physical environments. Protein factors that respond to metabolites typically act by binding DNA to modulate transcription initiation (e.g. the lac repressor protein; Matthews, K. S., and Nichols, J. C., 1998, Prog. Nucleic Acids Res. Mol. Biol. 58, 127-164) or by binding RNA to control either transcription termination (e.g. the PyrR protein; Switzer, R. L., et al., 1999, Prog. Nucleic Acids Res. Mol. Biol. 62, 329-367) or translation (e.g. the TRAP protein; Babitzke, P., and Gollnick, P., 2001, J. Bacteriol. 183, 5795-5802). Protein factors responds to environmental stimuli by various mechanisms such as allosteric modulation or post-translational modification, and are adept at exploiting these mechanisms to serve as highly responsive genetic switches (e.g. see Ptashne, M., and Gann, A. (2002). Genes and Signals. Cold Spring Harbor Laboratory Press, Cold Spring Harbor, N.Y.).

In addition to the widespread participation of protein factors in genetic control, it is also known that RNA can take an active role in genetic regulation. Recent studies have begun to reveal the substantial role that small non-coding RNAs play in selectively targeting mRNAs for destruction, which results in down-regulation of gene expression (e.g. see Hannon, G. J. 2002, Nature 418, 244-251 and references therein). This process of RNA interference takes advantage of the ability of short RNAs to recognize the intended mRNA target selectively via Watson-Crick base complementation, after which the bound mRNAs are destroyed by the action of proteins. RNAs are ideal agents for molecular recognition in this system because it is far easier to generate new target-specific RNA factors through evolutionary processes than it would be to generate protein factors with novel but highly specific RNA binding sites.

Although proteins fulfill most requirements that biology has for enzyme, receptor and structural functions, RNA also can serve in these capacities. For example, RNA has sufficient structural plasticity to form numerous ribozyme domains (Cech & Golden, Building a catalytic active site using only RNA. In: *The RNA World* R. F. Gesteland, T. R. Cech, J. F. Atkins, eds., pp. 321-350 (1998); Breaker, In vitro selection of catalytic polynucleotides. *Chem. Rev.* 97, 371-390 (1997)) and receptor domains (Osborne & Ellington, Nucleic acid selection and the challenge of combinatorial chemistry. *Chem. Rev.* 97, 349-370 (1997); Hermann & Patel, Adaptive recognition by nucleic acid aptamers. *Science* 287, 820-825 (2000)) that exhibit considerable enzymatic power and precise molecular recognition. Furthermore, these activities can be combined to create allosteric ribozymes (Soukup & Breaker, Engineering precision RNA molecular switches. *Proc. Natl. Acad. Sci. USA* 96, 3584-3589 (1999); Seetharaman et al., Immobilized riboswitches for the analysis of complex chemical and biological mixtures. *Nature Biotechnol.* 19, 336-341 (2001)) that are selectively modulated by effector molecules.

Bacterial riboswitch RNAs are genetic control elements that are located primarily within the 5'-untranslated region (5'-UTR) of the main coding region of a particular mRNA. Structural probing studies (discussed further below) reveal that riboswitch elements are generally composed of two domains: a natural aptamer (T. Hermann, D. J. Patel, *Science* 2000, 287, 820; L. Gold, et al., *Annual Review of Biochemistry* 1995, 64, 763) that serves as the ligand-binding domain, and an 'expression platform' that interfaces with RNA elements that are involved in gene expression (e.g. Shine-Dalgamo (SD) elements; transcription terminator stems).

BRIEF SUMMARY OF THE INVENTION

Disclosed herein are methods and compositions for screening for compounds that bind, activate and/or inactivate riboswitches. The methods and compositions are generally suitable for high throughput screening. The methods can, for example, identify compounds that can bind to riboswitches, identify trigger molecules for riboswitches with as yet unidentified trigger molecules, identify trigger molecules for putative riboswitches, identify a putative riboswitch as an functional riboswitch, and identify compounds that can deactivate, block and/or prevent or reduce activation of riboswitches (such compounds can be useful as antibiotics, for example). The compounds identified in the disclosed methods can be used, for example, to activate riboswitches (and thus affect RNA structure and modulate expression of expression sequences operatively linked to the riboswitches), compete for binding of the riboswitch (such as by displacing) the natural ligand of the riboswitch, and as a trigger molecule for riboswitches.

Also disclosed herein are methods comprising bringing into contact a ribozyme riboswitch, a substrate labeled with a conformation dependent label and a compound, wherein the substrate is a substrate for cleavage by the ribozyme riboswitch; and detecting change in fluorescence, wherein a change in fluorescence indicates cleavage of the substrate by the ribozyme riboswitch.

Cleavage of the substrate can indicate that the compound binds to the ribozyme riboswitch, that the compound activates the ribozyme riboswitch, that the compound interacts with the ribozyme riboswitch, or that the compound induces a conformational change in the ribozyme riboswitch. Cleavage of the substrate can also indicate that the compound is a trigger molecule for the ribozyme riboswitch.

The disclosed methods can be performed a plurality of times in parallel using a plurality of different compounds, wherein cleavage of the substrate in the presence of one of the compounds indicates that that compound activates the riboswitch. For example, the steps of the method disclosed above can be performed at least 20, 30, 40, 50, 75, 96, 100, 150, 200, 250, 300, 384, or 400 times in parallel. The steps can be performed a plurality of times in parallel a plurality of times in sequence. The steps can be performed a plurality of times in parallel at least 3, 5, 10, 15, 20, 30, 40, 50, 75, 100, 150, 200, 250, 300, or 400 times in sequence. The method disclosed herein can be performed a using a high throughput system.

A change in fluorescence can indicate that the compound modulates substrate cleavage. The conformation dependent label can be a Fluorescent Resonance Energy Transfer (FRET) label.

The ribozyme riboswitches can be naturally occurring, or can be engineered, such as a chimera. The chimera can comprise a riboswitch fused to a ribozyme, and in one example, can be self-cleaving. The ribozyme riboswitch can also be a naturally occurring ribozyme riboswitch that self-cleaves where a segment comprising the cleavage site is removed. In this case, the substrate can replace the removed segment. In one example, the riboswitch can be a guanine riboswitch, and the ribozyme can be a hammerhead ribozyme. The compounds to be screened can be a proteins or peptides. The compound can also comprise a small organic molecule.

Disclosed herein is a method comprising bringing into contact a riboswitch, a fluorescent trigger molecule and a compound; and detecting change in fluorescence, wherein a change in fluorescence indicates displacement of the trigger molecule from the riboswitch. Such displacement can occur via competitive binding of the compound. The riboswitch and trigger molecule can be brought into contact before the compound is brought into contact with the riboswitch and trigger molecule. The trigger molecule can be naturally fluorescent, or can comprise a fluorescent label.

Displacement of the trigger molecule from the riboswitch can indicate that the compound binds to the riboswitch. Displacement of the trigger molecule from the riboswitch can indicate that the compound deactivates, blocks and/or prevent or reduce activation the riboswitch. Displacement of the trigger molecule from the riboswitch can also indicate that the compound interacts with the riboswitch. Displacement of the trigger molecule from the riboswitch can also indicate that the compound induces a conformational change in the riboswitch.

The riboswitch can be an FMN riboswitch. The riboswitch can be naturally occurring, or can be engineered. The trigger molecule can be fluorescently active flavin mononucleotide. The compound can be a protein or peptide. The compound can also comprise a small organic molecule.

Disclosed herein are methods comprising bringing into contact a riboswitch and a compound, wherein the riboswitch comprises a conformation dependent label; and detecting change in fluorescence, wherein a change in fluorescence indicates a change in conformation of the riboswitch. The change in conformation of the riboswitch can indicate that the compound binds to the riboswitch. The change in conformation of the riboswitch can also indicate that the compound activates the riboswitch. The change in conformation of the riboswitch can also indicate that the compound interacts with the riboswitch. The change in conformation of the riboswitch can also indicate that the compound induces a conformational change in the riboswitch. The change in conformation of the riboswitch can also indicate that the compound is a trigger molecule for the riboswitch. The conformation dependent label can be a Fluorescent Resonance Energy Transfer (FRET) label.

The methods described herein can be performed a plurality of times in parallel using a plurality of different compounds, wherein displacement of the trigger molecule from the riboswitch in the presence of one of the compounds indicates that that compound deactivates or blocks the riboswitch. For example, the steps disclosed above can be performed at least 20, 30, 40, 50, 75, 96, 100, 150, 200, 250, 300, 384, or 400 times in parallel. The steps can be performed a plurality of times in parallel a plurality of times in sequence. The steps can be performed a plurality of times in parallel at least 3, 5, 10, 15, 20, 30, 40, 50, 75, 100, 150, 200, 250, 300, or 400 times in sequence. The method disclosed herein can be performed a using a high throughput system.

The riboswitch can be a $preQ_1$ riboswitch. The riboswitch can also be a guanine-responsive riboswitch. The riboswitch can also be a glycine-responsive riboswitch. The riboswitch can be a naturally occurring riboswitch to which a conformation dependent label has been added. The riboswitch can also be engineered. For example, the riboswitch can be a chimera. The compound can be a protein or peptide. The compound can also be, or can comprise, a small organic molecule.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
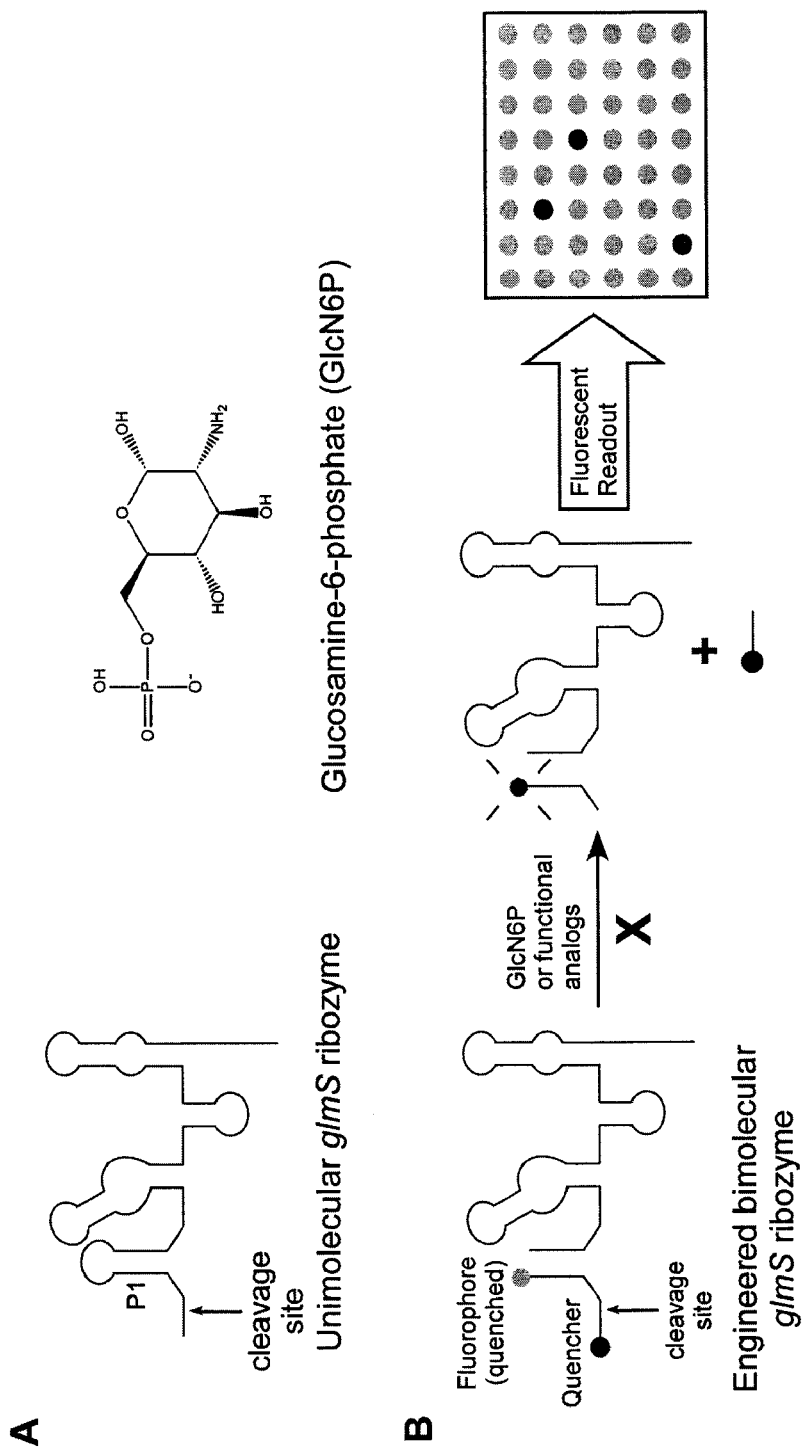
FIG. 1 shows the design of a high throughput screen by Method 1 of Example 1.A) The natural cis-cleaving glmS ribozyme cleaves at the site indicated by the arrow in the presence of Gln6P. B) A bimolecular glmS ribozyme for sensing the binding of novel functional analogs or mimics of Gln6P.

The disclosed methods and compositions can be understood more readily by reference to the following detailed description of particular embodiments and the Example included therein and to the Figures and their previous and following description.

1. Riboswitches

Certain natural mRNAs serve as metabolite-sensitive genetic switches wherein the RNA directly binds a small organic molecule. This binding process changes the conformation of the mRNA, which causes a change in gene expression by a variety of different mechanisms. Modified versions of these natural "riboswitches" (created by using various nucleic acid engineering strategies) can be employed as designer genetic switches that are controlled by specific effector compounds (referred to herein as trigger molecules). The natural riboswitches are targets for antibiotics and other small molecule therapies. In addition, the architecture of riboswitches allows pieces of the natural riboswitches to be used to construct new non-immunogenic genetic control elements, for example the expression platform can be substituted with a ribozyme (or otherwise modified) such that the aptamer domain modulates activity of the ribozyme.

Messenger RNAs are typically thought of as passive carriers of genetic information that are acted upon by protein- or small RNA-regulatory factors and by ribosomes during the process of translation. Certain mRNAs carry natural aptamer domains and binding of specific metabolites directly to these RNA domains leads to modulation of gene expression. Natural riboswitches exhibit two functions that are not typically associated with natural RNAs. First, the mRNA element can adopt distinct structural states wherein one structure serves as a precise binding pocket for its target metabolite. Second, the metabolite-induced allosteric interconversion between structural states causes a change in the level of gene expression by one of several distinct mechanisms. Natural riboswitches typically can be dissected into two separate domains: one that selectively binds the target (aptamer domain) and another that influences genetic control (expression platform). It is the dynamic interplay between these two domains that results in metabolite-dependent allosteric control of gene expression.

Distinct classes of riboswitches have been identified and are shown to selectively recognize activating compounds (referred to herein as trigger molecules). For example, coenzyme $B_{12}$, thiamine pyrophosphate (TPP), and flavin mononucleotide (FMN) activate riboswitches present in genes encoding key enzymes in metabolic or transport pathways of these compounds. The aptamer domain of each riboswitch class conforms to a highly conserved consensus sequence and structure. Thus, sequence homology searches can be used to identify related riboswitch domains. Riboswitch domains have been discovered in various organisms from bacteria, archaea, and eukarya. Riboswitches are described in U.S. Patent Application Publication No. US-2005-0053951, U.S. Pat. No. 6,831,171, PCT Application Publication No. WO 2006/055351, and U.S. Provisional Patent Application No. 60/625,864, each of which is hereby incorporated by reference in its entirety and for the description of riboswitches and their function.

i. General Organization of Riboswitch RNAs

Bacterial riboswitch RNAs are genetic control elements that are located primarily within the 5'-untranslated region (5'-UTR) of the main coding region of a particular mRNA. Structural probing studies (discussed further below) reveal that riboswitch elements are generally composed of two domains: a natural aptamer (T. Hermann, D. J. Patel, Science 2000, 287, 820; L. Gold, et al., *Annual Review of Biochemistry* 1995, 64, 763) that serves as the ligand-binding domain, and an 'expression platform' that interfaces with RNA elements that are involved in gene expression (e.g. Shine-Dalgamo (SD) elements; transcription terminator stems). These conclusions are drawn from the observation that aptamer domains synthesized in vitro bind the appropriate ligand in the absence of the expression platform. Moreover, structural probing investigations suggest that the aptamer domain of most riboswitches adopts a particular secondary- and tertiary-structure fold when examined independently, that is essentially identical to the aptamer structure when examined in the context of the entire 5' leader RNA. This implies that, in many cases, the aptamer domain is a modular unit that folds independently of the expression platform.

Ultimately, the ligand-bound or unbound status of the aptamer domain is interpreted through the expression platform, which is responsible for exerting an influence upon gene expression. The view of a riboswitch as a modular element is further supported by the fact that aptamer domains are highly conserved amongst various organisms (and even between kingdoms as is observed for the TPP riboswitch), (N. Sudarsan, et al., *RNA* 2003, 9, 644) whereas the expression platform varies in sequence, structure, and in the mechanism by which expression of the appended open reading frame is controlled. For example, ligand binding to the TPP riboswitch of the tenA mRNA of *B. subtilis* causes transcription termination (A. S. Mironov, et al., *Cell* 2002, 111, 747). This expression platform is distinct in sequence and structure compared to the expression platform of the TPP riboswitch in the thiM mRNA from *E. coli*, wherein TPP binding causes inhibition of translation by a SD blocking mechanism. The TPP aptamer domain is easily recognizable and of near identical functional character between these two transcriptional units, but the genetic control mechanisms and the expression platforms that carry them out are very different.

Aptamer domains for riboswitch RNAs typically range from ~70 to 170 nt in length. This observation was somewhat unexpected given that in vitro evolution experiments identified a wide variety of small molecule-binding aptamers, which are considerably shorter in length and structural intricacy (T. Hermann, D. J. Patel, *Science* 2000, 287, 820; L. Gold, et al., *Annual Review of Biochemistry* 1995, 64, 763; M. Famulok, *Current Opinion in Structural Biology* 1999, 9, 324). Although the reasons for the substantial increase in complexity and information content of the natural aptamer sequences relative to artificial aptamers remains to be proven, this complexity is most likely required to form RNA receptors that function with high affinity and selectivity. Apparent $K_D$ values for the ligand-riboswitch complexes range from low nanomolar to low micromolar. It is also worth noting that some aptamer domains, when isolated from the appended expression platform, exhibit improved affinity for the target ligand over that of the intact riboswitch. (~10 to 100-fold). Presumably, there is an energetic cost in sampling the multiple distinct RNA conformations required by a fully intact riboswitch RNA, which is reflected by a loss in ligand affinity. Since the aptamer domain must serve as a molecular switch, this might also add to the functional demands on natural aptamers that might help rationalize their more sophisticated structures.

ii. Riboswitch Regulation of Transcription Termination in Bacteria

Bacteria primarily make use of two methods for termination of transcription. Certain genes incorporate a termination signal that is dependent upon the Rho protein, (J. P. Richardson, *Biochimica et Biophysica Acta* 2002, 1577, 251). while others make use of Rho-independent terminators (intrinsic terminators) to destabilize the transcription elongation complex (I. Gusarov, E. Nudler, *Molecular Cell* 1999, 3, 495; E. Nudler, M. E. Gottesman, *Genes to Cells* 2002, 7, 755). The latter RNA elements are composed of a GC-rich stem-loop followed by a stretch of 6-9 uridyl residues. Intrinsic terminators are widespread throughout bacterial genomes (F. Lillo, et al., 2002, 18, 971), and are typically located at the 3'-termini of genes or operons. Interestingly, an increasing number of examples are being observed for intrinsic terminators located within 5'-UTRs.

Amongst the wide variety of genetic regulatory strategies employed by bacteria there is a growing class of examples wherein RNA polymerase responds to a termination signal within the 5'-UTR in a regulated fashion (T. M. Henkin, *Current Opinion in Microbiology* 2000, 3, 149). During certain conditions the RNA polymerase complex is directed by external signals either to perceive or to ignore the termination signal. Although transcription initiation might occur without regulation, control over mRNA synthesis (and of gene expression) is ultimately dictated by regulation of the intrinsic terminator. Presumably, one of at least two mutually exclusive mRNA conformations results in the formation or disruption of the RNA structure that signals transcription termination. A trans-acting factor, which in some instances is a RNA (F. J. Grundy, et al., *Proceedings of the National Academy of Sciences of the United States of America* 2002, 99, 11121; T. M. Henkin, C. Yanofsky, *Bioessays* 2002, 24, 700) and in others is a protein (J. Stulke, *Archives of Microbiology* 2002, 177, 433), is generally required for receiving a particular intracellular signal and subsequently stabilizing one of the RNA conformations. Riboswitches offer a direct link between RNA structure modulation and the metabolite signals that are interpreted by the genetic control machinery. A brief overview of the FMN riboswitch from a *B. subtilis* mRNA is provided below to illustrate this mechanism.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference to each of various individual and collective combinations and permutation of these compounds can not be explicitly disclosed, each is specifically contemplated and described herein. For example, if a riboswitch or aptamer domain is disclosed and discussed and a number of modifications that can be made to a number of molecules including the riboswitch or aptamer domain are discussed, each and every combination and permutation of riboswitch or aptamer domain and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Riboswitches

Riboswitches are expression control elements that are part of the RNA molecule to be expressed and that change state when bound by a trigger molecule. Riboswitches typically can be dissected into two separate domains: one that selectively binds the target (aptamer domain) and another that influences genetic control (expression platform domain). It is the dynamic interplay between these two domains that results in metabolite-dependent allosteric control of gene expression. Disclosed are isolated and recombinant riboswitches, recombinant constructs containing such riboswitches, heterologous sequences operably linked to such riboswitches, and cells and transgenic organisms harboring such riboswitches, riboswitch recombinant constructs, and riboswitches operably linked to heterologous sequences. The heterologous sequences can be, for example, sequences encoding proteins or peptides of interest, including reporter proteins or peptides. Preferred riboswitches are, or are derived from, naturally occurring riboswitches. As used herein, the term "riboswitch" refers to naturally occurring riboswitches, aptamer domains derived therefrom, and derivatives of naturally occurring riboswitches and aptamer domains derived therefrom. Riboswitches include naturally occurring riboswitches and their aptamer domains as well as sequence variants of naturally occurring riboswitches. Aptamers that are not derived from a naturally occurring riboswitches are not considered to be riboswitches herein. Aptamers that are not derived from a naturally occurring riboswitches can be referred to as non-riboswitch aptamers.

Activation of a riboswitch refers to the change in state of the riboswitch upon binding of a natural trigger molecule of the riboswitch. A riboswitch can be activated by compounds other than the trigger molecule and in ways other than binding of a trigger molecule. The term trigger molecule is used herein to refer to molecules and compounds that can activate a riboswitch. This includes the natural or normal trigger molecule for the riboswitch and other compounds that can activate the riboswitch.

Deactivation of a riboswitch refers to the change in state of the riboswitch when the trigger molecule is not bound. A riboswitch can be deactivated by binding of compounds other than the trigger molecule and in ways other than removal of the trigger molecule. Blocking of a riboswitch refers to a condition or state of the riboswitch where the presence of the trigger molecule does not activate the riboswitch.

The disclosed riboswitches, including the derivatives and recombinant forms thereof, generally can be from any source, including naturally occurring riboswitches and riboswitches designed de novo. Any such riboswitches can be used in or with the disclosed methods. However, different types of riboswitches can be defined and some such sub-types can be useful in or with particular methods (generally as described elsewhere herein). Types of riboswitches include, for example, naturally occurring riboswitches, derivatives and modified forms of naturally occurring riboswitches, chimeric riboswitches, engineered riboswitches, and recombinant riboswitches. A naturally occurring riboswitch is a riboswitch having the sequence of a riboswitch as found in nature. Such a naturally occurring riboswitch can be an isolated or recombinant form of the naturally occurring riboswitch as it occurs in nature. That is, the riboswitch has the same primary structure but has been isolated or engineered in a new genetic or nucleic acid context. Chimeric riboswitches can be made up of, for example, part of a riboswitch of any or of a particular class or type of riboswitch and part of a different riboswitch of the same or of any different class or type of riboswitch; part of a riboswitch of any or of a particular class or type of riboswitch and any non-riboswitch sequence or component; and part of a riboswitch (such as the aptamer domain) and a ribozyme. Engineered riboswitches are riboswitches that have portions removed and/or replaced by other sequences. Chimeric riboswitches are an example of engineered riboswitches. Recombinant riboswitches are riboswitches that have been isolated or engineered in a new genetic or nucleic acid context.

Different classes of riboswitches refer to riboswitches that have the same or similar trigger molecules or riboswitches that have the same or similar overall structure (predicted, determined, or a combination). Riboswitches of the same class generally, but need not, have both the same or similar trigger molecules and the same or similar overall structure.

Particularly useful aptamer domains can form a stem structure referred to herein as the P1 stem structure (or simply P1). The P1 stems of a variety of riboswitches are shown in FIG. 11 of U.S. Patent Application Publication No. US-2005-0053951. The hybridizing strands in the P1 stem structure are referred to as the aptamer strand (also referred to as the P1a strand) and the control strand (also referred to as the P1b strand). The control strand can form a stem structure with both the aptamer strand and a sequence in a linked expression platform that is referred to as the regulated strand (also referred to as the P1c strand). Thus, the control strand (P1b) can form alternative stem structures with the aptamer strand (P1a) and the regulated strand (P1c). Activation and deactivation of a riboswitch results in a shift from one of the stem structures to the other (from P1a/P1b to P1b/P1c or vice versa). The formation of the P1b/P1c stem structure affects expression of the RNA molecule containing the riboswitch. Riboswitches that operate via this control mechanism are referred to herein as alternative stem structure riboswitches (or as alternative stem riboswitches).

Also disclosed are chimeric riboswitches containing heterologous aptamer domains and expression platform domains. That is, chimeric riboswitches are made up an aptamer domain from one source and an expression platform domain from another source. The heterologous sources can be from, for example, different specific riboswitches, different types of riboswitches, or different classes of riboswitches. The heterologous aptamers can also come from non-riboswitch aptamers. The heterologous expression platform domains can also come from non-riboswitch sources.

Riboswitches can be modified from other known, developed or naturally-occurring riboswitches. For example, switch domain portions can be modified by changing one or more nucleotides while preserving the known or predicted secondary, tertiary, or both secondary and tertiary structure of the riboswitch. For example, both nucleotides in a base pair can be changed to nucleotides that can also base pair. Changes that allow retention of base pairing are referred to herein as base pair conservative changes.

Useful engineered riboswitches can be produced by operably linking an aptamer domain of a riboswitch to a ribozyme (which is a chimeric riboswitch). The aptamer domain can then modulate activity of the ribozyme through the action of, for example, a trigger molecule for the aptamer domain. Aptamer domains of riboswitches can be operably linked to ribozymes in any suitable manner, including, for example, by replacing all or part of the expression platform domain of the riboswitch with the ribozyme. Generally, any compound or condition that can activate, deactivate or block the riboswitch from which the aptamer domain is derived can be used to activate, deactivate or block the chimeric riboswitch (thus modulating the activity of the ribozyme). Chimeric riboswitches comprising a riboswitch operatively linked to a ribozyme can be referred to as a ribozyme riboswitch. Some naturally occurring riboswitches, such as the glmS riboswitch, include a ribozyme activity and thus are naturally occurring ribozyme riboswitches.

In general, any aptamer domain can be adapted for use with any ribozyme by designing or adapting a regulated strand in the ribozyme to be complementary to the control strand of the aptamer domain. Alternatively, the sequence of the aptamer and control strands of an aptamer domain can be adapted so that the control strand is complementary to a functionally significant sequence in a ribozyme. The function of such engineered ribozyme riboswitches can be easily assessed by activating the riboswitch with a trigger molecule and detecting cleavage by the ribozyme.

Disclosed are riboswitches, wherein the riboswitch is a non-natural derivative of a naturally-occurring riboswitch. The riboswitch can comprise an aptamer domain and an expression platform domain, wherein the aptamer domain and the expression platform domain are heterologous. The riboswitch can comprise an aptamer domain and a ribozyme. The riboswitch can comprise a conformation dependent label. The riboswitch can be derived from a naturally-occurring guanine-responsive riboswitch, adenine-responsive riboswitch, lysine-responsive riboswitch, thiamine pyrophosphate-responsive riboswitch, adenosylcobalamin-responsive riboswitch, flavin mononucleotide-responsive riboswitch, or a S-adenosylmethionine-responsive riboswitch. The riboswitch can be activated by a trigger molecule, wherein the riboswitch produces a signal when activated by the trigger molecule. Riboswitches are described in U.S. Patent Application Publication No. US-2005-0053951, U.S. Pat. No. 6,831,171, PCT Application Publication No. WO 2006/055351, and U.S. Provisional Patent Application No. 60/625,864, each of which is hereby incorporated by reference in its entirety and for the description of riboswitches and their function.

Numerous riboswitches and riboswitch constructs are known and are described and referred to herein. It is specifically contemplated that any specific riboswitch or riboswitch construct or group of riboswitches or riboswitch constructs can be excluded from some aspects of the invention disclosed herein. For example, fusion of the xpt-pbuX riboswitch with a reporter gene could be excluded from a set of riboswitches fused to reporter genes.

1. Aptamer Domains

Aptamers are nucleic acid segments and structures that can bind selectively to particular compounds and classes of compounds. Riboswitches have aptamer domains that, upon binding of a trigger molecule result in a change the state or structure of the riboswitch. In functional riboswitches, the state or structure of the expression platform domain linked to the aptamer domain changes when the trigger molecule binds to the aptamer domain. Aptamers in riboswitches generally have at least one portion that can interact, such as by forming a stem structure, with a portion of the linked expression platform domain. This stem structure will either form or be disrupted upon binding of the trigger molecule.

Consensus aptamer domains of a variety of natural riboswitches are shown in FIG. 11 of U.S. Patent Application Publication No. US-2005-0053951, which is hereby incorporated by reference. These aptamer domains (including all of the direct variants embodied therein) can be used in riboswitches. The consensus sequences and structures indicate variations in sequence and structure. Aptamer domains that are within the indicated variations are referred to herein as direct variants. These aptamer domains can be modified to produce modified or variant aptamer domains. Conservative modifications include any change in base paired nucleotides such that the nucleotides in the pair remain complementary. Moderate modifications include changes in the length of stems or of loops (for which a length or length range is indicated) of less than or equal to 20% of the length range indicated. Loop and stem lengths are considered to be "indicated" where the consensus structure shows a stem or loop of a particular length or where a range of lengths is listed or depicted. Moderate modifications include changes in the length of stems or of loops (for which a length or length range is not indicated) of less than or equal to 40% of the length range indicated. Moderate modifications also include and functional variants of unspecified portions of the aptamer domain. Unspecified portions of the aptamer domains are indicated by solid lines in FIG. 11 of U.S. Patent Application Publication No. US-2005-0053951.

The P1 stem and its constituent strands can be modified in adapting aptamer domains for use with expression platforms and RNA molecules. Such modifications, which can be extensive, are referred to herein as P1 modifications. P1 modifications include changes to the sequence and/or length of the P1 stem of an aptamer domain.

Aptamer domains of the disclosed riboswitches can also be used for any other purpose, and in any other context, as aptamers. For example, aptamers can be used in the disclosed riboswitch composition for use in the disclosed methods, to control ribozymes, other molecular switches, and any RNA molecule where a change in structure can affect function of the RNA.

2. Expression Platform Domains

Expression platform domains are a part of riboswitches that affect expression of the RNA molecule that contains the riboswitch. Expression platform domains generally have at least one portion that can interact, such as by forming a stem structure, with a portion of the linked aptamer domain. This stem structure will either form or be disrupted upon binding of the trigger molecule. The stem structure generally either is, or prevents formation of, an expression regulatory structure. An expression regulatory structure is a structure that allows, prevents, enhances or inhibits expression of an RNA molecule containing the structure. Examples include Shine-Dalgarno sequences, initiation codons, transcription terminators, and stability and processing signals.

B. Trigger Molecules

Trigger molecules are molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

C. Compounds

The disclosed methods screen compounds for their effect on riboswitches. Any compound can be used with (and screened by) the disclosed methods. The compounds can be, for example, proteins, peptides and small organic molecules. As used herein, a small organic molecule is an organic molecule having a molecular weight of less than 1000 Daltons. The methods can, for example, identify compounds that can bind to riboswitches, identify trigger molecules for riboswitches with as yet unidentified trigger molecules, identify trigger molecules for putative riboswitches, identify a putative riboswitch as an functional riboswitch, and identify compounds that can deactivate, block and/or prevent or reduce activation of riboswitches (such compounds can be useful as antibiotics, for example). The compounds identified in the disclosed methods can be used, for example, to activate riboswitches (and thus affect RNA structure and modulate expression of expression sequences operatively linked to the riboswitches), compete for binding of the riboswitch (such as by displacing) the natural ligand of the riboswitch, and as a trigger molecule for riboswitches.

Disclosed are compounds, and compositions containing such compounds, that can bind, modulate, activate, deactivate or block a riboswitch, and/or that can compete with the trigger molecule for riboswitch binding. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. A riboswitch can be blocked by, for example, binding of an analog of the trigger molecule that does not activate the riboswitch. The disclosed methods can be used to identify compounds having such effects on riboswitches.

The identified compounds can be used for altering expression of an RNA molecule, or of a gene encoding an RNA molecule, where the RNA molecule includes a riboswitch. This can be accomplished by bringing the compound into contact with the RNA molecule. Riboswitches function to control gene expression through the binding or removal of a trigger molecule. Thus, subjecting an RNA molecule of interest that includes a riboswitch to conditions that modulate, activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

The identified compounds can be used for regulating expression of an RNA molecule, or of a gene encoding an RNA molecule. The identified compounds can be used for regulating expression of a naturally occurring gene or RNA that contains a riboswitch by activating, deactivating or blocking the riboswitch. If the gene is essential for survival of a cell or organism that harbors it, activating, deactivating or blocking the riboswitch can in death, stasis or debilitation of the cell or organism.

The identified compounds can be used for regulating expression of an isolated, engineered or recombinant gene or RNA that contains a riboswitch by modulating, activating, deactivating or blocking the riboswitch. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules.

D. Fluorescent Labels

To aid in detection and quantitation of riboswitch activation, deactivation or blocking, modulation, or expression of nucleic acids or protein produced upon activation, modulation, deactivation or blocking of riboswitches, fluorescent labels can be used. For example, fluorescent labels an be used in conformation dependent labels. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—$CH_3$, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Useful fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a useful form of detection label for direct incorporation into nucleic acids during synthesis. Examples of detection labels that can be incorporated into nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951: 157-165 (1988)), bromouridine (Wansick et al., *J Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (bromodeoxyuridine, BrdUrd, BrdU, BUdR, Sigma-Aldrich Co). Other useful nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A useful nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Flavin mononucleotide (FMN), also known as riboflavin-5'-phosphate, has been characterized as an indirect laser-induced fluorescence (LIF) detection reagent for inorganic anions, organic acids, anionic surfactants and polyphosphates after separation by capillary electrophoresis (CE). FMN provides a good wavelength match for laser excitation at 488 nm, is readily soluble in aqueous or aqueous/organic solutions, and unlike fluorescein provides strong fluorescence at both acidic and basic pH values. Analyte peaks due to a loss in FMN fluorescence are generated at weakly alkaline pH values as expected, but peak direction is switched at more alkaline pH values such as 8.6 or 9.0. A separation of 21 inorganic anions and organic acids is possible in about 20 min using the indirect LIF mode using 10 µM FMN with 2 mM diethylenetriamine as the electroosmotic flow suppressor. Detection limits for these analytes are in the 10-20 µg/l range without any required preconcentration. FMN is the trigger molecule for FMN riboswitches and can be used as described elsewhere herein as a fluorescent trigger molecule.

1. Conformation Dependent Labels

Conformation dependent labels refer to all labels that produce a change in fluorescence intensity or wavelength based on a change in the form or conformation of the molecule or compound (such as a riboswitch) with which the label is associated. Examples of conformation dependent labels used in the context of probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, fluorescent nucleoside analogs, PNA probes and QPNA probes. Such labels, and, in particular, the principles of their function, can be adapted for use with riboswitches. Several types of conformation dependent labels are reviewed in Schweitzer and Kingsmore, Curr. Opin. Biotech. 12:21-27 (2001). As used herein, a FRET label refers to a FRET pair that produces a change in fluorescence based on a change in the form or conformation of the molecule or compound (such as a riboswitch) with which the label is associated.

Stem quenched labels, a form of conformation dependent labels, are fluorescent labels positioned on a nucleic acid such that when a stem structure forms a quenching moiety is brought into proximity such that fluorescence from the label is quenched. When the stem is disrupted (such as when a riboswitch containing the label is activated or a substrate is cleaved by a ribozyme), the quenching moiety is no longer in proximity to the fluorescent label and fluorescence increases. Examples of this effect can be found in molecular beacons, fluorescent triplex oligos, triplex molecular beacons, triplex FRET probes, and QPNA probes, the operational principles of which can be adapted for use with riboswitches.

Stem activated labels, a form of conformation dependent labels, are labels or pairs of labels where fluorescence is increased or altered by formation of a stem structure. Stem activated labels can include an acceptor fluorescent label and a donor moiety such that, when the acceptor and donor are in proximity (when the nucleic acid strands containing the labels form a stem structure), fluorescence resonance energy transfer from the donor to the acceptor causes the acceptor to fluoresce. Stem activated labels are typically pairs of labels positioned on nucleic acid molecules (such as riboswitches or substrates for ribozymes) such that the acceptor and donor are brought into proximity when a stem structure is formed in the nucleic acid molecule. If the donor moiety of a stem activated label is itself a fluorescent label, it can release energy as fluorescence (typically at a different wavelength than the fluorescence of the acceptor) when not in proximity to an acceptor (that is, when a stem structure is not formed). When the stem structure forms, the overall effect would then be a reduction of donor fluorescence and an increase in acceptor fluorescence. FRET probes are an example of the use of stem activated labels, the operational principles of which can be adapted for use with riboswitches.

Similar principles of quenching can apply to fluorescent trigger molecules. Thus, fluorescent trigger molecules, such as FMN and guanine, can change in fluorescence when displaced from riboswitches.

E. Ribozymes

Ribozymes can be used with the disclosed compositions and methods. For example, ribozymes can be used in chimeric and engineered ribozyme riboswitches. In such ribozyme riboswitches the activity of the ribozyme portion can be modulated by the riboswitch portion. Ribozyme activity can be increased upon riboswitch activation or decreased upon riboswitch activation, depending on the type of riboswitch and the nature of the integration of the ribozyme and riboswitch. Ribozymes are nucleic acid molecules that are capable of catalyzing a chemical reaction, either intramolecularly or intermolecularly. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

F. Solid Supports

Solid supports are solid-state substrates or supports with which or into which compounds, molecules (such as trigger molecules) and riboswitches (or other components used in, or produced by, the disclosed methods) can be associated or placed. Riboswitches and other molecules can be associated with solid supports directly or indirectly. For example, analytes (e.g., trigger molecules, test compounds) can be bound to the surface of a solid support or associated with capture agents (e.g., compounds or molecules that bind an analyte) immobilized on solid supports. As another example, riboswitches can be bound to the surface of a solid support or associated with probes immobilized on solid supports. An array is a solid support to which multiple riboswitches, probes or other molecules have been associated in an array, grid, or other organized pattern. Solid supports are useful for high throughput forms of the disclosed methods.

Solid-state substrates for use in solid supports can include any solid material with which components can be associated, directly or indirectly, or into which components can be placed. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, plates, fibers, woven fibers, shaped polymers, particles, beads, microparticles, or a combination. Solid-state substrates and solid supports can be porous or non-porous. A chip is a rectangular or square small piece of material. Preferred forms for solid-state substrates are dishes and plates. A useful form for a solid-state substrate is a microtiter dish. In some embodiments, a multiwell glass slide can be employed.

An array can include a plurality of riboswitches, trigger molecules, other molecules, compounds or probes immobilized or located at identified or predefined locations on the solid support. For screening of compounds it is useful to have a plurality of compounds located at identified or predefined locations on the solid support. In such cases, it is also useful to use the same other components in conjunction with each of the plurality of different compounds. For example, it is useful to use the same riboswitch with each of the different compounds to be screened. Each predefined location on the solid support generally has one type of component (that is, all the components at that location are the same). Alternatively, multiple types of components can be immobilized or located in the same predefined location on a solid support. Each location will have multiple copies of the given components. The spatial separation of different components on the solid support allows separate detection and identification.

Although useful, it is not required that the solid support be a single unit or structure. A set of riboswitches, trigger molecules, other molecules, compounds and/or probes can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730 (1991). A method for immobilization of 3'-amine oligonucleotides on casein-coated slides is described by Stimpson et al., *Proc. Natl. Acad. Sci. USA* 92:6379-6383 (1995). A useful method of attaching oligonucleotides to solid-state substrates is described by Guo et al., *Nucleic Acids Res.* 22:5456-5465 (1994).

Each of the components (for example, riboswitches, trigger molecules, or other molecules) on or in the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting compounds, the kit comprising one or more riboswitches. The kits also can contain reagents and labels for detecting activation of the riboswitches.

H. Mixtures

Disclosed are mixtures formed by performing or preparing to perform the disclosed methods. For example, disclosed are mixtures comprising riboswitches and trigger molecules. Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

I. Systems

Disclosed are systems useful for performing, or aiding in the performance of, the disclosed methods. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising riboswitches, a solid support and a signal-reading device.

J. Data Structures and Computer Control

Disclosed are data structures used in, generated by, or generated from, the disclosed method. Data structures generally are any form of data, information, and/or objects collected, organized, stored, and/or embodied in a composition or medium. Riboswitch structures and activation measurements stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Methods

Disclosed herein are methods for screening for compounds that bind, activate and/or inactivate riboswitches. The methods and compositions are generally suitable for high throughput screening. The methods can, for example, identify compounds that can bind to riboswitches, identify trigger molecules for riboswitches with as yet unidentified trigger molecules, identify trigger molecules for putative riboswitches, identify a putative riboswitch as an functional riboswitch, and identify compounds that can deactivate, block and/or prevent or reduce activation of riboswitches (such compounds can be useful as antibiotics, for example). The compounds identified in the disclosed methods can be used, for example, to activate riboswitches (and thus affect RNA structure and modulate expression of expression sequences operatively linked to the riboswitches), compete for binding of the riboswitch (such as by displacing) the natural ligand of the riboswitch, as a trigger molecule for riboswitches, and to deactivate or block riboswitches. Compounds that deactivate or block riboswitches can be used, for example, as antibiotics.

The disclosed methods also can be used, for example, to identify novel compounds that bind to known riboswitch elements, to identify proteins that bind to known riboswitch elements, to identify compounds that bind to putative riboswitch elements whose natural cognate effector (trigger molecule) is not known, and to identify potential antimicrobial compounds whose antibiotic activity is linked to riboswitch binding.

A. Methods 1 and 2

In some forms, the disclosed methods comprise bringing into contact a ribozyme riboswitch, a substrate labeled with a conformation dependent label and a compound, wherein the substrate is a substrate for cleavage by the ribozyme riboswitch; and detecting change in fluorescence, wherein a change in fluorescence indicates cleavage of the substrate by the ribozyme riboswitch. Examples of this form of the disclosed methods are described in sections 1 and 2 of the Examples.

Cleavage of the substrate can indicate that the compound binds to the ribozyme riboswitch, that the compound activates the ribozyme riboswitch, that the compound interacts with the ribozyme riboswitch, or that the compound induces a conformational change in the ribozyme riboswitch. Cleavage of the substrate can also indicate that the compound is a trigger molecule for the ribozyme riboswitch. A change in fluorescence can indicate that the compound modulates substrate cleavage. The conformation dependent label can be a Fluorescent Resonance Energy Transfer (FRET) label. The compounds to be screened can be a proteins or peptides. The compound can also comprise a small organic molecule.

The ribozyme riboswitches can be naturally occurring, or can be engineered, such as a chimera. The chimera can comprise a riboswitch fused to a ribozyme, and in one example, can be self-cleaving. In one example, the riboswitch can be a guanine riboswitch, and the ribozyme can be a hammerhead ribozyme. The ribozyme riboswitch can be a naturally occurring ribozyme riboswitch that self-cleaves.

A segment of the ribozyme riboswitch comprising the cleavage site can be removed. In this case, the substrate can replace the removed segment. Removal of a segment of a ribozyme comprising the cleavage site has been done with numerous ribozymes. This allows the ribozyme to cleave substrate sequences in trans. Such changes, and the principles involved, can be with the disclosed ribozymes and ribozyme riboswitches to produce trans-cleaving ribozymes and ribozyme riboswitches for use in the disclosed methods. The disclosed methods can also use ribozymes with similar changes to allow cleavage of a substrate. The substrate can comprise a conformation dependent label. Alternatively, the segment comprising the cleavage site in a self-cleaving ribozyme riboswitch can be engineered to comprise a conformation dependent label. Self-cleavage of the ribozyme riboswitch can then result in a change in fluorescence based on separation of a labeled segment upon cleavage. As used herein in the context of ribozymes and ribozyme riboswitches, a substrate if a nucleic acid segment that comprises a cleavage site for the ribozyme or ribozyme riboswitch. The substrate can be a part of or covalently coupled to the ribozyme or ribozyme riboswitch or can be a separate molecule.

An example of a naturally occurring ribozyme riboswitch is the glmS ribozyme. It is a cis-cleaving catalytic riboswitch located in the 5'-UTR of bacterial mRNA that codes for glucosamine-6-phosphate synthetase. The ribozyme can be specifically activated for glmS-mRNA cleavage by the metabolite glucosamine-6-phosphate (GlcN6P), that is, the metabolic product of the glmS-encoded protein itself. This complex regulation thus relies on a feedback-inhibition mechanism that senses the presence of metabolites that serve as cell-wall precursors. The ribozyme exhibits remarkable sensitivity and specificity for GlcN6P; related metabolites, such as glucose, glucose-6-phosphate or glucosamine (GlcN), cannot activate it. On the other hand, if small molecules can be found that activate the ribozyme in an analogous fashion to GlcN6P, they are likely to exhibit antibiotic activity because they trigger destruction of the mRNA that encodes for a protein required for the synthesis of a bacterial cell-wall precursor molecule (Mayer et al, ChemBioChem 2006, 7, 602-604).

B. Method 3

In some forms, the disclosed methods comprise bringing into contact a riboswitch, a fluorescent trigger molecule and a compound; and detecting change in fluorescence, wherein a change in fluorescence indicates displacement of the trigger molecule from the riboswitch. Such displacement can occur via competitive binding of the compound. The riboswitch and trigger molecule can be brought into contact before, at the same time, or after the compound is brought into contact with the riboswitch and trigger molecule. The trigger molecule can be naturally fluorescent, or can comprise a fluorescent label. FMN and guanine are examples of naturally fluorescent trigger molecules. An example of this form of the disclosed methods is described in section 3 of the Examples.

Displacement of the trigger molecule from the riboswitch can indicate that the compound binds to the riboswitch. Displacement of the trigger molecule from the riboswitch can indicate that the compound deactivates, blocks and/or prevent or reduce activation the riboswitch. Displacement of the trigger molecule from the riboswitch can also indicate that the compound interacts with the riboswitch. Displacement of the trigger molecule from the riboswitch can also indicate that the compound induces a conformational change in the riboswitch. The riboswitch can be naturally occurring, or can be engineered. The trigger molecule can be fluorescently active flavin mononucleotide. The compound can be a protein or peptide. The compound can also comprise a small organic molecule.

The riboswitch can be an FMN riboswitch. A highly conserved RNA domain, referred to as the RFN element, was identified in bacterial genes involved in the biosynthesis and transport of riboflavin and FMN (M. S. Gelfand, et al., *Trends in Genetics* 1999, 15, 439; A. G. Vitreschak, et al., *Nucleic Acids Research* 2002, 30, 3141). This element is required for genetic manipulation of the ribDEAHT operon (hereafter, 'ribD') of *B. subtilis*, as mutations resulted in a loss of FMN-mediated regulation (Y. V. Kil, et al., *Molecular & General Genetics* 1992, 233, 483; V. N. Mironov, et al., *Molecular & General Genetics* 1994, 242, 201). ribD RNA contains a saturable ligand-binding site that exhibits an apparent $K_D$ of ~5 nM. Furthermore, the RNA discriminates against the dephosphorylated form of FMN (riboflavin) by approximately three orders of magnitude. This exceptional ligand specificity of the ribD mRNA is surprising since the aptamer must generate a binding pocket for FMN that makes productive interactions with a phosphate group. FMN directly interacts with ribD transcripts during conditions of excess FMN. Complex formation subsequently induces transcription termination within the 5'-UTR (FIG. 12), which precludes gene expression by preventing the ORF from being transcribed. During conditions of limiting FMN, an antiterminator structure is formed within the ribD nascent transcript, which allows for synthesis of the downstream genes.

C. Method 4

In some forms, the disclosed methods comprise bringing into contact a riboswitch and a compound, wherein the riboswitch comprises a conformation dependent label; and detecting change in fluorescence, wherein a change in fluorescence indicates a change in conformation of the riboswitch. The change in conformation of the riboswitch can indicate that the compound binds to the riboswitch. The change in conformation of the riboswitch can also indicate that the compound activates the riboswitch. The change in conformation of the riboswitch can also indicate that the compound interacts with the riboswitch. The change in conformation of the riboswitch can also indicate that the compound induces a conformational change in the riboswitch. The change in conformation of the riboswitch can also indicate that the compound is a trigger molecule for the riboswitch. The conformation dependent label can be a Fluorescent Resonance Energy Transfer (FRET) label. An example of this form of the disclosed methods is described in section 4 of the Examples.

The riboswitch can be naturally occurring to which a conformation dependent label has been added. The riboswitch can also be engineered. For example, the riboswitch can be a chimera. The addition of a conformation dependent label to a riboswitch can be accomplished, for example, by incorporating a fluorescent label or moiety in the riboswitch. The location for the fluorescent label can be chosen to be a location where the conformation of the riboswitch changes upon activation. For example, the fluorescent label can be located in a stem that is formed or disrupted upon riboswitch activation or in a loop that its position or conformation. The function of such labels in riboswitches can be easily assessed by activating the riboswitch with a trigger molecule. The structure and conformational changes of riboswitches are either known or can be determined using techniques described in U.S. Patent Application Publication No. US-2005-0053951.

The riboswitch can be a preQ1 riboswitch. The riboswitch can also be a guanine-responsive riboswitch. The riboswitch can also be a glycine-responsive riboswitch. The compound disclosed herein can be a protein or peptide. The compound can also be, or can comprise, a small organic molecule.

D. High Throughput Screening

The disclosed methods can be used to screen a large number of compounds and such screening can be performed in a high throughput manner. As used herein, high throughput screening refers to methods that involve screening 20 or more compounds or samples simultaneously or in parallel or that involve automated screening of 20 or more compounds or samples sequentially, simultaneously or in parallel. Efficient screening techniques can involve, for example, rapid screening of a few or single compounds or samples in sequence, screening of numerous compounds in parallel (such as methods using multiwell plates, and sequentially screening groups of compounds that are screened in parallel. For example, a number of compounds can be screened simultaneously (such as in a multiwell plate) and multiple such screening can be performed sequentially. Thus, for example, the disclosed methods can be performed a plurality of times in parallel using a plurality of different compounds, wherein displacement of the trigger molecule from the riboswitch in the presence of one of the compounds indicates that that compound deactivates or blocks the riboswitch. For example, the steps disclosed above can be performed at least 20, 30, 40, 50, 75, 96, 100, 150, 200, 250, 300, 384, or 400 times in parallel. The steps can be performed a plurality of times in parallel a plurality of times in sequence. The steps can be performed a plurality of times in parallel at least 3, 5, 10, 15, 20, 30, 40, 50, 75, 100, 150, 200, 250, 300, or 400 times in sequence.

The method disclosed herein can be performed a using a high throughput system. Numerous techniques, apparatus and systems for automated and/or high throughput screening are known. Such techniques, apparatus and systems can be used to perform the disclosed methods.

E. Making and Using Identified Compounds

Also disclosed are compounds made by identifying a compound that activates, interacts with, modulates, deactivates or blocks a riboswitch and manufacturing the identified compound. This can be accomplished by, for example, combining compound identification methods as disclosed elsewhere herein with methods for manufacturing the identified compounds. For example, compounds can be made by bringing into contact a test compound and a riboswitch, assessing activation of the riboswitch, and, if the riboswitch is activated by the test compound, manufacturing the test compound that activates the riboswitch as the compound.

Also disclosed are compounds made by checking modulation, activation, deactivation or blocking of a riboswitch by a compound and manufacturing the checked compound. This can be accomplished by, for example, combining compound activation, deactivation or blocking assessment methods as disclosed elsewhere herein with methods for manufacturing the checked compounds. For example, compounds can be made by bringing into contact a test compound and a riboswitch, assessing activation of the riboswitch, and, if the riboswitch is activated by the test compound, manufacturing the test compound that activates the riboswitch as the compound. Checking compounds for their ability to activate, deactivate or block a riboswitch refers to both identification of compounds previously unknown to activate, deactivate or block a riboswitch and to assessing the ability of a compound to activate, deactivate or block a riboswitch where the compound was already known to activate, deactivate or block the riboswitch.

Also disclosed are compositions and methods for regulating expression of a naturally occurring gene or RNA that contains a riboswitch by activating, deactivating or blocking the riboswitch. If the gene is essential for survival of a cell or organism that harbors it, activating, deactivating or blocking the riboswitch can in death, stasis or debilitation of the cell or organism. For example, activating a naturally occurring riboswitch in a naturally occurring gene that is essential to survival of a microorganism can result in death of the microorganism (if activation of the riboswitch turns off or represses expression). This is one basis for the use of the disclosed compounds and methods for antimicrobial and antibiotic effects. The compounds identified using the disclosed methods can be used for this purpose.

Also disclosed are compositions and methods for regulating expression of an isolated, engineered or recombinant gene or RNA that contains a riboswitch by activating, deactivating or blocking the riboswitch. The gene or RNA can be engineered or can be recombinant in any manner. For example, the riboswitch and coding region of the RNA can be heterologous, the riboswitch can be recombinant or chimeric, or both. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules. The compounds identified using the disclosed methods can be used for this purpose.

Also disclosed are compositions and methods for inactivating a riboswitch by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule. The compounds identified using the disclosed methods can be used for this purpose.

F. Fluorescent Detection

The disclosed methods can use fluorescent labels for detection of, for example, binding, activation, and conformational changes in riboswitches. Particularly useful are conformation dependent labels. Conformation dependent labels can be detected based on a change in fluorescence. Such a change can involve, for example, fluorescent resonance energy transfer (FRET) or a change in quenching of fluorescence form a fluorescent label. Useful detection techniques are described in U.S. Patent Application Publication No. 2003165846 and PCT Application Publication No, WO 2002/083953.

1. Fluorescent Resonance Energy Transfer

A fluorescent indicator that utilizes fluorescent resonance energy transfer ("FRET") to measure the concentration of an analyte includes two fluorescent moieties having emission and excitation spectra that render one a donor fluorescent moiety and the other an acceptor fluorescent moiety. The fluorescent moieties are chosen such that the excitation spectrum of one of the moieties (the acceptor fluorescent moiety) overlaps with the emission spectrum of the excited moiety (the donor fluorescent moiety). The donor and acceptor fluorescent moieties are bound to a binding moiety that changes conformation upon binding the analyte. The change in conformation leads to a change in relative position and orientation of the donor and acceptor fluorescent moieties, thereby altering the relative amounts of fluorescence from the two fluorescent moieties when the donor is excited by irradiation. In particular, binding of the analyte changes the ratio of the amount of light emitted by the donor and acceptor fluorescent moieties. The ratio between the two emission wavelengths provides a measure of the concentration of the analyte in the sample, which is based in part on the binding affinity of the binding moiety and the analyte. As used herein, a FRET label refers to a FRET pair that produces a change in fluorescence based on a change in the form or conformation of the molecule or compound (such as a riboswitch) with which the label is associated.

The donor fluorescent moiety is covalently linked to a first region of the binding moiety, and the acceptor fluorescent moiety is covalently linked to a second region of the binding moiety such that the donor and acceptor moieties move closer together upon binding the analyte. Alternatively, the donor and acceptor moieties can move farther apart upon binding the analyte. The donor moiety is excited by light of appropriate intensity within the excitation spectrum of the donor moiety. The donor moiety emits the absorbed energy as fluorescent light. When the acceptor fluorescent moiety is positioned to quench the donor moiety in the excited state, the fluorescence energy is transferred to the acceptor moiety which can emit fluorescent light. FRET can be manifested as a reduction in the intensity of the fluorescent signal from the donor moiety, reduction in the lifetime of the excited state of the donor moiety, or emission of fluorescent light at the longer wavelengths (lower energies) characteristic of the acceptor moiety. When the conformation of the binding moiety changes upon binding the analyte, the fluorescent moieties come closer together (or physically separate), and FRET is increased (or decreased) accordingly.

The efficiency of FRET depends on the separation distance and the orientation of the donor and acceptor fluorescent moieties. For example, the Forster equation describes the efficiency of excited state energy transfer, based in part on the fluorescence quantum yield of the donor moiety and the energetic overlap with the acceptor moiety. The Forster equation is: $E=(F_0-F)/F_0=R_0^6/(R^6+R_0^6)$ where E is the efficiency of FRET, F and $R_0$ are the fluorescence intensities of the donor moiety in the presence and absence of the acceptor, respectively, and R is the distance between the donor moiety and the acceptor moiety.

The characteristic distance $R_0$ at which FRET is 50% efficient depends on the quantum yield of the donor moiety (i.e., the shorter-wavelength fluorophore), the extinction coefficient of the acceptor moiety (i.e., the longer-wavelength fluorophore), and the overlap between the emission spectrum of the donor moiety and the excitation spectrum of the acceptor moiety. $R_0$ is given (in Å) by $R_0=9.79\times10^3 \,(K^2QJn^{-4})^{1/6}$ where $K^2$ is an orientation factor having an average value close to 0.67 for freely mobile donors and acceptors, Q is the quantum yield of the unquenched donor moiety, n is the refractive index of the medium separating the donor moiety and the acceptor moiety, and J is the overlap integral. J can be quantitatively expressed as the degree of spectral overlap between the donor moiety and the acceptor moiety. See, for example, Forster, T. Ann. Physik 2:55-75 (1948). Tables of spectral overlap integrals are readily available to those working in the field (for example, Berlman, I. B. Energy transfer parameters of aromatic compounds, Academic Press, N.Y. and London (1973)). FRET is a nondestructive spectroscopic method that can monitor proximity and relative angular orientation of fluorophores in living cells. See, for example, Adams, S. R., et al., Nature 349:694-697 (1991), and Gonzalez, J. & Tsien, R. Y. Biophy. J. 69:1272-1280 (1995).

The donor fluorescent moiety can be excited by ultraviolet (<400 nm) and emits blue light (<500 nm), and the acceptor fluorescent moiety is efficiently excited by blue but not by ultraviolet light and emits green light (>500 nm), for example, P4-3 and S65T, respectively. Alternatively, the donor fluorescent moiety can be excited by violet (400-430 nm) and emits blue-green (450-500 nm) and the acceptor fluorescent moiety is efficiently excited by blue-green (450-500 nm) and emits yellow-green light (.gtoreq.520 nm), for example WIB and 10C respectively.

The amount of analyte in a sample can be determined by determining the degree of FRET in the sample. Changes in analyte concentration can be determined by monitoring FRET at a first and second time after contact between the sample and the fluorescent indicator and determining the difference in the degree of FRET. The amount of analyte in the sample can be calculated by using a calibration curve established by titration. The degree of FRET can be determined by any spectral or fluorescence lifetime characteristic of the excited donor moiety. For example, intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor can be monitored.

Changes in the degree of FRET can be determined as a function of the change in the ratio of the amount of fluorescence from the donor and acceptor moieties, a process referred to as "ratioing." Changes in the absolute amount of indicator, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of label separation than either intensity alone.

Fluorescence in a sample can be measured using a fluorometer. In general, excitation radiation, from an excitation source having a first wavelength, passes through excitation optics. The excitation optics cause the excitation radiation to excite the sample. In response, fluorescent molecules in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

The excited state lifetime of the donor moiety is, likewise, independent of the absolute amount of substrate, excitation intensity, or turbidity or other background absorbances. Its measurement requires equipment with nanosecond time resolution.

Quantum yields of wild-type GFP, S65T, and P4-1 mutants can be estimated by comparison with fluorescein in 0.1 N NaOH as a standard of quantum yield 0.91. J. N. Miller, ed., Standards in Fluorescence Spectrometry, New York: Chapman and Hall (1981). Mutants P4 and P4-3 were likewise compared to 9-aminoacridine in water (quantum yield 0.98).

EXAMPLES

A. Example 1

Characterizing Ligands that Modulate the Activity of Riboswitches

1. Method 1: Use of FRET to Detect Substrate Cleavage by Natural Ribozyme Riboswitches The naturally occurring glmS RNA element catalyzes self-cleavage in the presence of modest concentrations (>100 µM) of glucosamine-6-phosphate (Gln6P, FIG. 1A). In the absence of this important metabolite, no cleavage activity is observed. Although the natural sequence of the glmS element forms a unimolecular cis-cleaving ribozyme, active glmS ribozyme can also be constructed as a biomolecular cis-acting ribozyme. In this format, the cleaved strand, termed the substrate, includes the 5' base pairs that form half of the pairing element 1 (P1) and the conserved nucleotides upstream P1 (FIG. 1B). The non-cleaved ribozyme strand includes the 3' half of P1 and the remaining sequence of the glmS element. Using this biomolecular format, the 16-nucleotide substrate strand was labeled at the 3' and the 5' ends with the fluorescently probes fluorescein (Fl) and cy3, respectively. In an uncleaved substrate RNA, emission of the excited state fluorescein is quenched by the enforced proximity of the cy3 quencher. Upon cleavage in the presence of the Gln6P system, the binding of Gln6P (or related derivatives) to the glmS riboswitch can be rapidly screened using standard high-throughput techniques.

Figure 2:
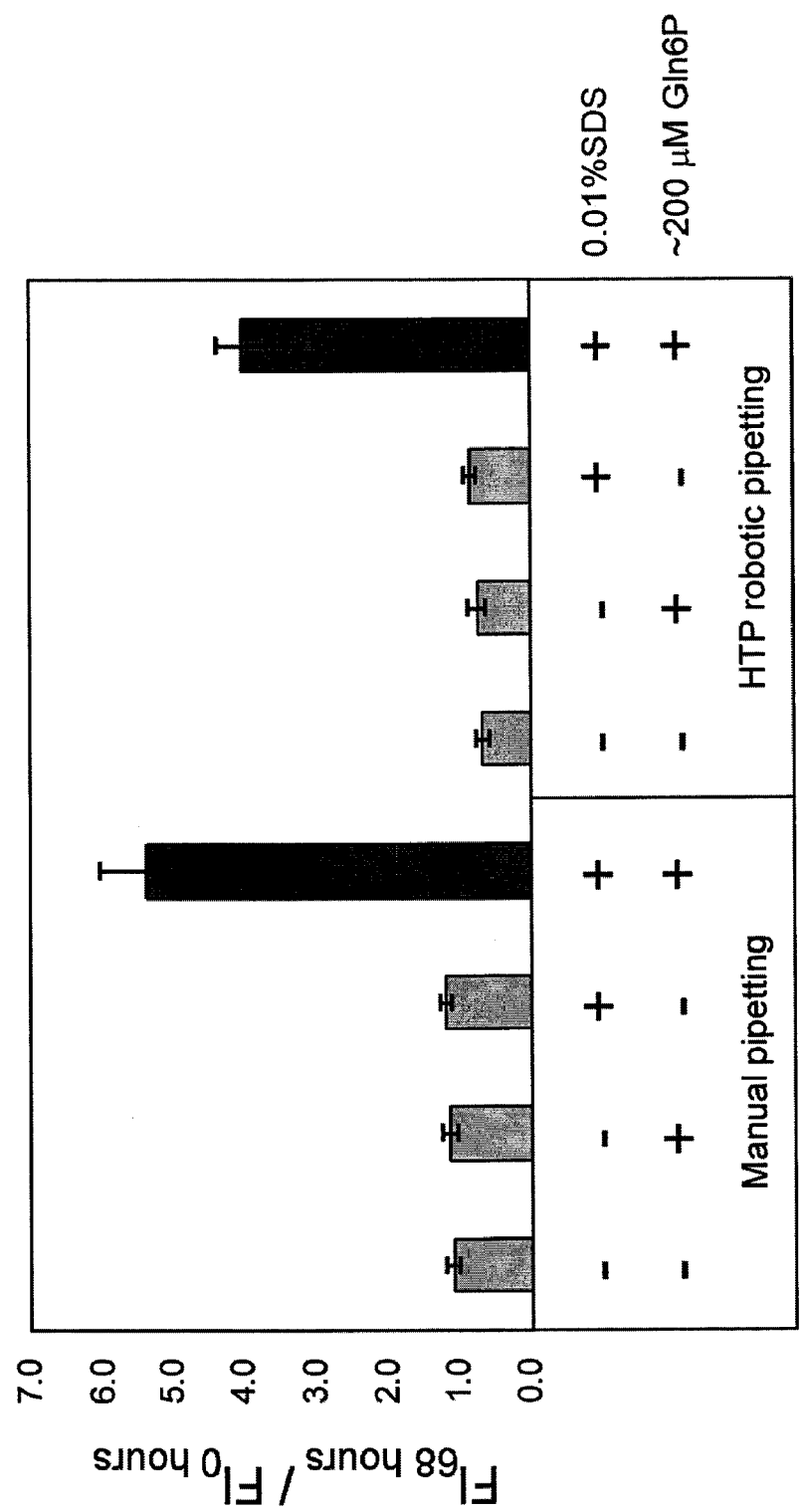
FIG. 2 shows the binding of Gln6P detected by the glmS ribozyme described in FIG. 1B.

After a minimum of 10 hours incubation, the fluorescence intensity of Fl increased ~4 fold in the presence of 160 µM glucosamine-6-phosphate, whereas no observable change was detected in the absence of effector (FIG. 2). Notably, when screening with high-throughput methods, the inclusion of 0.01% sodium dodecylsulfate was necessary for full ribozyme activity, consistent with previous demonstrations the utility of this detergent for preventing adhesion of small concentrations of the RNA to plastic tubes and plates. To further explore the discriminatory limits of this detection system, a library of sixteen Gln6P derivatives was also screened. The resulting glmS binding activities correspond well with the binding activities independently determined by gel electrophoresis methods (Table 1). Detection systems are also being used to screen a novel library of 20,000 compounds (Microsource Discovery Systems, Inc.) unrelated to Gln6P for binding the glmS ribozyme.

TABLE 1

Binding of Gln6P analogs to the glmS ribozyme measured by high-throughput fluorescence screen or in-line probing

| Analog | $Fl_{21h}/Fl_{gh}$ | Activity by electrophoretic in-line probing |
|---|---|---|
| Gln6P | 3.36 | Yes |
| Ma6P | 2.89 | Yes |
| 1-dGln6P | 2.52 | Yes |
| Glno16P | 0.80 | No |
| Gal6P | 1.69 | ND |
| β-MeO-Gln 6P | 1.02 | No |
| α-MeO-Gln 6P | 1.07 | No |
| MeN-Gln 6P | 3.49 | Yes |
| Me$_3$N-Gln 6P | 1.27 | No |

TABLE 1-continued

Binding of Gln6P analogs to the glmS ribozyme measured by high-throughput fluorescence screen or in-line probing

| Analog | $Fl_{21h}/Fl_{gh}$ | Activity by electrophoretic in-line probing |
|---|---|---|
| Al6P | 3.27 | Yes |
| Gln6PS | 1.11 | No |
| 1-AmGln 6P | 1.00 | No |
| Me$_3$N-Gln | 1.17 | No |
| AcNGln 6P | 2.28 | Weakly |
| Gln6P com | 2.24 | Yes |
| Gln com | 1.87 | Yes |

Figure 3:
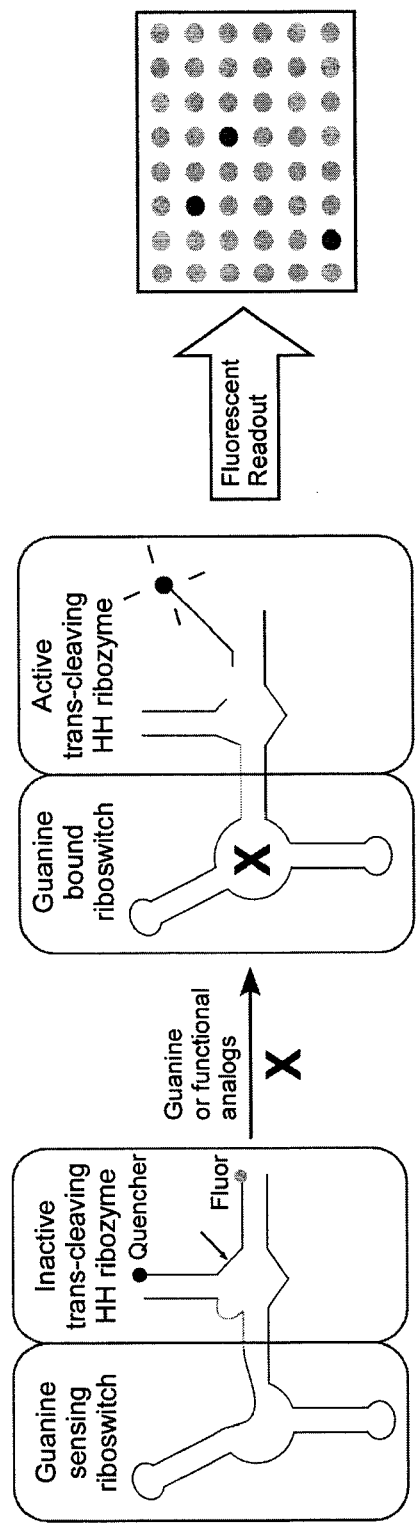
FIG. 3 shows the design of a high-throughput screen based on a riboswitch/ribozyme fusion to detect binding. In the absence of effector, the ribozyme folds predominantly into an inactive form. Binding of guanine or a functional analog favors an alternately folded, active ribozyme (cleavage site denoted by arrow.) A similar fluorophore-quencher pair as in FIG. 1 results in a fluorescent readout of effector binding.

2. Method 2: Use of Fret to Detect Substrate Cleavage by an Engineered Fusion Between Natural Riboswitch Elements and an RNA-Cleaving Ribozyme It has been repeatedly demonstrated that allosteric ribozymes can be engineered, wherein the binding of a highly selective aptamer to its cognate molecule triggers the correct folding and cleavage of a fused hammerhead ribozyme. This engineering is adapted to report the binding of specific metabolites to their cognate RNA riboswitches, which are equivalently naturally occurring aptamers. A fusion of the guanine sensitive riboswitch to a cis-cleaving hammerhead has been constructed to accurately report binding (FIG. 3). Using a similar fluorophore/quencher combination as in method 1, binding-induced ribozyme cleavage is sensed by an increase fluorescent signal. The activity, sensitivity, and ability of this ribozyme/riboswitch fusion to discriminate among closely-related metabolites are established.

Figure 4:
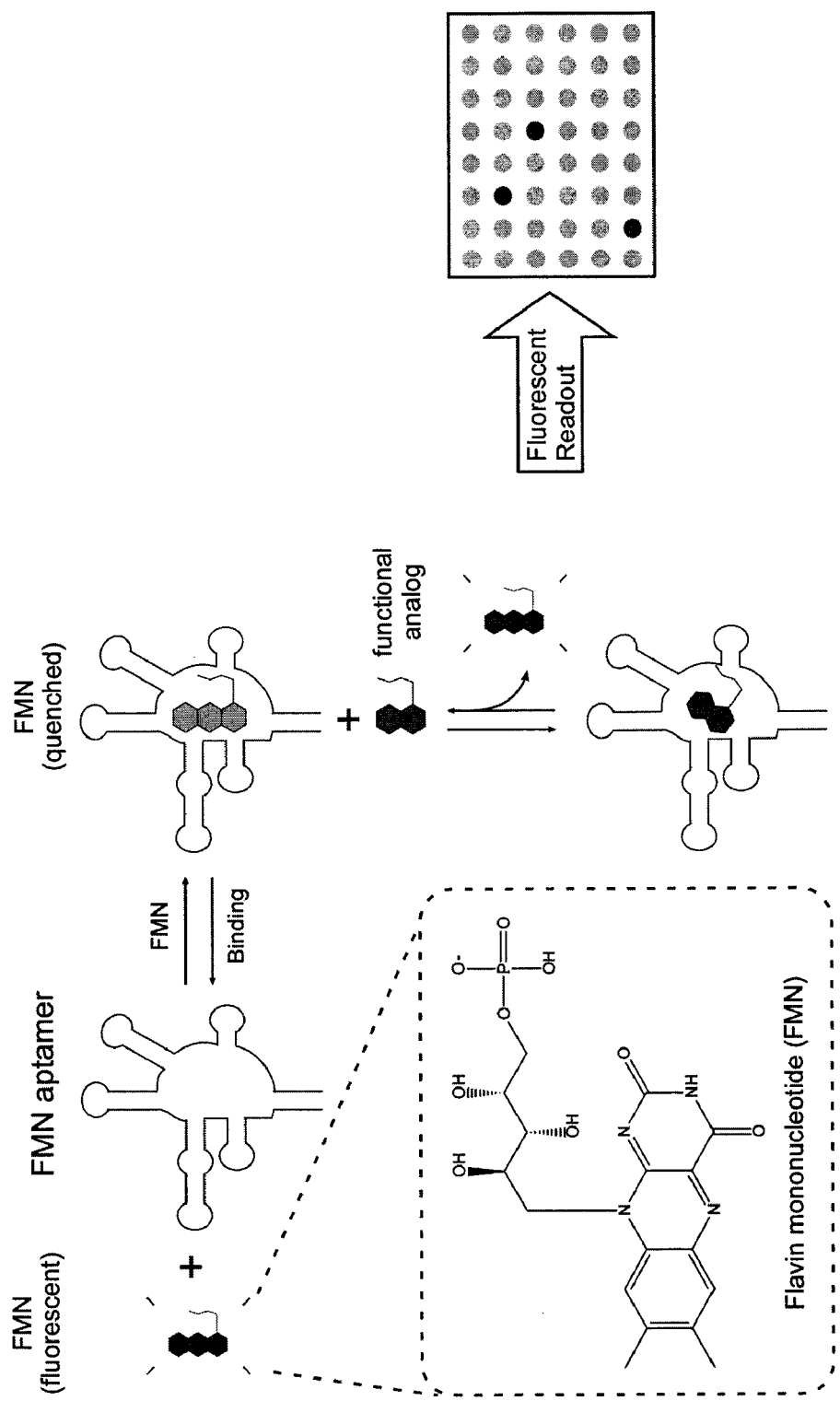
FIG. 4 shows high throughput screening strategy for novel analogs or mimics of FMN which bind to the FMN aptamer.

3. Method 3: Fluorescence Detection of the Displacement of a Naturally-Fluorescent Riboswitch Ligand by a Novel Compound The FMN riboswitch binds to fluorescently labeled active flavin mononucleotide (FMN, FIG. 4). It has been shown that the fluorescent intensity of FMN is decreased upon binding RNA. Novel ligands which compete with FMN for binding and thus displace FMN should cause an increase in fluorescence, providing a fluorescent readout of binding. To determine the magnitude of fluorescent increase induced by FMN displacement, a DNA oligonucleotide has been designed that hybridizes to a small segment of the unfolded RNA element. Since it forms an alternative secondary structure incapable of FMN binding, hybridization of this oligonucleotide to the unfolded RNA can shift the RNA-FMN binding equilibrium toward the unbound state, resulting in FMN displacement. This assay can be adapted to 96- or 384-well format, allowing the rapid screening of large chemical libraries for novel molecules that bind FMN riboswitches.

Figure 5:
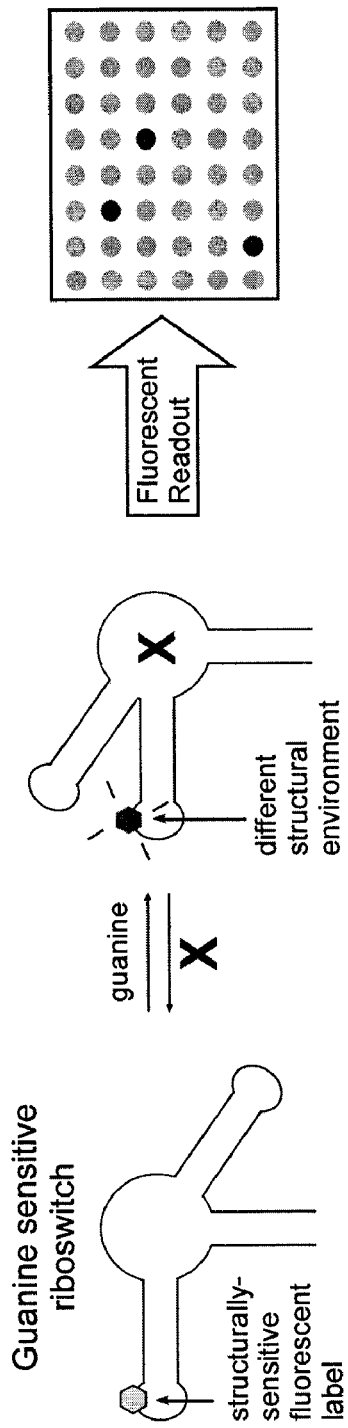
FIG. 5 shows the use of structurally-sensitive fluorescent probes to detect effector binding.

4. Method 4: The Use of a Structurally-Sensitive Fluorescent Tag to Detect Riboswitch Structural Changes Associated with Effector Binding A hallmark of riboswitch function is that the RNA structure changes upon ligand binding. By incorporating a structurally-sensitive fluorescent nucleoside derivative within the riboswitch RNA, the structural changes characteristic of ligand binding can be detected and harnessed as a means for fluorescent readout of binding (FIG. 5). Using established high throughput liquid handling and spectrofluormetric equipment, this readout can be adapted to 96- or 384-well format, allowing the rapid screening of large chemical libraries for novel molecules that elicit riboswitch activity. Nucleotides within the glycine- and guanine-responsive riboswitches that are tolerant to substitution by the fluorescent nucleotide 2-aminopurine are identified.

B. Example 2

Development and Application of a High-Throughput Assay for glmS Riboswitch Activators Riboswitches are newly-discovered gene control elements that are promising targets for antibacterial drug development. To facilitate the rapid discovery and development of riboswitch-targeted compounds, modern drug discovery techniques such as structure-based design and high-throughput screening will need to be applied. One promising riboswitch drug target is the glmS riboswitch, which upon binding glucosamine-6-phosphate (GlcN6P) catalyzes self-cleavage. Here an example of the development of a high-throughput assay for glmS ribozyme cleavage that relies on fluorescence resonance energy transfer (FRET) is provided. This assay can be used to screen for compounds that bind to and activate glmS ribozyme cleavage. To validate the screen, it was demonstrated that the assay identifies the compounds known to be active from a focused library of GlcN6P analogs whose affinities for the ribozyme had been determined by commonly used electrophoretic methods using radiolabeled RNA. Furthermore, the primary screen of a library of 960 compounds previously approved for use in humans identified five active compounds, one of which is a GlcN6P analog known to stimulate ribozyme activity. These results demonstrate that modern high-throughput screening techniques can be applied to the discovery of riboswitch-targeted drug compounds.

1. Materials and Methods

Chemicals and oligonucleotides. The following compounds were commercially available from the indicated sources: GlcN6P and glucosamine were purchased from Sigma. The synthesis, purification, and full characterization of the remaining GlcN6P analogs are reported elsewhere. Synthetic DNAs were purchased and purified before use as described previously (Seetharaman et al., Nature Biotechnology 2001; 19: 336-341). The library of 960 bioactive compounds was the Spectrum Collection™ purchased from MicroSource Discovery, Gaylordsville, Conn.

RNA preparation. The ribozyme domain representing the S. aureus glmS riboswitch (FIG. 6B) was prepared by in vitro transcription using T7 polymerase using methods similar to those described previously (Milligan and Uhlenbeck, Methods Enzymol 1989; 180: 51-62). The template for the transcription was generated from the corresponding region of the glmS leader sequence by PCR amplification using genomic DNA from S. aureus subsp. aureus Rosebach (ATCC 35556d). Transcribed RNA was purified by denaturing PAGE. The substrate strand used for radiolabeled cleavage analysis, 5'-AAAGCGCCUGUGCAAAUA-3' (SEQ ID NO:19) was purchased from Dharmacon, Inc. (Lafayette, Colo.), deprotected according to the manufacturer's directions, and 5'-$^{32}$P labeled as described previously (Seetharaman et al., Nature Biotechnology 2001; 19: 336-341). The substrate strand 5'-AAGCGCCUGUGCAAA-3'(SEQ ID NO:20), labeled at the 5'-end with a Cy3™ acceptor and at the 3'-end with a 5/6-FAM donor (isomeric mixture of 5- and 6-fluorescein) in purified form from IBA GmbH (Gottingen, Germany).

Low-throughput glmS kinetic analyses. All kinetic assays were conducted in 50 mM HEPES (pH 7.5 at 25° C.), 10 mM MgCl$_2$, and 200 mM KCl. To initiate the reaction, GlcN6P was added to give a final concentration of 200 µM. Kinetic assays with radiolabeled substrate were performed as described previously (Soukup, Nucleic Acids Res 2006; 34: 968-975). Rate constants were established by plotting the natural logarithm of the fraction of substrate remaining uncleaved versus time, and then determining the negative slope of the resulting line. For the highest rate constants, only the initial phase of the plots were used because ~20% of the RNA substrate remained uncleavable. Single reaction FRET-based kinetic assays were performed with $\lambda_{excit}$=488 nm (slit width=1 nm), $\lambda_{emit}$=523 nm (slit width=8 nm).

High-throughput glmS assay. High-throughput fluorescence assay validation and screening was performed in 384-well black polypropylene plates (Corning part number 3677) in a 10 µL solution of 50 mM HEPES (pH 7.5 at 25° C.), 10 mM MgCl$_2$, and 200 mM KCl, with 0.01% SDS where indicated in the text. A Tecan Aquarius multichannel pipettor (Tecan Group, LTD, Switzerland) was used for automated liquid handling. In a typical experiment, a reaction mixture containing buffer and both RNA domains was transferred into the assay plates with the liquid handler, the fluorescence was measured, and the reaction was initiated by the addition of ~50 nl of either GlcN6P, an analog of GlcN6P, or a library compound suspended at 10 mM in DMSO using the Tecan pin tool (~50 µM final concentration of compound). Plates were sealed with non-breathable sealing tape and protected from light for the specified incubation time, at which point the plate was briefly centrifuged and the fluorescence measured. All multiplate fluorescence measurements were conducted with a Wallach Envision (Perkin Elmer, Wellesly, Mass.) plate reader with a 480 nm excitation filter (30 nm bandwidth) and a 535 nm emission filter (25 nm bandwidth).

2. Results and Discussion

The increasingly frequent emergence of pathogenic bacteria that are resistant to commonly prescribed antibiotics places the discovery of novel antibacterial therapeutics at the forefront of medical concerns (Wolfson, Chem Biol 2006; 13: 1-3). Most currently prescribed antibiotics target one of only four cellular processes-translation, cell wall formation, folate biosynthesis, and DNA replication (Walsh, Nat Rev Microbiol 2003; 1: 65-70). Since many pathogens already have well-developed mechanisms to circumvent the effects of drugs directed at these processes, new targets will need to be discovered to revitalize our antibacterial arsenal (Nathan, Nature 2004; 431: 899-902). One class of RNA gene control elements termed riboswitches are promising candidates for novel and effective antibacterial drug targets (Sudarsan et al., Chem Biol 2005; 12: 1253-1358; Milewski, Biochim Biophys Acta 2002; 1597: 173-192).

Figure 6:
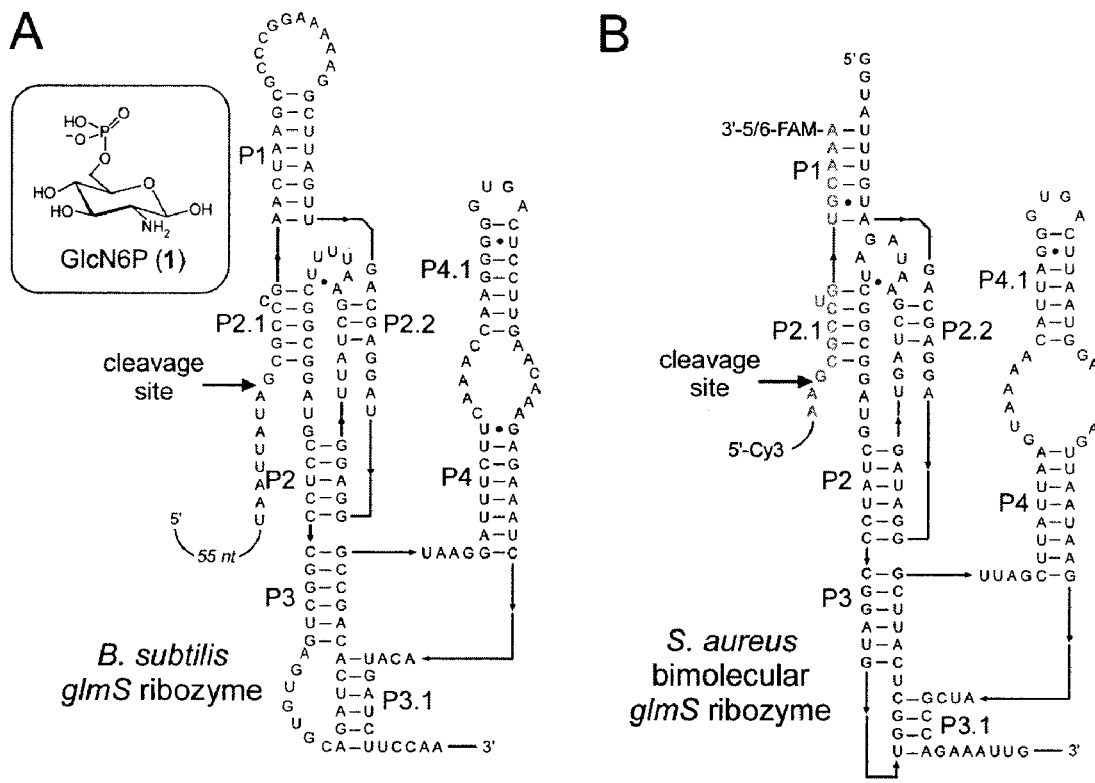
FIGS. 6A and 6B show the sequences and structures of two glmS ribozymes. A. A unimolecular glmS ribozyme from *B. subtilis* (from 5' end to 3' end, SEQ ID NOs:1-8). Arrow identifies the site of ribozyme-mediate cleavage stimulated by GlcN6P (Wolfson, Chem Biol 2006; 13: 1-3). B. A bimolecular glmS ribozyme construct derived from *S. aureus* (from 5' end to 3' end, SEQ ID NOs:9-18. This construct differs from the wild-type glmS ribozyme due to truncation of the P1 stem and the use of a 15-nucleotide substrate RNA (shown in grey; SEQ ID NOs:9 and 10). The substrate is labeled with a Cy3™ acceptor at its 5'-terminus and a 5/6-FAM donor at its 3'-terminus.

Riboswitches are structured RNA receptors found in the untranslated region (UTR) of messenger RNAs where they regulate the expression of the adjoining coding region or operon (Winkler et al., Nature 2002; 419: 952-956; Tucker and Breaker, Curr Opin Struct Biol 2005; 15: 342-348). Members of each known riboswitch class bind to a specific fundamental metabolite, which triggers structural changes in the adjoining mRNA that usually represses the expression of the protein(s) encoded in its open reading frame. One example is the 5'-untranslated region upstream of the glmS gene from Bacillus subtilis (FIG. 6A). The glmS gene codes for glucosamine-6-phosphate synthetase (Milewski, Biochim Biophys Acta 2002; 1597: 173-192). At sufficiently high concentrations (the apparent K$_D$ is 200 µM, but concentrations as low as 1 µM activate cleavage), the product of this enzyme, glucosamine-6-phosphate (GlcN6P), binds to the glmS riboswitch and triggers self-cleavage at a specific nucleotide of the glmS RNA (Winkler et al., Nature 2004; 428: 281-286). Thus, the glmS riboswitch is a GlcN6P-dependent autocatalytic ribozyme.

It was discovered that the glmS ribozyme can be an excellent target for antibacterial drug development Repression of the glmS gene would reduce the cellular concentration of GlcN6P, a precursor of uridine 5'-diphospho-N-acetyl-D-glucosamine, which is an essential substrate for cell wall formation (Milewski, Biochim Biophys Acta 2002; 1597: 173-192). Accordingly, the GlmS protein is essential for normal cell growth (Kobayashi et al., Proc Natl Acad Sci USA 2003; 100: 4678-4683). Thus, glmS repression by compounds that trigger ribozyme action would inhibit growth. Moreover, since the glmS ribozyme is present and highly conserved in genomes of many high-priority bacterial pathogens, including *Bacillus anthracis* and *Staphylococcus aureus*, glmS ribozyme-targeted drugs can be used to inhibit a range of both gram negative and gram positive bacterial pathogens.

To enable rapid riboswitch-targeted drug discovery, modern technologies such as high-throughput screening for ligands to these RNA receptors would be valuable. A recent report describes a high-throughput-compatible assay for detecting cleavage of a unimolecular *B. subtilis* glmS ribozyme (Mayer and Famulok, ChemBioChem 2006; 7:602-604). A complimentary and fully automatable high-throughput assay was developed to screen chemical libraries for compounds that bind to and activate a bimolecular glmS ribozyme from *S. aureus*. A collection of rationally-designed GlcN6P analogs and a library of 960 bioactive compounds was screened for those that bind to and activate the ribozyme. The activity reported by this screen for the GlcN6P analogs accurately reflects the binding affinities measured by a commonly used assay.

Figure 7:
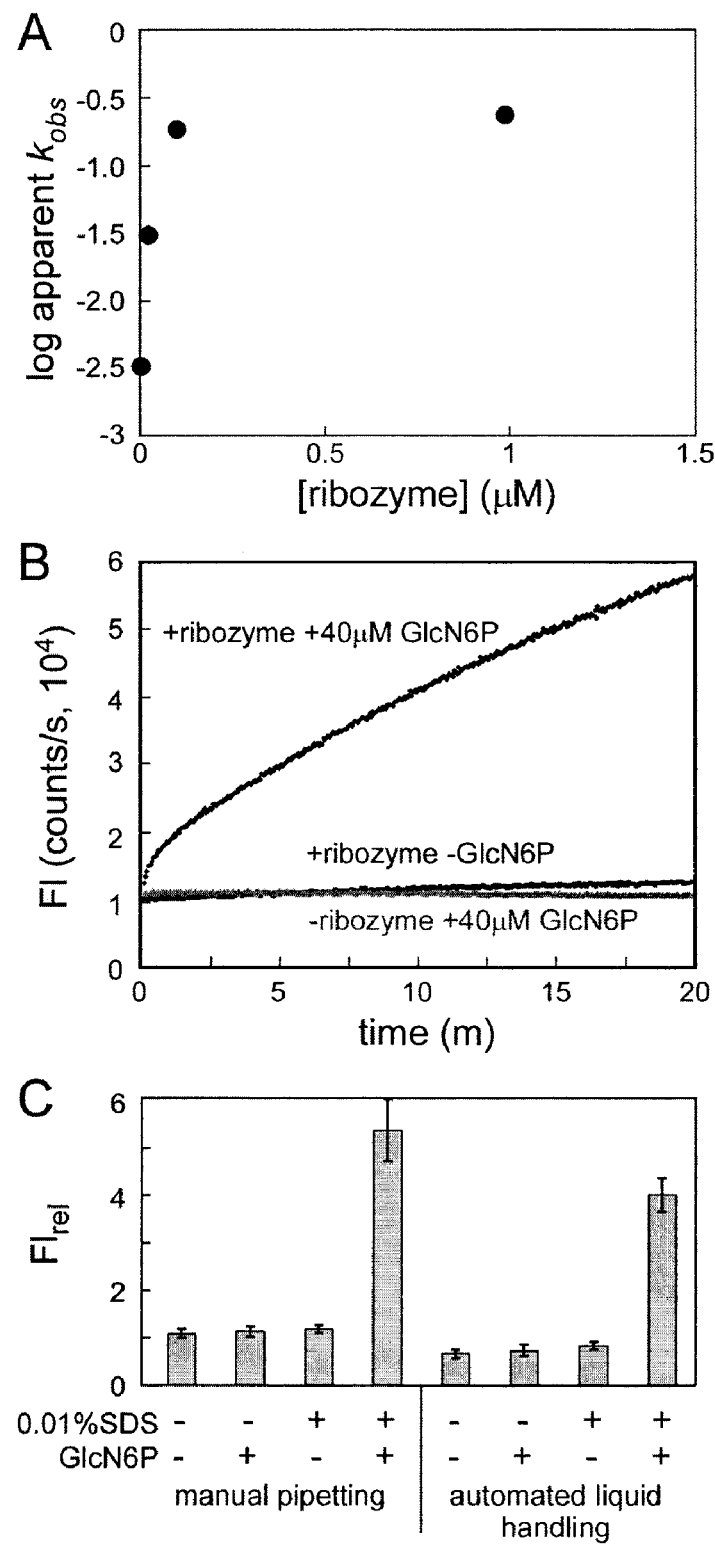
FIGS. 7A, 7B and 7C show RNA cleavage activity of a bimolecular glmS ribozyme. A. The apparent $k_{obs}$ for substrate cleavage (0.1 nM, 5'-$^{32}$P-radiolabeled) was measured as a function of ribozyme concentration. B. Cleavage of the bimolecular ribozyme-substrate complex in the presence of 40 μM GlcN6P (upper black trace) monitored by an increase in fluorescence of the FRET pair. No activity was observed in the absence of either the ribozyme (grey) or GlcN6P (lower black trace). C. Change in fluorescence upon incubation of 10 nM each of the substrate and ribozyme RNAs in a 384-well plate for 68 hours in the presence of 200 μM GlcN6P. The error bars indicate the standard deviation for each value from eight replicate reactions.

Although the glmS ribozyme sequence is highly conserved among many bacterial species, the *S. aureus* sequence was chosen for screening development because of its clinical importance. To facilitate detection of cleavage, the natural self-cleaving glmS ribozyme was converted to a bimolecular ribozyme (FIG. 6B) in which separate substrate and ribozyme oligonucleotides associate via a truncated P1 stem. A similar bimolecular glmS ribozyme from *B. subtilis* was recently characterized and found to have similar catalytic properties as the natural unimolecular ribozyme (Soukup, Nucleic Acids Res 2006; 34: 968-975). The RNA substrate encompasses the 5'-half of the shortened P1 stem and the conserved nucleotides surrounding the cleavage site, whereas the ribozyme strand contains the 3'-half of P1 and the remainder of the glmS sequence from *S. aureus*. The cleavage activity of this bimolecular ribozyme was confirmed under multiple turnover conditions using a 5'-radiolabeled substrate (FIG. 7A). At 0.5 µM ribozyme, 200 µM GlcN6P, and saturating substrate concentrations, the bimolecular construct cleaves with an apparent rate constant of 0.25 $min^{-1}$ at 25° C., comparable to the previously reported single-turnover rate constant of 1 $min^{-1}$ (Winkler et al., Nature 2004; 428: 281-286). Under these conditions, the apparent $K_D$ measured for the two strands was 0.2 µM, comparable to the value of 1 µM reported for a similar bimolecular construct (Soukup, Nucleic Acids Res 2006; 34: 968-975).

To enable FRET detection of cleavage, the substrate was synthesized with a 5-(and 6-)-carboxyfluorescein (5/6-FAM) donor at the 3' end and a Cy3™ acceptor at the 5' end. When excited at 485 nm, the 5/6-FAM donor normally emits at a maximum wavelength of 526 nm. When the substrate strand is intact, however, the fluorescence of 5/6-FAM is reduced presumably due to quenching by the proximal Cy3™ acceptor. After addition of GlcN6P and cleavage of the substrate strand, the two product strands dissociate, relieving the proximity of 5/6-FAM and Cy3™, with a concomitant increase of 5/6-FAM fluorescence. Similar fluorescence-based systems have been used to detect ribozyme cleavage in real time (Singh et al., RNA 1999; 5: 1348-1356; Hanne et al., Nucleosides Nucleotides 1998; 17: 1835-1850). Using this FRET detection strategy, the addition of 40 µM GlcN6P induces an increase in the fluorescence signal of greater than 6 fold within 20 minutes (FIG. 7B). The modest burst in fluorescence increase could be due to a conformational change in the substrate that occurs upon ligand binding. Tertiary contacts between ribozyme and substrate would constrain the substrate to a greater extent compared to that caused by the short base paired region, thus increasing the average distance between donor and acceptor. Importantly, no fluorescence increase was observed over this time course in the absence of either GlcN6P or the ribozyme.

To facilitate rapid solution-based measurement of cleavage for large compound libraries, the assay conditions were optimized for automated liquid handling and fluorescence measurement in 384-well microplates. To reduce demand for enzyme and substrate RNAs, the concentrations of these molecules were varied to determine the minimal concentration of each that can be used to give a reproducible and statistically significant increase in the fluorescent signal. At 10 nM of each strand, a 4-fold increase in fluorescence was observed after 68 hours when 100 µM GlcN6P was present (FIG. 7C). At this low RNA concentration, the signal increase was dependent upon the inclusion of 0.01% SDS, perhaps because it minimizes adhesion of the RNA to the polypropylene plates. At incubation times less than 48 hours, the increase in fluorescence was noticeably less, most likely because the concentration of the two RNA strands is well below the measured dissociation constant of 0.2 µM, slowing the observed cleavage rate. Nevertheless, the fact that a signal increase is not observed in the absence of GlcN6P confirms that the signal increase reports ribozyme catalysis during this time course, rather than non-specific RNA degradation. Furthermore, although ribozyme-substrate complex formation is most likely a rate limiting step in our high-throughput assays, the total fluorescence increase is a function of how well the ligand is able to induce ribozyme action once complex formation occurs.

The signal change after incubation was nearly identical when the reactions were prepared either by manual pipetting or by the automated liquid handler (FIG. 7C). From these data, the Z' for the screen can be calculated:

$$Z'=1-3*(SD_{positive}+SD_{negative})/|M_{positive}-M_{negative}|$$

where $SD_{positive}$, $SD_{negative}$, $M_{positive}$, and $M_{negative}$ denote the standard deviation and mean for wells with or without GlcN6P, respectively. Z' is a relative indication of the separation between the positive and negative control populations and is widely accepted as an assessment of the statistical performance of a screen (Zhang et al., J Biomol Screen 1999; 1999: 67-73). The Z' calculated for the data in FIG. 7C is 0.64, well above the industrial standard of >0.5 for a pharmaceutically useful screen, although this number was determined with fewer replicates than is typically used. This Z' also compares favorably with the previously published unimolecular glmS screen (Mayer and Famulok, ChemBioChem 2006; 7:602-604). This confirms the utility of the screen for high-throughput library screening.

Figure 8:
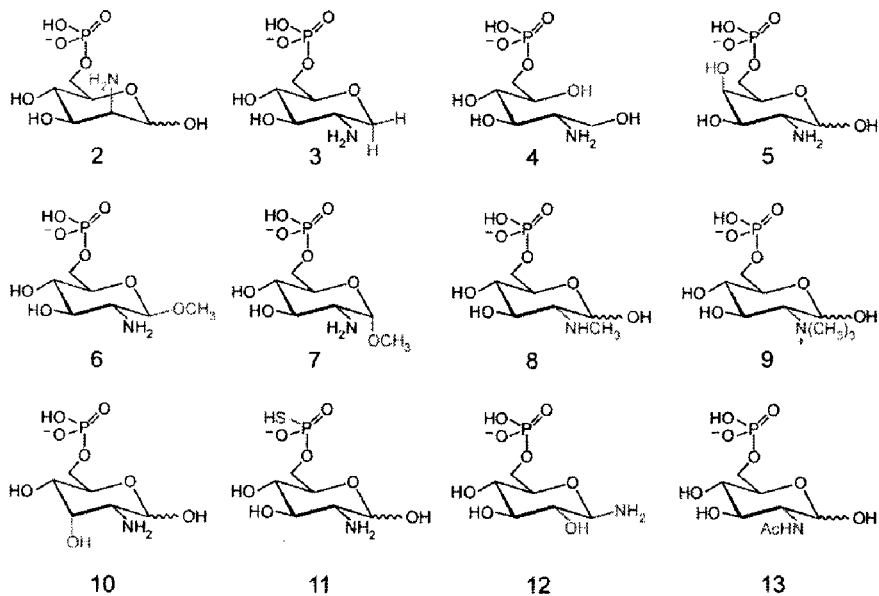
FIGS. 8A and 8B show identification of GlcN6P analogs that induce ribozyme activity. A. The structures of the GlcN6P that were tested for their ability to activate glmS cleavage. B. The fluorescence at 21 or 44 hours, relative to time zero (left axis), after the addition of each analog identifies which compounds activate cleavage. For comparison, the relative fluorescence with no ligand ("NL") is 0.8 and 0.9 at 21 and 44 hours, respectively, and the relative fluorescence after the addition of 200 μM GlcN6P (Wolfson, Chem Biol 2006; 13: 1-3) is 3.5 and 3.4 at 21 and 44 hours, respectively. For comparison, PAGE analysis revealed that each of the circled compounds activates the glmS ribozyme with an apparent affinity within 10-fold of GlcN6P.
Figure 8:
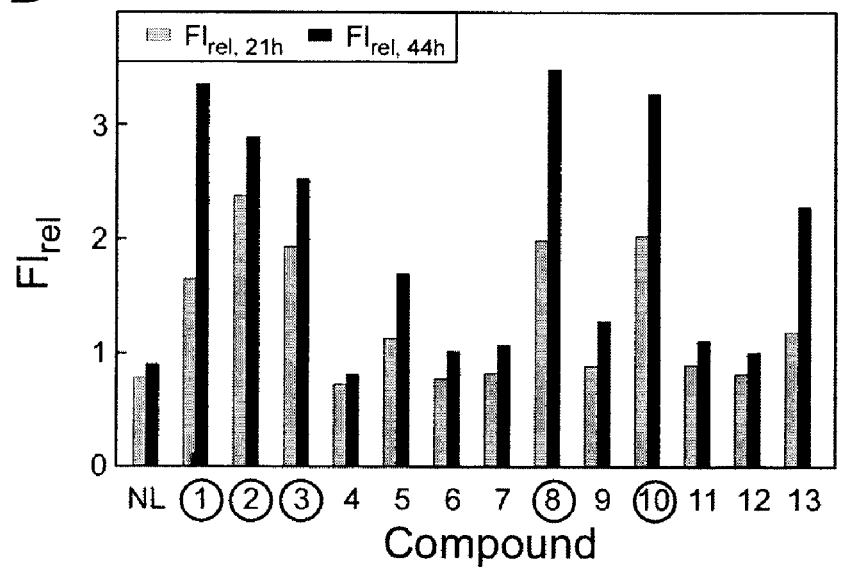

To evaluate how well the assay can distinguish active from inactive compounds, we screened a library of twelve GlcN6P analogs (FIG. 8) whose relative binding affinities for the glmS ribozyme had been previously determined by electrophoretic methods. Each compound whose binding affinity for the ribozyme is within 10 fold of GlcN6P showed at least a 2.5-fold increase in fluorescence, compared to a 3.5-fold increase in fluorescence for GlcN6P. This cutoff for functional compounds ("hits") of 2.5-fold increased fluorescence represents a statistically significant 18 standard deviations over the mean fluorescence value in the absence of ligand ("NL"). Conversely, each compound whose affinity is less than 10 fold of GlcN6P shows less than 1.5-fold increase in the fluorescence signal, except 5 and 13. The larger fluorescence increase observed for 5 and 13 most likely indicates that these compounds stimulate a slower rate of cleavage that is detectable after 44 hours but was undetectable by the previous gel analysis after a 30 minute incubation. A similar case exists for glucosamine, which induces a 3.0-fold increase in fluorescence after 44 hours, even though its measured affinity for the ribozyme is more than 100-fold lower than GlcN6P (McCarthy et al., Chem Biol 2005; 12: 1221-1226). Thus, the fluorescent report from the high-throughput screen accurately reflects binding activity for the glmS ribozyme.

Figure 9:
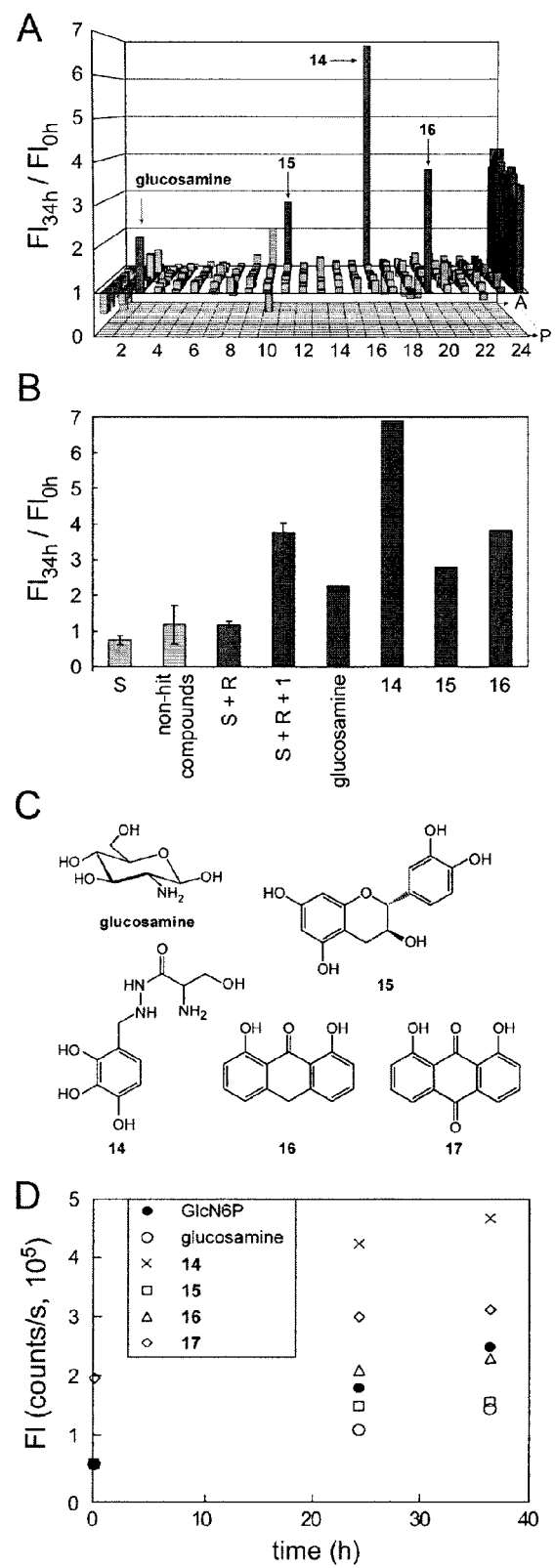
FIGS. 9A, 9B, 9C and 9D show results of a 960-compound pilot glmS activity screen. A. Plate 1 of three shows the fluorescence response over 384 wells. Columns 1 and 2 contain only the substrate strand. Column 23 (next to last) contains the substrate and ribozyme strands, and column 24 (last) contains the ribozyme and substrate strands and 80 μM GlcN6P. Wells in which the fluorescence response is greater than 10-standard deviations above the no-ligand control are highlighted labeled (glucosamine, 15, 14 and 16). B. The mean fluorescence response is shown for each control reaction and hit compound in Plate 1. Error bars indicate one standard deviation. C. Five hits were identified from a screen of the 960-compound Spectrum Collection that show greater than 2.3-fold fluorescence increase after 44 hours. D. Secondary analysis demonstrates that each of the five compounds identified in C exhibits a time-dependent increase in fluorescence.

As a model screen to search for new compounds that can bind to and/or activate the glmS ribozyme, a commercially available library of 960 bioactive compounds approved for use in humans was screened. In control wells with only GlcN6P added, the fluorescence signal of the ribozyme-substrate mixture increased by 3.74-fold (±0.28) after 34 hours (rightmost row in FIG. 9A and S+R+1 in FIG. 9B), compared to only a 1.18-fold (±0.09) increase in the absence of ligand (next to rightmost row in FIG. 9A and S+R in FIG. 9B), a difference of 28 standard deviations. For wells containing a library compound, an increase in fluorescence of greater than 10 standard deviations above the mean relative fluorescence in the absence of ligand was considered to indicate an active compound. (This hit threshold was chosen in an effort to capture the maximum possible hit compounds). Using this parameter, five hit compounds were identified (FIG. 9C), most notably glucosamine. This hit rate of 0.06% compares favorably with other recently published screens (Zhang et al., J Biomol Screen 2005; 10: 695-704; Kroemer, Biochem Soc Trans 2003; 31: 980-984; Macarrón and Hertzberg, In: WP Janzen, ed. Totowa, N.J.: Humana Press, 2002: 1-29), as does the average Z' factor of 0.57 calculated for each plate of the screen. Notably, although the previously described glmS screen showed no observable activity with glucosamine after 30 minutes (Mayer and Famulok, ChemBioChem 2006; 7:602-604), it is reasonable to assume that the longer incubation time used herein permits identification of this analog that binds with 100-fold weaker affinity than GlcN6P (McCarthy et al., Chem Biol 2005; 12: 1221-1226).

Each of the five compounds identified was retested for glmS activation with either the fluorescence screen or by electrophoretic methods. Surprisingly, although each compound induces a reproducible and time-dependent increase in fluorescence (FIG. 9D), only glucosamine stimulates detectable cleavage on a gel after incubating for 2 hours (not shown). This result mirrors the previously-described glmS screen (Mayer and Famulok, ChemBioChem 2006; 7:602-604), in that novel glmS activating compounds have not yet been identified, presumably due to the limited size and diversity of the library. Moreover, these types of infrequent false-positive hits have been observed for other fluorescence-based high-throughput screens (Zhang et al., J Biomol Screen 2005; 10: 695-704) and can readily be confirmed or refuted in our case with the secondary ribozyme cleavage assay (Soukup and Breaker, RNA 1999; 5: 1308-1325). One possible explanation for the false positives is that they quench or otherwise modify the fluorescent label on the RNA over the 44 hour time course, or that the compounds become fluorescent over time. Nevertheless, the identification of glucosamine confirms that this screen can identify even low affinity glmS-activating compounds from complex compound libraries.

In summary, a fully automatable and statistically robust high-throughput screen was developed for identifying compounds that bind to and activate the glmS ribozyme. This demonstrates that modern drug discovery technology can be applied to the discovery and development of riboswitch targeted drugs. Moreover, the technology described in this example and can be readily reconfigured for other riboswitches by engineering an allosteric fusion between an RNA-cleaving ribozyme and a riboswitch aptamer as previously described (Breaker, Curr Opin Biotechnol 2002; 13: 31-39; Breaker, Nature 2004; 432: 838-845). These types of screens can significantly advance the discovery of novel antibacterial drugs directed at these promising classes of RNA targets.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a riboswitch" includes a plurality of such riboswitches, reference to "the riboswitch" is a reference to one or more riboswitches and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

---

We claim:

1. A method comprising:
   (a) bringing into contact a ribozyme riboswitch, a substrate labeled with a conformation dependent label and a compound, wherein the substrate is a substrate for cleavage by the ribozyme riboswitch, wherein the cleavage occurs in trans, wherein the ribozyme riboswitch is a glmS riboswitch; and
   (b) detecting change in fluorescence, wherein a change in fluorescence indicates cleavage of the substrate by the ribozyme riboswitch.

2. The method of claim 1, wherein cleavage of the substrate indicates that the compound binds to the ribozyme riboswitch.

3. The method of claim 1, wherein cleavage of the substrate indicates that the compound activates the ribozyme riboswitch.

4. The method of claim 1, wherein cleavage of the substrate indicates that the compound interacts with the ribozyme riboswitch.

5. The method of claim 1, wherein cleavage of the substrate indicates that the compound induces a conformational change in the ribozyme riboswitch.

6. The method of claim 1, wherein cleavage of the substrate indicates that the compound is a trigger molecule for the ribozyme riboswitch.

7. The method of claim 1, wherein a change in fluorescence indicates that the compound modulates substrate cleavage.

8. The method of claim 1, wherein the conformation dependent label is a Fluorescent Resonance Energy Transfer (FRET) label.

9. The method of claim 1, wherein steps (a) and (b) are performed a plurality of times in parallel using a plurality of different compounds, wherein cleavage of the substrate in the presence of one of the compounds indicates that that compound activates the ribozyme riboswitch.

10. The method of claim 9, wherein steps (a) and (b) are performed at least 20, 30, 40, 50, 75, 96, 100, 150, 200, 250, 300, 384, or 400 times in parallel.

11. The method of claim 9, wherein steps (a) and (b) are performed a plurality of times in parallel a plurality of times in sequence.

12. The method of claim 11, wherein steps (a) and (b) are performed a plurality of times in parallel at least 3, 5, 10, 15, 20, 30, 40, 50, 75, 100, 150, 200, 250, 300, or 400 times in sequence.

13. The method of claim 1, wherein the method is performed using a high throughput system.

14. The method of claim 1, wherein the ribozyme riboswitch is naturally occurring.

15. The method of claim 1, wherein the ribozyme riboswitch is engineered.

16. The method of claim 15, wherein the ribozyme riboswitch is derived from a naturally occurring ribozyme riboswitch that self-cleaves, wherein the ribozyme riboswitch is engineered by removing a segment comprising the cleavage site.

17. The method of claim 16, wherein the substrate replaces the removed segment.

18. The method of claim 15, wherein the ribozyme riboswitch is a chimera.

19. The method of claim 18, wherein the chimera comprises a riboswitch fused to a ribozyme.

20. The method of claim 19, wherein the ribozyme is derived from a ribozyme that self-cleaves, wherein a segment comprising the cleavage site of the ribozyme is removed.

21. The method of claim 20, wherein the substrate replaces the removed segment.

22. The method of claim 19, wherein the riboswitch is a guanine riboswitch.

23. The method of claim 19, wherein the ribozyme is a hammerhead ribozyme.

24. The method of claim 1, wherein the compound is a protein or peptide.

25. The method of claim 1, wherein the compound is or comprises a small organic molecule.

26. A method comprising:
  (a) bringing into contact a ribozyme riboswitch, a substrate labeled with a conformation dependent label and a compound, wherein a segment comprising the cleavage site is removed from the ribozyme riboswitch, wherein the ribozyme riboswitch is a glmS riboswitch and wherein the substrate is a substrate for cleavage by the ribozyme riboswitch; and
  (b) detecting change in fluorescence, wherein a change in fluorescence indicates cleavage of the substrate by the ribozyme riboswitch.

* * * * *

SEQUENCE LISTING

<160> NUMBER OF SEQ ID NOS: 20

<210> SEQ ID NO 1
<211> LENGTH: 15
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 1
uaauuauagc gcccg                                                        15

<210> SEQ ID NO 2
<211> LENGTH: 28
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 2
aacuaagcgc ccggaaaaag gcuuaguu                                          28

<210> SEQ ID NO 3
<211> LENGTH: 9
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 3 gacgaggau                                                                9

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4 ggagg                                                                    5

<210> SEQ ID NO 5
<211> LENGTH: 26
<212> TYPE: RNA
<213> ORGANISM: Artificial Sequence
<220> FEATURE:
<223> OTHER INFORMATION: Description of Artificial Sequence; note =
      synthetic construct -continued

```
<400> SEQUENCE: 5
uuaucgaauu uucggcggau gccucc                                          26

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 6
cggcugagug ugcagaucac agccg                                           25

<210> SEQ ID NO 7
<211> LENGTH: 49
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 7
uaaggauuuc uucaaaccaa gggggugacu ccuugaacaa agagaaauc                 49

<210> SEQ ID NO 8
<211> LENGTH: 14
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 8
acaugaucuu ccaa                                                       14

<210> SEQ ID NO 9
<211> LENGTH: 9
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 9 aagcgccug                                                              9

<210> SEQ ID NO 10
<211> LENGTH: 6
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 10 ugcaaa                                                                 6

<210> SEQ ID NO 11
<211> LENGTH: 10
<212> TYPE: RNA
<213> ORGANISM: Artificial Sequence
<220> FEATURE:
<223> OTHER INFORMATION: Description of Artificial Sequence; note =
      synthetic construct
```

```
<400> SEQUENCE: 11
gguauuugua                                                          10

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12 gacgagga                                                             8

<210> SEQ ID NO 13
<211> LENGTH: 6
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 13 ggauag                                                               6

<210> SEQ ID NO 14
<211> LENGTH: 28
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 14
ugaucgaaua gaucggcgga ugcuaucc                                      28

<210> SEQ ID NO 15
<211> LENGTH: 6
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 15 cggaug                                                               6

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 16
uggcucauuc g                                                        11

<210> SEQ ID NO 17
<211> LENGTH: 51
<212> TYPE: RNA
<213> ORGANISM: Artificial Sequence
<220> FEATURE:
<223> OTHER INFORMATION: Description of Artificial Sequence; note =
      synthetic construct
```

```
<400> SEQUENCE: 17
uuagcuuauu aaguaaaaca uuagggugac uuaauggaca aaguuaauaa g         51

<210> SEQ ID NO 18
<211> LENGTH: 14
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 18
aucgccagaa auug                                                  14

<210> SEQ ID NO 19
<211> LENGTH: 18
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 19
aaagcgccug ugcaaaua                                              18

<210> SEQ ID NO 20
<211> LENGTH: 15
<212> TYPE: RNA
<213> ORGANISM: Artificial Sequence
<220> FEATURE:
<223> OTHER INFORMATION: Description of Artificial Sequence; note =
      synthetic construct

<400> SEQUENCE: 20
aagcgccugu gcaaa                                                 15
```